(12) United States Patent
Van Ginderachter et al.

(10) Patent No.: US 11,858,960 B2
(45) Date of Patent: Jan. 2, 2024

(54) HUMAN PD-L1-BINDING IMMUNOGLOBULINS

(71) Applicant: Vrije Universiteit Brussel, Brussels (BE)

(72) Inventors: Jo Van Ginderachter, Ninove (BE); Geert Raes, Sint-Genesius-Rode (BE); Nick Devoogdt, Eppegem (BE); Marleen Keyaerts, Tervuren (BE); Quentin Lecocq, Ganshoren (BE); Catarina Xavier, Merchtem (BE); Karine Breckpot, Merchtem (BE); Katrijn Broos, Sing-Katelijne-Waver (BE); Jessica Bridoux, Etterbeek (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 23 days.

(21) Appl. No.: 16/977,145

(22) PCT Filed: Mar. 1, 2019

(86) PCT No.: PCT/EP2019/055133
§ 371 (c)(1),
(2) Date: Sep. 1, 2020

(87) PCT Pub. No.: WO2019/166622
PCT Pub. Date: Sep. 6, 2019

(65) Prior Publication Data
US 2021/0147546 A1    May 20, 2021

(30) Foreign Application Priority Data

Mar. 1, 2018   (EP) .................................... 18159388
Nov. 27, 2018  (EP) .................................... 18208646

(51) Int. Cl.
*C07K 16/28*   (2006.01)
*A61K 51/10*   (2006.01)

(52) U.S. Cl.
CPC ...... *C07K 16/2827* (2013.01); *A61K 51/1027* (2013.01); *C07K 2317/24* (2013.01); *C07K 2317/565* (2013.01); *C07K 2317/569* (2013.01); *C07K 2317/76* (2013.01); *C07K 2317/92* (2013.01); *C07K 2319/21* (2013.01)

(58) Field of Classification Search
None
See application file for complete search history.

(56) References Cited

FOREIGN PATENT DOCUMENTS

| | | |
|---|---|---|
| EP | 0368684 B2 | 11/1989 |
| EP | 1134231 A1 | 2/2001 |
| EP | 1433793 A1 | 9/2002 |
| NO | 2006122787 A1 | 11/2006 |
| WO | 199404678 A1 | 3/1994 |
| WO | 199425591 A1 | 11/1994 |
| WO | 199504079 A1 | 2/1995 |
| WO | 199634103 A1 | 10/1996 |
| WO | 199749805 A2 | 12/1997 |
| WO | 199937681 A2 | 7/1999 |
| WO | 200040968 A1 | 7/2000 |
| WO | 200043507 A1 | 7/2000 |
| WO | 200065057 A1 | 11/2000 |
| WO | 200121817 A1 | 3/2001 |
| WO | 2001040310 A2 | 6/2001 |
| WO | 2001044301 A1 | 6/2001 |
| WO | 2001090190 A2 | 11/2001 |
| WO | 200248193 A2 | 6/2002 |
| WO | 2003002609 A2 | 1/2003 |
| WO | 2003025020 A1 | 3/2003 |
| WO | 2003035694 A2 | 5/2003 |
| WO | 2003050531 A2 | 6/2003 |
| WO | 2003054016 A2 | 7/2003 |
| WO | 2003055527 A2 | 7/2003 |
| WO | 2004041862 A2 | 5/2004 |
| WO | 2004041863 A2 | 5/2004 |
| WO | 2004041865 A2 | 5/2004 |
| WO | 2004041867 A2 | 5/2004 |
| WO | 2004062551 A2 | 7/2004 |
| WO | 2004068820 A2 | 8/2004 |
| WO | 200518629 A1 | 3/2005 |
| WO | 2005044858 A1 | 9/2005 |
| WO | 2006003388 A2 | 1/2006 |
| WO | 2006030220 A1 | 3/2006 |
| WO | 2006040153 A2 | 4/2006 |
| WO | 2006079372 A1 | 8/2006 |
| WO | 2006122786 A2 | 11/2006 |
| WO | 2006122825 A2 | 11/2006 |
| WO | 2008020079 A1 | 2/2008 |
| WO | 2008071447 A2 | 6/2008 |
| WO | 2008101985 A2 | 8/2008 |
| WO | 2008142164 A2 | 11/2008 |

(Continued)

OTHER PUBLICATIONS

Aguiar Jr., et al., "The effect of PD-L1 testing on the cost-effectiveness and economic impact of immune checkpoint inhibitors for the second-line treatment of NSCLC", Annals of Oncology, vol. 28, pp. 2256-2263, 2017.

(Continued)

*Primary Examiner* — Marianne P Allen
(74) *Attorney, Agent, or Firm* — Dinsmore & Shohl LLP

(57) ABSTRACT

The invention relates to polypeptides, in particular polypeptides comprising an immunoglobulin domain, binding to human Programmed Death Ligand-1 (huPDL1) and to applications of such polypeptides such as for use as a medicament or for use as diagnostic agent, for example as an immunotracer.

13 Claims, 29 Drawing Sheets

Specification includes a Sequence Listing.

(56) References Cited

FOREIGN PATENT DOCUMENTS

| | | | |
|---|---|---|---|
| WO | 2009030285 | A1 | 3/2009 |
| WO | 2016039749 | A1 | 3/2016 |
| WO | 2016086021 | A1 | 6/2016 |
| WO | 2016086036 | A2 | 6/2016 |
| WO | 2017059397 | A1 | 4/2017 |
| WO | 2017072273 | A1 | 5/2017 |
| WO | 2017072280 | A1 | 5/2017 |
| WO | 2020160229 | A1 | 8/2020 |

OTHER PUBLICATIONS

Aslaab, et al., "PD-1 and PD-L1 Checkpoint Signaling Inhibition for Cancer Immunotherapy: Mechanism, Communications, and Clinical Outcome", Frontiers in Pharmacology, vol. 8, pp. 1-15, Aug. 2017.

Barbas III., et al., "In vitro evolution of a neutralizing human antibody to human immunodeficiency virus type 1 to enhance affinity and broaden strain cross-reactivity", Proc. Natl. Acad. Sci., vol. 91, pp. 3809-3813, Apr. 1994.

Bensch, et al., "Zr-atezolizumab imaging as a non-invasive approach to assess clinical response to PD-L1 blockade in cancer", Nature Medicine, vol. 24, pp. 1852-1864, Dec. 2018.

Boding, et al., "TCR Down-Regulation Controls T Cell Homeostasis", The Journal of Immunology, vol. 183, pp. 4994-5005, 2009.

Bonehill, et al., "Single-Step Antigen Loading and Activation of Dendritic Cells by mRNA Electroporation for the Purpose of Therapeutic Vaccination in Melanoma Patients", Cancer Therapy: Preclinical, vol. 10, pp. 3366-3376, May 15, 2009.

Breckpot, et al., "Lentivirally transduced dendritic cells as a tool for cancer immunotherapy", The Journal of Gene Medicine, vol. 5, pp. 654-667, 2003.

Brennick, et al., "Neoepitopes as cancer immunotherapy targets: key challenges and opportunities", Immunotherapy Review, vol. 4, pp. 361-371, 2017.

Broos, et al., "Non-invasive assessment of murine PD-L1 levels in syngeneic tumor models by nuclear imaging with nanobody tracers", Oncotarget, vol. 8, No. 26, pp. 41932-41946, 2017.

Brown, et al., "Blockade of Programmed Death-1 Ligands on Dendritic Cell Enhances T Cell Activation and Cytokine Production", The Journal of Immunology, vol. 170, pp. 1257-1266, 2003.

Callahan, et al., "At the Bedside: CTLA-4 and PD-1-blocking antibodies in cancer immunotherapy", Journal of Leukocyte Biology, vol. 1, pp. 41-53, 2013.

Cartwright, et al., "The immune synapse clears and excludes molecules above a size threshold", Nature Communications Article, pp. 1-12, Nov. 19, 2014.

Chakravarty, et al., "Nanobody: The "Magic Bullet" for Molecular Imaging?", IvySpring, Theranostics, vol. 4, Issue 1, pp. 386-398, 2014.

Chatterjee, et al., "Rapid PD-L1 detection in tumors with PET using a highly specific peptide", HHS Public Access, Author Manuscript, vol. 483, pp. 258-263, Jan. 29, 2017.

Donnelly, et al., "Synthesis and Biologic Evaluation of a Novel $^{18}$F-Labeled Adnectin as a PET Radioligand for Imaging PD-L1 Expression", Society of Nuclear Medicine and Molecular Imaging, pp. 529-536, 2018.

England, et al., "$^{89}$Zr-labeled nivolumab for imaging of T-cell infiltration in a humanized murine model of lung cancer", European Journal Nucl Med Imaging, vol. 45, pp. 110-120, Jan. 2018.

Ge, et al., "Blockade of PD-1/PD-L1 immune checkpoint during DC vaccination induces potent protective immunity against breast cancer in hu-SCID mice", Cancer Letters, vol. 336, pp. 253-259, 2013.

Gong, et al., "Development of PD-1 and PD-L1 inhibitors as a form of apy: a comprehensive review of registration trials and future considerations", Journal of ImmunoTherapy Cancer, pp. 1-18, 2018.

Gong, et al., "Radiation therapy and PD-1/PD-L1 blockade: the clinical development of an evolving anticancer combination", Journal of ImmunoTherapy of Cancer, pp. 1-17, 2018.

Gonzalez, et al., "In Vivo Imaging of the Programmed Death Ligand 1 by $^{18}$F PET", Journal of Nucl Med., vol. 58, No. 11, pp. 1852-1857, 2017.

Goyvaerts, et al., "Development of the Nanobody display technology to target lentiviral vectors to antigen-presenting cells", Gene Therapy, pp. 1-8, 2012.

Goyvaerts, et al., "Targeting of Human Antigen-Presenting Cell Subsets", Journal of Virology, vol. 87, No. 20, pp. 11304-11308, Oct. 2013.

Grenga, et al., "A fully human IgG1 anti-PD-L1 MAb in an in vitro assay enhances antigen-specific T-cell responses", Clinical & Translational Immunology, pp. 1-12, 2016.

Hamers, et al., "Naturally occurring antibodies devoid of light chains", Letters to Nature, vol. 363, pp. 446-448, Jun. 3, 1993.

Hawkins, et al., "Selection of Phage Antibodies by Binding Affinity", Journal of Molecular Biology, vol. 226, pp. 889-896, 1992.

He, et al., "Blockade of B7-H1 with sPD-1 Improves Immunity against Murine Hepatocarcinoma", Anticancer Research, vol. 25, pp. 3309-3314, 2005.

Hobo, et al., "siRNA silencing of PD-L1 and PD-L2 on dendritic cells augments expansion and function of minor histocompatibility antigen-specific CD8+ T cells", Immunobiology, vol. 116, No. 22, pp. 4501-4511, Nov. 2010.

Holt, et al., "Domain antibodies: proteins for therapy", TRENDS in Biotechnology, vol. 21, No. 11, pp. 484-490, Nov. 2003.

Jackson, et al., "In vitro antibody maturation. Improvement of a high affinity, neutralizing antibody against IL-1 beta", The Journal of Immunology, vol. 154, pp. 3310-3319, 1995.

Karwacz, et al., "PD-L1 co-stimulation contributes to ligand-induced T cell receptor down-modulation on CD8+ T cells", EMBO Molecular Medicine, vol. 3, pp. 581-592, 2011.

Keyaerts, et al., "Phase I Study of $^{68}$Ga-HER2-Nanobody for PET/CT Assessment of HER2 Expression in Breast Carcinoma", Journal of Nucl Medicine, vol. 57, pp. 27-33, 2016.

Roberts, et al., "Immune checkpoint inhibitors: Navigating a new paradigm of treatment toxicities", Asia-Pacific Journal of Clinical Oncology, vol. 13, pp. 277-288, 2017.

Lemaire, et al., "Imaging and radioimmunotherapy of multiple myeloma with anti-idiotypic Nanobodies", Leukemia, vol. 28, pp. 444-447, 2014.

Lesniak, et al., "PD-L1 Detection in Tumors Using [$^{64}$]Atezolizumab with PET", Public Access, Bioconjug Chem., pp. 1-18, Sep. 21, 2016.

Lichtenegger, et al., "Targeting LAG-3 and PD-1to Enhance T Cell Activation by Antigen-Presenting Cells", Frontiers in Immunology, vol. 9, Article 385, pp. 1-12, Feb. 2018.

Liechtenstein, et al., "PD-L1/PD-1 Co-Stimulation, a Brake for T cell Activation and a T cell Differentiation Signal", J. Clin. Cell immunology, pp. 1-14, Oct. 30, 2012.

Liu, et al., "Structural basis of anti_PD-L1 monoclonal antibody avelumab for tremor therapy", Cell Research, vol. 27, pp. 151-153, 2017.

Loening, et al., "AMIDE: a free software tool for multimodality medical image analysis", Molecular Imaging, vol. 2, pp. 131-137, Aug. 2003.

Maenhout, et al., "AZD1480 delays tumor growth in a melanoma model while enhancing the suppressive activity of myeloid-derived suppressor cells", Oncotarget, vol. 5, No. 16, pp. 6801-6815, 2014.

Marks, et al., "By-Passing Immunization: Building high affinity human antibodies by chain shuffling", Nature Publishing Group, vol. 10, pp. 779-783, Jul. 1992.

Massa, et al., "Emerging site-specific bioconjugation strategies for radioimmunotracer development", Expert Opinion on Drug Delivery, pp. 1-16, 2016.

Maute, et al., "Engineering high-affinity PD-1 variants for optimized immunotherapy and immuno-PET imaging", CrossMark, pp. 1-9, Nov. 10, 2015.

Merrick, et al., "Autologous versus allogeneic peptide-pulsed dendritic cells for anti-tumour vaccination: expression of allogeneic MHC supports activation of antigen specific T cells, but impairs early naive cytotoxic priming and anti-tumour therapy", Cancer Immunol Immunother, vol. 57, pp. 897-906, Jun. 2008.

(56) References Cited

OTHER PUBLICATIONS

Niemeijer, et al., "whole body PD-1 and PD-L1 positron emission tomography in patients with non-small-cell lung cancer", Nature Communication, pp. 1-5, 2018.
Page, et al., "Immune Modulation in Cancer with Antibodies", Annu. Rev. Med., pp. 185-202, 2014.
Pen, et al., "Interference with PD-L1/PD-1 co-stimulation during antigen presentation enhances the multifunctionality of antigen-specific T cells", Gene Therapy, vol. 21, pp. 262-271, 2014.
Put, et al., "SPECT Imaging of Joint Inflammation with Nanobodies Targeting the Macrophage Mannose receptor in a Mouse Model for Rheumatoid Arthritis", The Journal of Nuclear Medicine, vol. 54, pp. 807-814, 2013.
Qu, et al., "Monocyte-derived dendritic cells: targets as potent antigen-presenting cells for the design of vaccines against infectious diseases", International Journal of Infectious Diseases, vol. 19, pp. 1-5, 2014.
Ribas, et al., "PD-1 Blockade Expands Intratumoral Memory T Cells", Cancer Immunology Research, pp. 194-204, Mar. 2016.
Santos, et al., "Dendritic Cell-Based Cancer Vaccines", J. Immunol., vol. 200, 443-449, Jan. 15, 2018.
Schats, et al., "Optimal Evaluatation of Programmed Death Ligan-1 on Tumor Cells Versus Immune Cells Requires Different Detection Methods", Arch pathol Lab Med., vol. 142, pp. 982-991, Aug. 2018.
Schier, et al., "Identification of functional and structural amino-acid residues by parsimonious", Gene, vol. 169, pp. 147-155, 1996.
Tan, et al., "Distinct PD-L1 binding characteristics of therapeutic monoclonal antibody durvalumab", Protein & Cell, vol. 9, pp. 135-139, 2018.
Tuyaerts, et al., "Generation of large numbers of dendritic cells in a closed system using Cell Factories", Journal of Immunological Methods, vol. 264, pp. 135-151, 2002.
Van Der Jeught, et al., "Dendritic Cell Targeting mRNA Lipopolyplexes Combine Strong Antitumor T-Cell Immunity with Improved Inflammatory Safety", American Chemical Society, vol. 12, pp. 9815-9829, 2018.
Van Hoecke, et al., "Treatment with mRNA coding for the necroptosis mediator MLKL induces antitumor immunity directed against neoepitopes", Nature Communications, pp. 1-17, 2018.
Van Lint, et al., "Preclinical Evaluation of TriMix and Antigen mRNA-Based Antitumor Therapy", Microenvironment and Immunology, pp. 1661-1672, 2012.
Van Lint, et al., "Intratumoral Delivery of TriMix mRNA Results in T-cell Activation by cross-Presenting Dendritic Cells", Cancer Immunology Research, vol. 4, pp. 146-157, Feb. 2016.
Vaneycken, et al., "Preclinical screening of anti-HER2 nanobodies for molecular imaging of breast cancer", The FASEB Journal, Research Communication, vol. 25, pp. 2433-2446, Jul. 2011.
Vanhove, et al., "Improved quantification in single-pinhole and multiple-pinhole SPECT using micro-CT information", Eur. Journal Nucl. Medical Mol. Imaging, vol. 36, pp. 1049-1063, 2009.
Verbeke, et al., "Broadening the Message: A Nanovaccine Co-loaded with Messenger RNA and α-GalCer Induces Antitumor Immunity through Conventional and Natural Killer T Cells", vol. 13, pp. 1655-1669, 2019.
Versteven, et al., "A versatile T cell-based assay to assess therapeutic antigen-specific PD-1-targeted approaches", Oncotarget, vol. 9, No. 45, pp. 27797-27808, 2018.
Ward, et al., "Binding activities of a repertoire of single immunoglobulin variable domains secreted from *Escherichia coli*", Letters to Nature, vol. 341, pp. 544-547, Oct. 12, 2989.
Wilgenhof, et al., "A phase IB on intrvenous synthetic mRNA electroporated dendritic cell immunotherapy in pretreated advanced melanoma patients", Annals of Oncology, vol. 24, pp. 2686-2693, 2013.
Zhang, et al., "Structural basis of a novel PD-L1 nanobody for immune checkpoint blockade", Citation:Cell Discovery, vol. 3, pp. 1-12, 2017.
Zou, et al., "PD-L1 (B7-H1) and PD-1 Pathway Blockade for Cancer Therapy: Mechanisms, Response Biomarkers and Combinations", Sci Transl Med., vol. 8, pp. 1-34, Mar. 2, 2016.
Xavier, et al., "Synthesis, Preclinical Validation, Dosimetry, and Toxicity of $^{68}$Ga-NOTA-Anti-HER2 Nanobodies for PET Imaging of HER2 Receptor Expression in Cancer", The Journal of Nuclear Medicine, vol. 54, No. 5, pp. 776-784, May 2013.
Xavier, et al., "Clinical Translation of [$^{68}$Ga-NOTA-anti-MMR-sdAb for PET/CT Imaging of Protumorigenic Macrophages", Molecular Imaging and Biology, pp. 1-9, Jan. 2019.
Yelton, et al., "Affinity maturation of the BR96 anti-carcinoma antibody by codon-based mutagenesis", The Journal of Immunology, vol. 155, pp. 1994-2004, 1995.
Yokosuka, et al., "Programmed cell death 1 forms negative costimulatory microclusters that directly inhibit T cell receptor signaling by recruiting phosphatase SHP2", The Journal of Experimental Medicine, vol. 209, No. 6, pp. 1201-1217, 2012.

Amino acid sequence of IVD K1
QVQLQESGGGLVQPGGSLRLSCAASGFTFSSYAMSWVRQAPGKTLEWVSDINTGGDTSDYADSVKG
RFTISRDNAKNIVYLQMNSLKAEDTAVYYCANVPKELVLSFGSWGQGTQVTVSS (SEQ ID
NO:1)
Amino acid sequence of CDR1 of IVD K1 as determined with IMTG:
GFTFSSYA (SEQ ID NO:2)
Amino acid sequence of CDR2 of IVD K1 as determined with IMTG:
INTGGDTS (SEQ ID NO:3)
Amino acid sequence of CDR3 of IVD K1 as determined with IMTG:
ANVPKELVLSFGS (SEQ ID NO:4)

Amino acid sequence of IVD K2
QVQLQESGGGLVQPGGSLRLSCAASGFTFSSFAMSWVRQAPGKGLEWVSDIDTTGRTDYADSVKG
RFTISRDNAENTLYLQMNDLKPEDTAVYYCANVPKELVLSFGSWGPGTQVTVSS (SEQ ID
NO:5)
Amino acid sequence of CDR1 of IVD K2 as determined with IMTG:
GFTFSSFA (SEQ ID NO:6)
Amino acid sequence of CDR2 of IVD K2 as determined with IMTG:
IDTTGRTT (SEQ ID NO:7)
Amino acid sequence of CDR3 of IVD K2 as determined with IMTG:
ANVPKELVLSFGS (SEQ ID NO:4)

Amino acid sequence of IVD K3
QVQLQESGGGSVQPGGSLRLSCEASGFTFSSYAMSWVRQAPGEGLEWVSDINTGGDNTDYAGSVKG
RFTISRDNAKNTLYLQMDSLKPEDTAKYYCANVPKELVHSFNSWGQGTQVTVSS (SEQ ID
NO:8)
Amino acid sequence of CDR1 of IVD K3 as determined with IMTG:
GFTFSSYA (SEQ ID NO:2)
Amino acid sequence of CDR2 of IVD K3 as determined with IMTG:
INTGGDNT (SEQ ID NO:9)
Amino acid sequence of CDR3 of IVD K3 as determined with IMTG:
ANVPKELVHSFNS (SEQ ID NO:10)

Amino acid sequence of IVD K4
QVQLQESGGGLVQPGGSLRLSCAASGFTFSSFAMSWVRQVPGRTLEWVSDINTGGDSTDYANSVKG
RFTISRDNAKNTLYLQMNSLKPDDTAVYYCANVPKELVFSFASWGRGTQVTVSS (SEQ ID
NO:11)
Amino acid sequence of CDR1 of IVD K4 as determined with IMTG:
GFTFSSFA (SEQ ID NO:6)
Amino acid sequence of CDR2 of IVD K4 as determined with IMTG:
INTGGDST (SEQ ID NO:22)
Amino acid sequence of CDR3 of IVD K4 as determined with IMTG:
ANVPKELVFSFAS (SEQ ID NO:12)

FIG. 1

```
                1         10        20        30            40         50             60
                |*********|*********|******   ***|******** *|*********|*****   ****|*****
                <------ FR1-IMGT ----------->  <CDR1-IMGT->  <- FR2-IMGT---->   <CDR2IMGT>
             K2 QVQLQESGG-GLVQPGGSLRLSCAAS     GFTF----SSFA  MSWVRQAPGKGLEWVSD   IDTT--GRTT
             K3 QVQLQESGG-GSVQPGGSLRLSCEAS     GFTF----SSYA  MSWVRQAPGEGLEWVSD   INTG--GDNT
             K4 QVQLQESGG-GLVQPGGSLRLSCAAS     GFTF----SSFA  MSWVRQVPGRTLEWVSD   INTG--GDST 70        80        90        100          110                     120
             **|*****|*****|******|  ***|*1234567654321***  |*******
             <------------- FR3 -IMGT---------------->  <-------- CDR3- IMGT----->  <FR4-IMGT->
             DYADSVK-GRFTISRDNAENTLYLQMNDLKPEDTAVYYC    ANVPKEL------------VLSFGS  WGPGTQVTVSS
             DYAGSVK-GRFTISRDNAKNTLYLQHDSLKPEDTAKYYC    ANVPKEL------------VHSFNS  WGQGTQVTVSS
             DYANSVK-GRFTISRDNAKNTLYLQMNSLKPDDTAVYYK    ANVPKEL------------VFSFAS  WGRGTQVTVSS
```

FIG. 2A

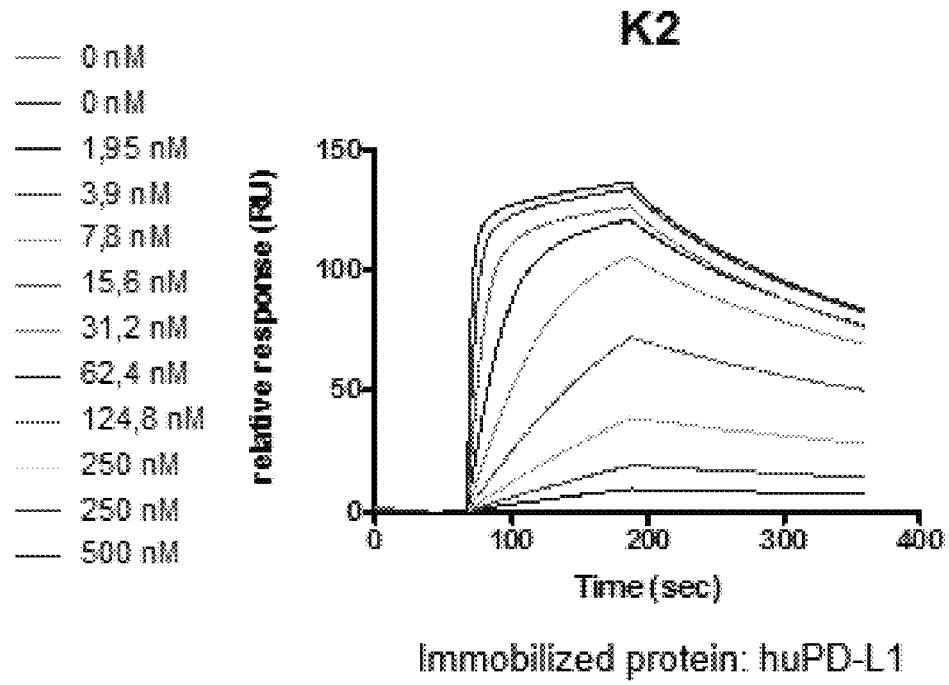

FIG. 2B

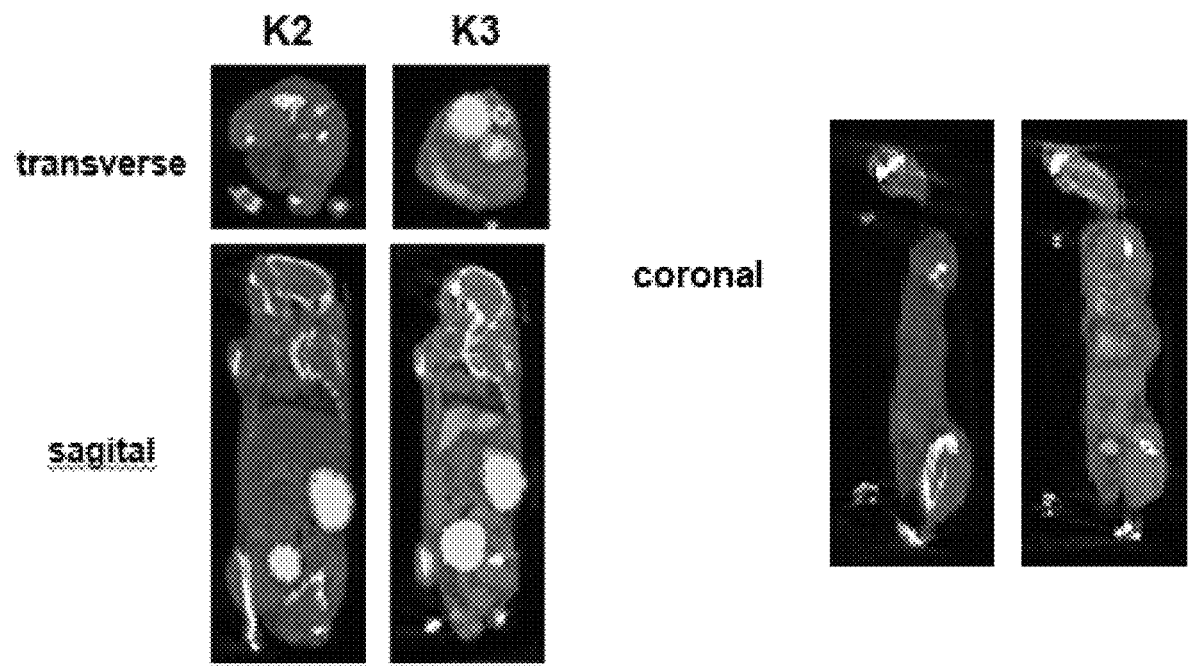
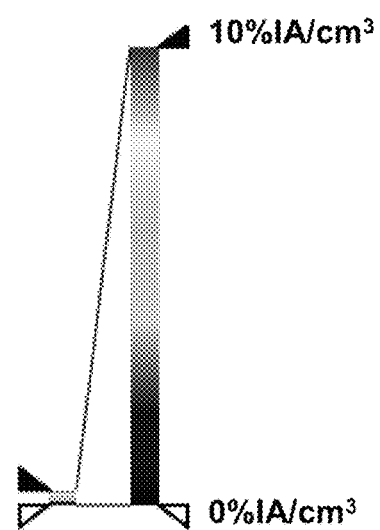
FIG. 3A

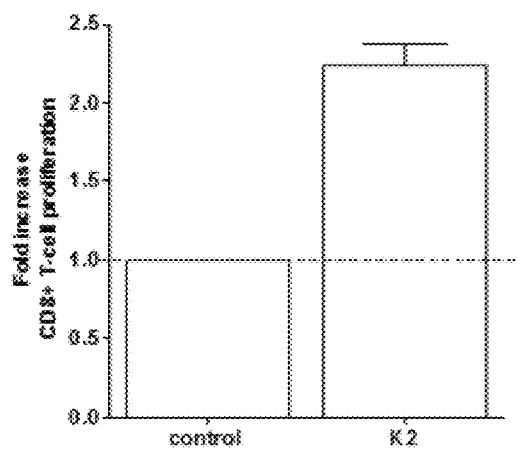
FIG. 6E
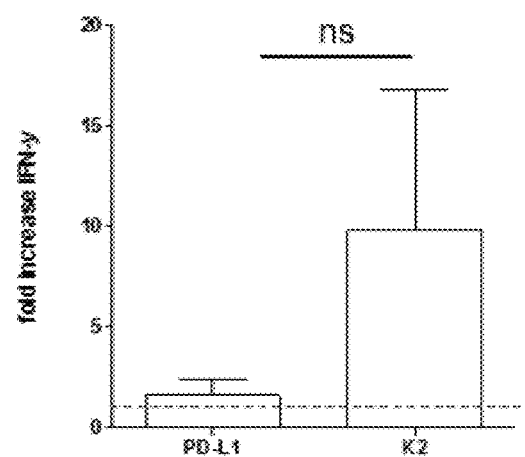
FIG. 6F
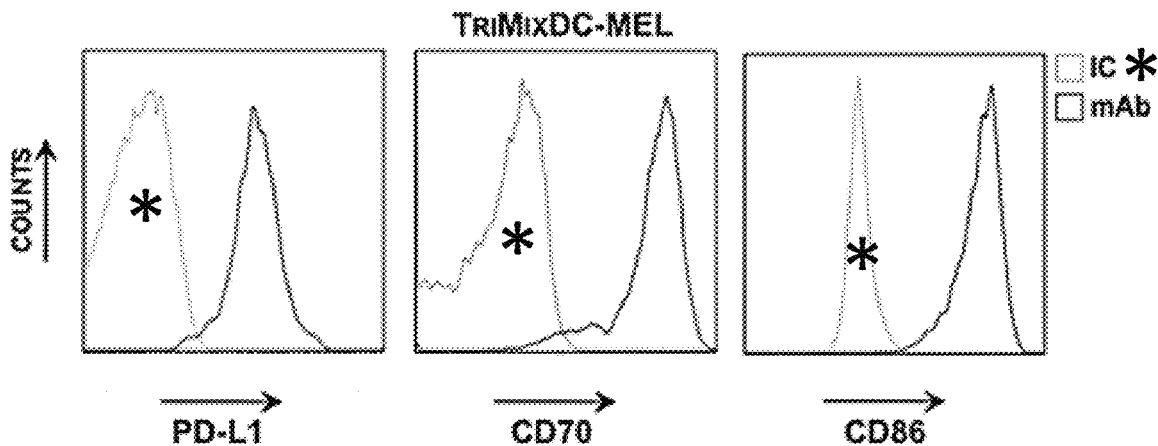
FIG. 6G
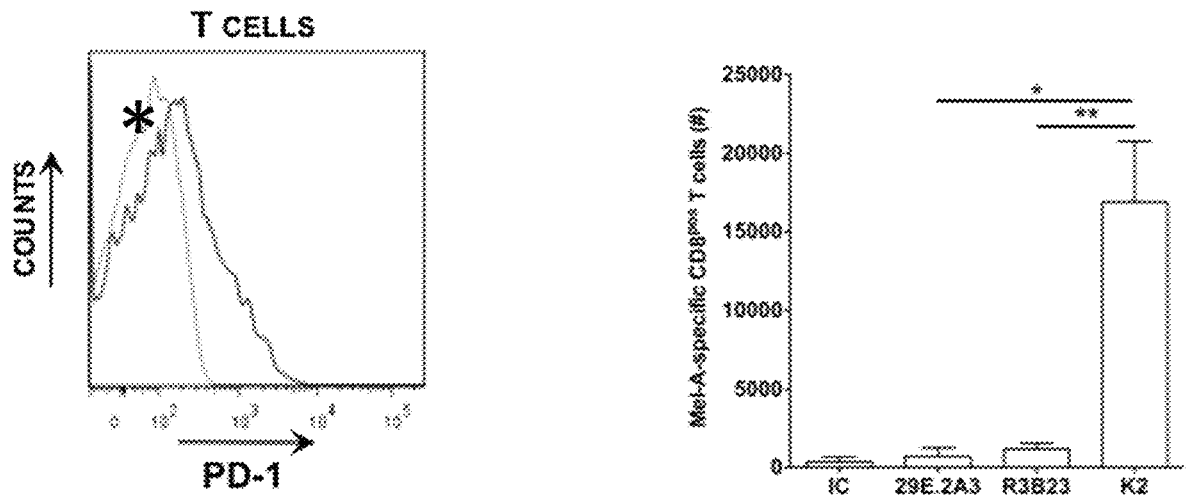
FIG. 6H
FIG. 6J

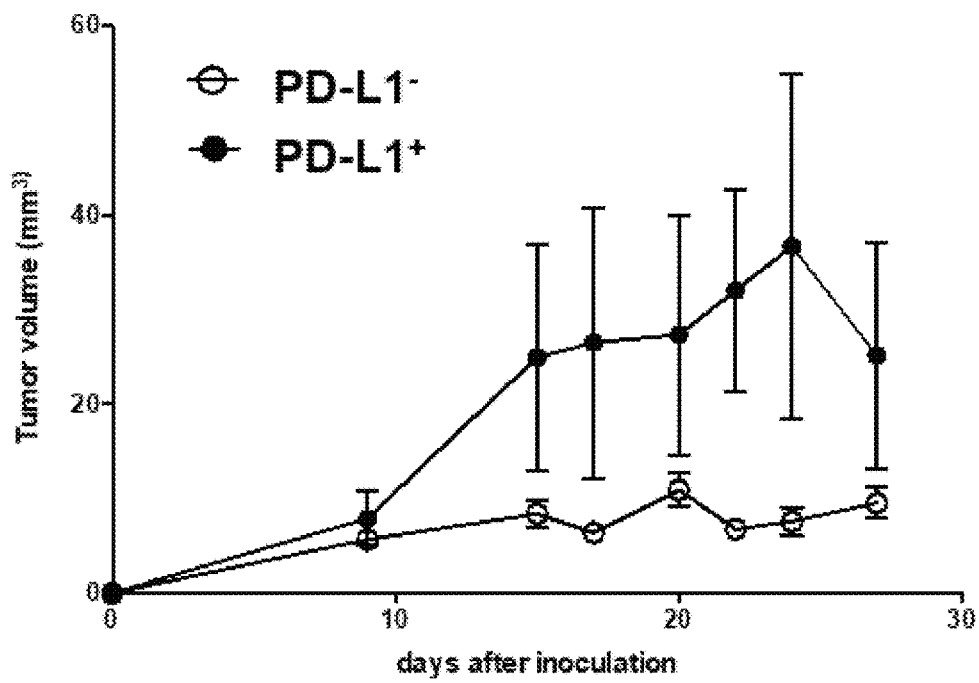
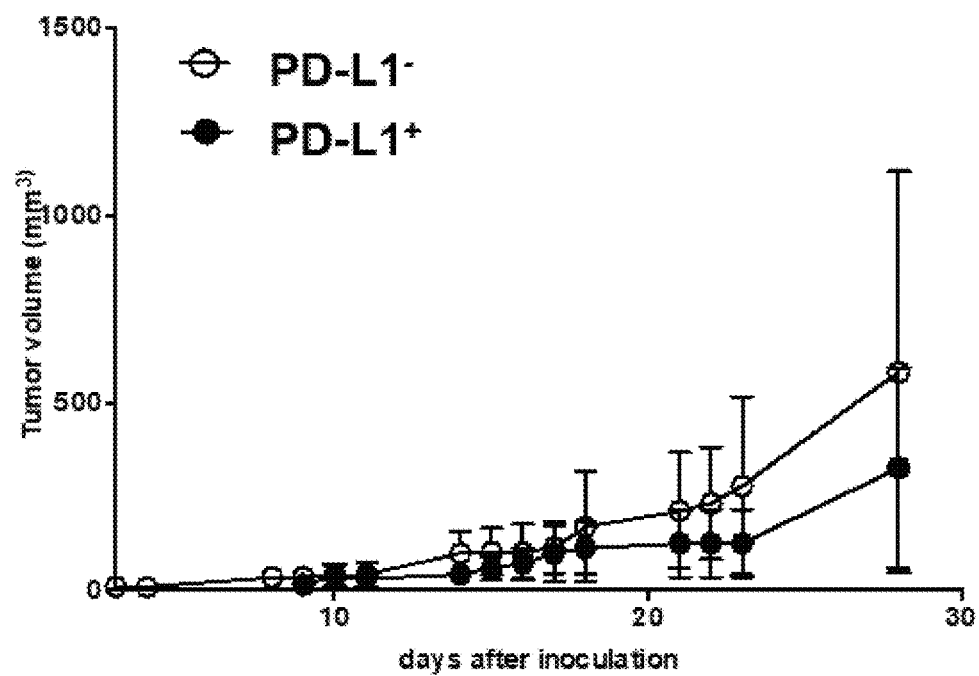
FIG. 7B

[⁶⁷Ga]Ga-NOTA-(anti-hPD-L1 sdAb K2) biodistribution & tumor targeting

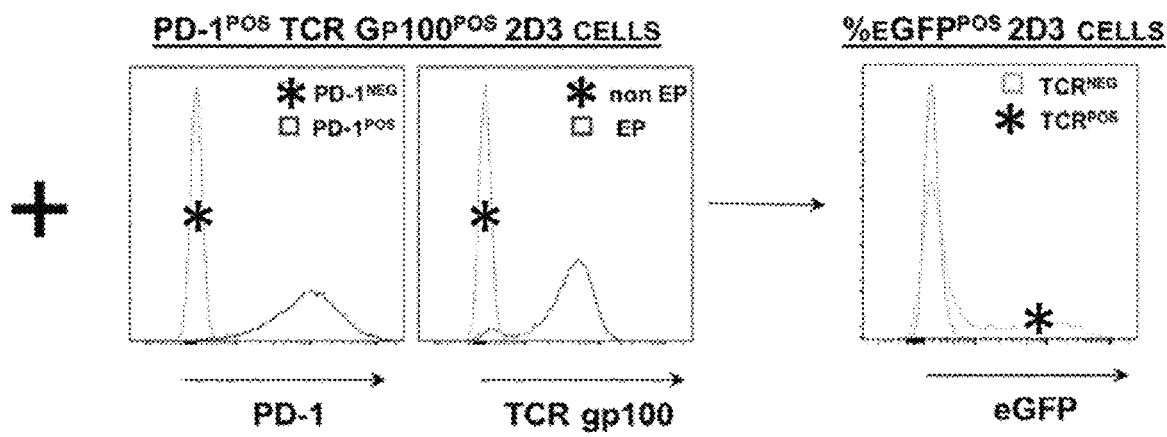
FIG. 16D
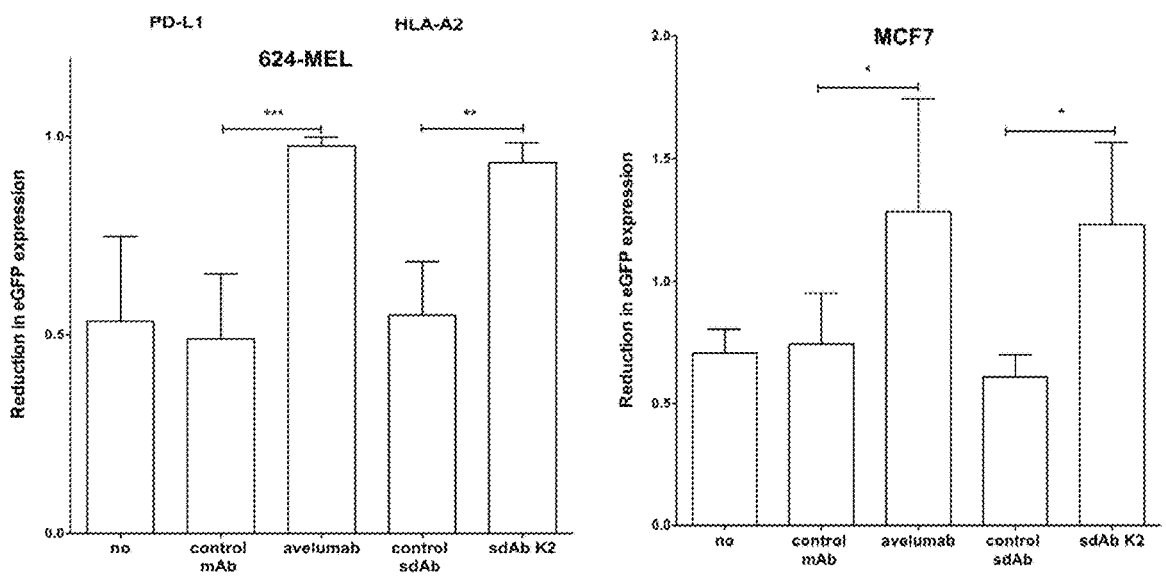
FIG. 16E
FIG. 16F

SEQUENCE LISTING

```
<160> NUMBER OF SEQ ID NOS: 22

<210> SEQ ID NO 1
<211> LENGTH: 120
<212> TYPE: PRT
<213> ORGANISM: Vicugna pacos

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Thr Leu Glu Trp Val
        35                  40                  45

Ser Asp Ile Asn Thr Gly Gly Asp Thr Ser Asp Tyr Ala Asp Ser Val
    50                  55                  60

Lys Gly Arg Phe Thr Ile Ser Arg Asp Asn Ala Lys Asn Ile Val Tyr
65                  70                  75                  80

Leu Gln Met Asn Ser Leu Lys Ala Glu Asp Thr Ala Val Tyr Tyr Cys
                85                  90                  95

Ala Asn Val Pro Lys Glu Leu Val Leu Ser Phe Gly Ser Trp Gly Gln
            100                 105                 110

Gly Thr Gln Val Thr Val Ser Ser
        115                 120

<210> SEQ ID NO 2
<211> LENGTH: 8
<212> TYPE: PRT
<213> ORGANISM: Artificial Sequence
<220> FEATURE:
```

-continued

<223> OTHER INFORMATION: huPDL1-binding polypeptide CDR1 region;
      K1K3CDR1-huPDL1Nb

<400> SEQUENCE: 2

Gly Phe Thr Phe Ser Ser Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: huPDL1-binding polypeptide CDR2 region;
      K1K4CDR2-huPDL1Nb

<400> SEQUENCE: 3

Ile Asn Thr Gly Gly Asp Thr Ser
1               5

<210> SEQ ID NO 4
<211> LENGTH: 13
<212> TYPE: PRT
<213> ORGANISM: Artificial Sequence
<220> FEATURE:
<223> OTHER INFORMATION: huPDL1-binding polypeptide CDR3 region;
      K1K2CDR3-huPDL1Nb

<400> SEQUENCE: 4

Ala Asn Val Pro Lys Glu Leu Val Leu Ser Phe Gly Ser
1               5                   10

<210> SEQ ID NO 5
<211> LENGTH: 120
<212> TYPE: PRT
<213> ORGANISM: Vicugna pacos

<400> SEQUENCE: 5

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ala Met Ser Trp Val Arg Gln Ala Pro Gly Lys Gly Leu Glu Trp Val
            35                  40                  45

Ser Asp Ile Asp Thr Thr Gly Arg Thr Thr Asp Tyr Ala Asp Ser Val
        50                  55                  60

Lys Gly Arg Phe Thr Ile Ser Arg Asp Asn Ala Glu Asn Thr Leu Tyr
65                  70                  75                  80

Leu Gln Met Asn Asp Leu Lys Pro Glu Asp Thr Ala Val Tyr Tyr Cys
                85                  90                  95

Ala Asn Val Pro Lys Glu Leu Val Leu Ser Phe Gly Ser Trp Gly Pro
            100                 105                 110

Gly Thr Gln Val Thr Val Ser Ser
        115                 120

<210> SEQ ID NO 6
<211> LENGTH: 8
<212> TYPE: PRT
<213> ORGANISM: Artificial Sequence
<220> FEATURE:
<223> OTHER INFORMATION: huPDL1-binding polypeptide CDR1 region;
      K2K4CDR1-huPDL1Nb

<400> SEQUENCE: 6

Gly Phe Thr Phe Ser Ser Phe Ala
1               5

<210> SEQ ID NO 7
<211> LENGTH: 8
<212> TYPE: PRT
<213> ORGANISM: Artificial Sequence
<220> FEATURE:
<223> OTHER INFORMATION: huPDL1-binding polypeptide CDR2 region;
      K2CDR2-huPDL1Nb

<400> SEQUENCE: 7

Ile Asp Thr Thr Gly Arg Thr Thr
1               5

<210> SEQ ID NO 8
<211> LENGTH: 120
<212> TYPE: PRT
<213> ORGANISM: Vicugna pacos

<400> SEQUENCE: 8

Gln Val Gln Leu Gln Glu Ser Gly Gly Gly Ser Val Gln Pro Gly Gly
1               5                   10                  15

Ser Leu Arg Leu Ser Cys Glu Ala Ser Gly Phe Thr Phe Ser Ser Tyr
            20                  25                  30

Ala Met Ser Trp Val Arg Gln Ala Pro Gly Glu Gly Leu Glu Trp Val
        35                  40                  45

Ser Asp Ile Asn Thr Gly Gly Asp Asn Thr Asp Tyr Ala Gly Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Thr Ala Lys Tyr Tyr Cys
                85                  90                  95

Ala Asn Val Pro Lys Glu Leu Val His Ser Phe Asn Ser Trp Gly Gln
            100                 105                 110

Gly Thr Gln Val Thr Val Ser Ser
        115                 120

<210> SEQ ID NO 9
<211> LENGTH: 8
<212> TYPE: PRT
<213> ORGANISM: Artificial Sequence
<220> FEATURE:
<223> OTHER INFORMATION: huPDL1-binding polypeptide CDR2 region;
      K3CDR2-huPDL1Nb

<400> SEQUENCE: 9

Ile Asn Thr Gly Gly Asp Asn Thr
1               5

<210> SEQ ID NO 10
<211> LENGTH: 13
<212> TYPE: PRT
<213> ORGANISM: Artificial Sequence
<220> FEATURE:
<223> OTHER INFORMATION: huPDL1-binding polypeptide CDR3 region;
      K3CDR3-huPDL1Nb

<400> SEQUENCE: 10

Ala Asn Val Pro Lys Glu Leu Val His Ser Phe Asn Ser
1               5                   10

<210> SEQ ID NO 11

```
<211> LENGTH: 120
<212> TYPE: PRT
<213> ORGANISM: Vicugna pacos

<400> SEQUENCE: 11

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Val Pro Gly Arg Thr Leu Glu Trp Val
        35                  40                  45

Ser Asp Ile Asn Thr Gly Gly Asp Ser Thr Asp Tyr Ala Asn Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Asp Asp Thr Ala Val Tyr Tyr Cys
                85                  90                  95

Ala Asn Val Pro Lys Glu Leu Val Phe Ser Phe Ala Ser Trp Gly Arg
            100                 105                 110

Gly Thr Gln Val Thr Val Ser Ser
        115                 120

<210> SEQ ID NO 12
<211> LENGTH: 13
<212> TYPE: PRT
<213> ORGANISM: Artificial Sequence
<220> FEATURE:
<223> OTHER INFORMATION: huPDL1-binding polypeptide CDR3 region;
      K4CDR3-huPDL1Nb

<400> SEQUENCE: 12

Ala Asn Val Pro Lys Glu Leu Val Phe Ser Phe Ala Ser
1               5                   10

<210> SEQ ID NO 13
<211> LENGTH: 20
<212> TYPE: DNA
<213> ORGANISM: Artificial Sequence
<220> FEATURE:
<223> OTHER INFORMATION: PD-1 Reverse Primer

<400> SEQUENCE: 13
cttctctcgc cactggaaat                                              20

<210> SEQ ID NO 14
<211> LENGTH: 18
<212> TYPE: DNA
<213> ORGANISM: Artificial Sequence
<220> FEATURE:
<223> OTHER INFORMATION: PD-1 Forward Primer

<400> SEQUENCE: 14
ccgcacgagg gacaatag                                                18

<210> SEQ ID NO 15
<211> LENGTH: 20
<212> TYPE: DNA
<213> ORGANISM: Artificial Sequence
<220> FEATURE:
<223> OTHER INFORMATION: Ppia amplification primer

<400> SEQUENCE: 15
ttcaccttcc caaagaccac                                              20
```

-continued

<210> SEQ ID NO 16
<211> LENGTH: 20
<212> TYPE: DNA
<213> ORGANISM: Artificial Sequence
<220> FEATURE:
<223> OTHER INFORMATION: Ppia amplification primer

<400> SEQUENCE: 16
caaacacaaa cggttcccag                                                 20

<210> SEQ ID NO 17
<211> LENGTH: 5
<212> TYPE: PRT
<213> ORGANISM: Artificial Sequence
<220> FEATURE:
<223> OTHER INFORMATION: Sortase amino acid substrate motif
<220> FEATURE:
<221> NAME/KEY: MISC_FEATURE
<222> LOCATION: (3)..(3)
<223> OTHER INFORMATION: Xaa can be any naturally ocurring amino acid

<400> SEQUENCE: 17

Leu Pro Xaa Thr Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Sortase amino acid substrate motif

<400> SEQUENCE: 18

Leu Pro Glu Thr Gly
1               5

<210> SEQ ID NO 19
<211> LENGTH: 10
<212> TYPE: PRT
<213> ORGANISM: Artificial Sequence
<220> FEATURE:
<223> OTHER INFORMATION: Melan-A/MART-1 HLA-A2 dextramer conjugated to
      PE

<400> SEQUENCE: 19

Glu Leu Ala Gly Ile Gly Ile Leu Thr Val
1               5                   10

<210> SEQ ID NO 20
<211> LENGTH: 9
<212> TYPE: PRT
<213> ORGANISM: Artificial Sequence
<220> FEATURE:
<223> OTHER INFORMATION: gp100 HLA-A2 dextramer conjugated to PE

<400> SEQUENCE: 20

Tyr Leu Glu Pro Gly Pro Val Thr Val
1               5

<210> SEQ ID NO 21
<211> LENGTH: 9
<212> TYPE: PRT
<213> ORGANISM: Artificial Sequence
<220> FEATURE:
<223> OTHER INFORMATION: gp100 (280-288) peptide

<400> SEQUENCE: 21

```
Tyr Leu Glu Pro Gly Pro Val Thr Ala
1               5

<210> SEQ ID NO 22
<211> LENGTH: 8
<212> TYPE: PRT
<213> ORGANISM: Artificial Sequence
<220> FEATURE:
<223> OTHER INFORMATION: huPDL1-binding polypeptide CDR2 region;
      K4CDR2-huPDL1Nb

<400> SEQUENCE: 22

Ile Asn Thr Gly Gly Asp Ser Thr
1               5
```

HUMAN PD-L1-BINDING IMMUNOGLOBULINS

CROSS REFERENCES TO RELATED APPLICATIONS

This application is a national-stage entry under 35 U.S.C. § 371 of International Application PCT/EP2019/055133, filed Mar. 1, 2019, which International Application claims the benefit of priority to European Application No. 18159388.0, filed Mar. 1, 2018, and to European Application No. 18208646.2, filed Nov. 27, 2018.

FIELD OF THE INVENTION

The invention relates to polypeptides, in particular polypeptides comprising an immunoglobulin domain, binding to human Programmed Death Ligand-1 (huPDL1) and to applications of such polypeptides such as for use as a medicament or for use as diagnostic agent, for example as an immunotracer.

SEQUENCE LISTING

Applicant incorporates by reference a CRF sequence listing having file name Substitute_Sequence_Listing_VUB0007PA.txt (8745 bytes), created on Apr. 20, 2022.

BACKGROUND

The immune checkpoint axis consisting of Programmed Death-1 (PD-1) and its ligand PD-L1 (Programmed Death Ligand-1) is a central element in the escape of cancer cells from anticancer immune responses. Monoclonal antibodies (mAbs) against PD-1 and PD-L1 have been approved for treatment of various cancer types; an overview is given in e.g. Table 1 of Gong et al. 2018 (J Immunother Cancer 6:8). Systemic administration of these mAbs is performed at high doses to ensure sufficient uptake in the tumour. This is required as mAbs have low tissue penetrating capacities, however, withholds an increased risk of immune-related side effects and toxicities (e.g. Roberts et al. 2017, Asia Pac J Clin Oncol 13:277-288). The issues of patient eligibility and monitoring as well as delivery of the PD-L1 targeting moiety to the tumour, highlight the need for tools that allow assessment of the dynamic immune checkpoint expression, and that can target PD-L1 within the tumour efficiently.

International patent application publications WO2008/071447 and WO2009/030285 both disclose a set of nanobodies raised using huPD-L1 (same set of nanobodies in both documents). In a publication by Broos et al. 2017 (Oncotarget 8:41932), the suitability of nanobodies reactive to murine PD-L1 (but not to human PD-L1) for molecular imaging was assessed. Applicability for molecular imaging of affibodies binding to human PD-L1 was discussed by Gonzalez et al. 2017 (J Nucl Med 58:1852) and further in International patent application publications WO2017/072273 and WO2017/072280. In a similar context, anti-PD-L1 adnectins (monobodies) were disclosed by Donnely et al. 2017 (J Nucl Med doi:10.2967/jnumed.117.199596), and further in International patent application publications WO2016/086021 and WO2016086036. PD-L1-binding macrocyclic peptides were designed for the same purpose (Chatterjee et al. 2017, Biochem Biophys Res Comm 483: 258; and International patent application publication WO2016/039749). Maute et al. 2015 (Proc Natl Acad Sci 112:E6506) reported an affinity engineered ectodomain PD-1 to be useful for PD-L1 imaging in vivo (see also International patent application publication WO20160229). The ectodomain of PD-1 (and PD-L1) encoded in the form of mRNA has been used in the context of dendritic cell vaccination by Pen et al. 2014 (Gene Therapy 21:262-271). Finally, a clinical trial with 99m-Tc Labelled Anti-PD-L1 VHH for diagnostic imaging of non-small cell lung cancer was reported (https://clinicaltrials.gov/ct2/show/NCT02978196).

SUMMARY OF THE INVENTION

The invention relates in one aspect to polypeptides, such as polypeptides comprising an immunoglobulin variable domain (IVD), binding to human Programmed Death Ligand-1 (huPDL1), wherein the amino acid sequence of the polypeptide is comprising a CDR1 region, a CDR2 region, and a CDR3 region, wherein the CDR1, CDR2 and CDR3 regions are selected from those CDR1, CDR2 and CDR3 regions, respectively, as present in any of SEQ ID Nos:1, 5, 8 or 11. Methods for delineating or determining CDR regions include the Kabat, Chothia, Martin, and IMTG methods. In particular, the huPDL1-binding polypeptides comprise CDR regions of any of SEQ ID Nos:1, 5, 8 or 11 as determined by the IMTG method wherein the CDR1 region is chosen from SEQ ID Nos: 2 and 6, the CDR2 region is chosen from SEQ ID Nos: 3, 7, 9, or 22, and the CDR3 region is chosen from SEQ ID Nos:4, 10, or 12. Further more specifically, the CDR regions are the CDR regions as present in SEQ ID NO:5.

In the above, the CDR regions may be humanized and/or the IVD may be humanized.

Furthermore in the above, the huPDL1-binding polypeptides may further comprise a functional moiety. Such functional moiety may e.g. be a His-tag or sortase recognition sequence, or may be a detectable moiety. In particular, the detectable moiety may be linked randomly or to a specific site comprised in the polypeptide comprising an huPDL1-binding IVD. In case of linkage to a specific site, this may for instance be, but is not limited thereto, to a His-tag or sortase recognition sequence comprised in the polypeptide comprising an huPDL1-binding IVD.

The invention also relates to isolated nucleic acids encoding an above huPDL1-binding polypeptides, to vectors comprising such nucleic acid. Further included are host cells expressing an above huPDL1-binding polypeptide, host cells comprising an above nucleic acid or comprising an above vector.

Pharmaceutical compositions comprising any of the above huPDL1-binding polypeptides are likewise part of the invention.

The above huPDL1-binding polypeptides, or the above pharmaceutical composition, find applications such as for use as a medicament, for use in diagnosis, for use in surgery, for use in treatment, for use in therapy monitoring or for use in dendritic cell vaccination, and, more specifically, for use as an imaging agent.

The invention further relates to methods for producing an above huPDL1-binding polypeptide, such methods comprising the steps of:

expressing the huPDL1-binding polypeptide in a host cell as described above; and purifying the expressed huPDL1-binding polypeptide.

In one embodiment, such methods may further comprise the coupling of a detectable moiety to the purified huPDL1-binding polypeptide.

BRIEF DESCRIPTION OF THE DRAWINGS

FIG. 1. Amino acid sequences of huPDL1-binding VHH domains and of CDR1, CDR2, and CDR3 amino acid sequences as determined by the IMTG method.

FIGS. 2A-2D. Characterizations of PD-L1 specific sdAbs. (FIG. 2A) Amino acid sequence alignment of sdAb K2 (SEQ ID NO:5), K3 (SEQ ID NO:8), and K4 (SEQ ID NO:11). The sequence includes three complementarity determining regions (CDR 1, 2, 3) and four framework regions (FR1-4, flanking the CDRs). (FIG. 2B) Representative graph showing the affinity/kinetics of purified sdAb K2 interacting with immobilized recombinant PD-L1 protein as determined in SPR. Sensograms of different concentration of the sdAbs are shown (n=1). (FIG. 2C) Representative flow cytometry graphs showing labelling of HEK293T cells versus PD-L1 expressing HEK293T cells with antibodies (mAb) specific for PD-L1 or sdAb K2. (FIG. 2D) Table summarizing the affinities (KD) of purified sdAbs K2, K3 and K4 interacting with immobilized recombinant PD-L1 protein as determined in SPR and the fold increase in mean fluorescent intensities (MFI) of the binding of sdAbs K2, K3 and K4 to human PD-L1 compared to control sdAb, as determined with flow cytometry.

FIGS. 3A-3B. (FIG. 3A) SPECT/CT images showing the biodistribution of $^{99m}$Tc-labelled sdAb K2 and K3 in healthy C57BL/6 mice (n=3). (FIG. 3B) Graph showing the ex vivo analysis of the biodistribution of sdAb K2 and K3 in organs of healthy C57BL/6 mice (expressed as % IA/g, n=3).

(FIG. 4A) SPECT/CT images showing the biodistribution of $^{99m}$Tc-labelled sdAb K2 in athymic nude mice bearing PD-L1$^-$ (left) or PD-L1$^+$ (right) 624-MEL cells (n=6). (FIG. 4B) Graph showing the accumulation of sdAb K2 in the tumours (expressed as % IA/g, n=6). (FIG. 4C) Graph depicting the expression of PD-L1 in the tumours (%) (n=6).

(FIG. 5A) Analysis of IC$_{50}$ values of purified sdAbs K2. The curves represent relative responses of different concentration of the purified sdAb in the presence of 25 nM recombinant PD-L1-Fc protein, interacting with immobilized human PD-1-Fc protein. These responses in function of the log concentration of the sdAb are fitted according to the "Log inhibitor versus response (variable lope)" model in Prism software. From these curves the sdAb concentration is calculated at which the relative response is inhibited by half (IC$_{50}$) (n=1). (FIG. 5B) First graph: representative histogram showing 2D3 or PD-1$^+$ 2D3 cells stained with an anti-PD-1 mAbs (n=6). Second graph: representative histogram showing PD-L1 expression on moDCs. Cells were stained with isotype control (IC) or an anti-PD-L1 mAbs (n=3). Third graph: representative histogram of MCF7 or PD-L1$^+$ MCF7 cells. Cells were stained with an anti-PD-L1 mAb (n=3). (FIG. 5C) Reduction in TCR-signalling in PD-1$^{pos}$ TCR$^{pos}$ versus PD-1$^{neg}$ TCR$^{pos}$ 2D3 cells when activated with antigen-presenting moDCs, calculated as [1−(% CD8$^{pos}$ eGF$^{pos}$ PD-1$^{pos}$ TCR$^{pos}$ 2D3 cells/% CD8$^{pos}$ eGF$^{pos}$ PD-1$^{neg}$ TCR$^{pos}$ 2D3 cells). The x-axis legend represents co-cultures without addition of mAbs or sdAbs [no], or with addition of isotype-matched control mAbs [IC], the anti-PD-L1 mAb [MIH1], sdAb R3B23 [R3B23] or sdAb K2 [K2]. The graph summarizes the reduction in TCR-signalling as mean±SEM [n=3]. (FIG. 5D) Percentage reduction in activity (PD-L1$^+$ versus PD-D-L1$^-$ MCF7 cells) expressed in percentage eGFP$^+$ CD8$^+$ 2 D3 cells. The graphs summarize the percentage eGFP as mean±SEM (n=3). (FIG. 5E) Graph summarizing the expression of CD40, CD80, CD83 and HLA-I on moDCs that were untreated [no], treated with sdAb R3B23 [R3B23], sdAb K2 [K2], or LPS. The graph summarizes the percentage marker expression as mean±SEM [n=2].

FIGS. 6A-6J. (FIG. 6A) Graph summarizing the mean±SEM of total Melan-A specific T cells after co-culture with TriMixDC-MEL in the presence or absence of isotype matched control (IC) or anti-PD-L1 mAbs (29E.2A3) or a sdAb R3B23 (control) or sdAb K2 (n=5). (FIG. 6B) Graph summarizing the fold increase in CD8$^+$ T-cell proliferation after co-culture with TriMixDC-MEL in the presence of a control sdAb or sdAb K2 (n=3). (FIG. 6C) Graph summarizing the fold increase in IFN-γ secretion by CD8$^+$ T cells co-cultured with TriMixDC-MEL in the presence of an isotype matched control or anti-PD-L1 mAb, or sdAb R3B23 (control) or sdAb K2 (n=2). (FIG. 6D) Graph summarizing the mean±SEM of total Melan-A specific T cells (n=4). (FIG. 6E) Graph summarizing the fold increase in proliferation by CD8$^+$ T cells co-cultured with DC-MEL in the presence of control sdAb or sdAb K2 (n=2). (FIG. 6F) Graph summarizing the fold increase in IFN-γ secretion by CD8$^+$ T cells co-cultured with DC-MEL in the presence of isotype matched control or anti-PD-L1 mAbs, or a sdAb R3B23 (control) or sdAb K2 (n=3). (FIG. 6G) Representative histogram showing expression of PD-L1, CD70 and CD86 on TriMixDC-MEL. Cells were stained with isotype control [IC] or surface marker-specific mAbs [n=3]. (FIG. 6H) Representative histogram showing PD-1 expression on CD8$^{pos}$ T cells. Cells were stained with isotype control [IC, *] or anti-PD-1 mAbs [n=3]. (FIG. 6I) Representative histogram showing expression of PD-L1, CD70 and CD86 on DC-MEL Cells were stained with isotype control [IC] or surface marker-specific mAbs [n=3]. (FIG. 6J) Graph summarizing the mean±SEM of total Melan-A-specific T cells after co-culture with DC-MEL in the presence or absence of isotype-matched control mAbs [IC], anti-PD-L1 mAbs [29E.2A3], sdAb R3B23 [R3B23] or sdAb K2 [K2] [n=4].

FIGS. 7A-7B. (FIG. 7A) Representative histogram showing the expression of PD-L1 on MCF7 (left) or 624-MEL (right), or their PD-L1 engineered counterparts using mAbs for labelling (n=3). (FIG. 7B) Graph showing the growth of PD-L1$^+$ or PD-L1$^-$ MCF7 (left) or 624-MEL (right) cells in athymic nude mice (n=12).

(FIG. 8A) SPECT/CT images showing the biodistribution of $^{99m}$Tc-labelled sdAb K2 in athymic nude mice bearing PD-L1$^-$ (left) or PD-L1$^+$ (right) MCF7 cells (n=6). (FIG. 8B) Graph showing the accumulation of sdAb K2 in the tumours (expressed as % IA/g, n=6). (FIG. 8C) Graph depicting the expression of PD-L1 in the tumours (%) (n=6).

(FIG. 9A) Phenotyping of DC-MEL and TriMixDC-MEL. Representative histograms are shown in comparison to the isotype matched antibody staining (n=3). (FIG. 9B) Representative histograms showing the phenotype of CD8$^+$ T cells stained with isotype matched control or anti-antigen antibodies (n=3). (FIG. 9C) Graph showing detection of PD-1 on CD8$^+$ T cells before and after co-culture with TriMixDC-MEL (n=3).

(FIG. 10A) Binding (as % bound activity) of site-specific $^{68}$Ga-labelled sdAb K2 (left bars of each condition) and random $^{68}$Ga-labelled sdAb K2 (right bars of each condition) to PD-L1+ cells ("positive cell line"), to PD-L1+ cells wherein PD-L1 was blocked prior to contacting with the labelled sdAbs ("blocked"), and to PD-L1− cells ("negative cell line"). (FIG. 10B) Uptake of site-specific $^{68}$Ga-labelled sdAb K2 and random $^{68}$Ga-labelled sdAb K2 in mice bearing PD-L1− ("−mel624") or PD-L1+ ("+mel624") 624-MEL cells. Depicted for each organ or for the tumour are, from left to right, bars 1 to 4, respectively. Bar 1 represents uptake values of site-specific $^{68}$Ga-labelled sdAb K2 in mice bearing PD-L1− 624-MEL cells ("site specific −mel624"); bar 2 represents uptake values of site-specific $^{68}$Ga-labelled sdAb K2 in mice bearing PD-L1+ 624-MEL cells ("site specific +mel624"); bar 3 represents uptake values of random $^{68}$Ga-labelled sdAb K2 in mice bearing PD-L1− 624-MEL cells ("random −mel624"); bar 4 represents uptake values of random $^{68}$Ga-labelled sdAb K2 in mice bearing PD-L1+ 624-MEL cells ("random +mel624"). (FIG. 10C) Uptake of site-specific $^{67}$Ga-labelled sdAb K2 in mice bearing PD-L1 positive 624-MEL cells. See Example 3.

(FIG. 12A) SPECT/CT images showing the biodistribution of 99mTc-sdAb K2 or 99mTc-R3B23 (control sdAb) 1 hour after intravenous administration in healthy C57BL/6 mice (n=3). (FIG. 12B) Ex vivo analysis of the biodistribution of 99m Tc-sdAb K2 or 99mTc-R3B23 (control sdAb) in dissected tissues and organs 80 minutes after intravenous administration in healthy C57BL/6 mice (expressed as percent injected activity per gram, % IA/g; n=3). ****p<0.0001.

(FIG. 13A) Scheme of the experimental setup. (FIG. 13B) SPECT/CT images showing the biodistribution of 99mTc-sdAb K2 or 99mTc-R3B23 (control sdAb) 1 hour after intravenous administration in nude mice bearing PD-L1NEG (left) or lentivirally transduced, PD-L1POS (right) MCF7 tumours (n=6). (FIGS. 13C,D) Ex vivo analysis of accumulation of 99mTc-labelled sdAbs in dissected PD-L1neg or PD-L1pos MCF7 tumours ((FIG. 13C), expressed as % IA/g), and of tumour-to-blood uptake ratios (FIG. 13D), 80 minutes after intravenous radiotracer injection (n=6). (FIG. 13E) Percentage of human PD-L1 and HLA-A2-expressing cells in tumours (n=6) dissected from mice that were subcutaneously implanted with either parental MCF7 cells (PD-L1neg) or human PD-L1-transduced counterparts (PD-L1pos), as measured by flow cytometry analysis of tumour single cell dissociates. p<0.01; **p<0.0001.

(FIG. 14A) Scheme of the experimental setup. (FIG. 14B) SPECT/CT images showing the biodistribution of 99mTc-sdAb K2 or 99mTc-R3B23 (control sdAb) 1 hour after intravenous administration in nude mice bearing PD-L1NEG (left) or lentivirally transduced, PD-L1pos (right) 624-MEL tumours (n=6). (FIGS. 14C,D) Ex vivo analysis of accumulation of 99mTc labelled sdAbs in dissected PD-L1neg or PD-L1pos 624-MEL tumours ((FIG. 14C), expressed as % IA/g), and of tumour-to-blood uptake ratio (FIG. 14D), 80 minutes after intravenous radiotracer injection (n=6). (FIG. 14E) Percentage of human PD-L1 and HLA A2-expressing cells in tumours (n=6) dissected from mice that were subcutaneously implanted with either parental 624-MEL cells (PD-L1neg) or human PD-L1-transduced counterparts (PD-L1pos), as measured by flow cytometry analysis of tumour single cell dissociates. p<0.01; *p<0.001; ****p<0.0001.

(FIG. 15A) Representative histogram showing PD-L1 expression after in vitro stimulation of 938-MEL cells with 100 IU/mL recombinant human IFN-γ or non-treated 938-MEL cells, as evaluated by flow cytometry analysis. (FIG. 15B) Scheme of the experimental setup. (FIG. 15C) Representative SPECT/CT images 1 hour after intravenous administration of 99mTc-sdAb K2 in athymic nude mice bearing PD-L1 NEG 938-MEL tumours that were injected intratumourally with either PBS (left) or human IFN-γ (right) (n=4). (FIG. 15D) Accumulation of 99mTc-sdAb K2 in 938-MEL tumours (expressed as % IA/g, n=4) that were treated intratumourally with either PBS or IFN-γ, as determined by γ-counting of dissected tumours 80 minutes after radiotracer injection. (FIG. 15E) Human PD-L1 expression levels in 938-MEL tumours (n=4) treated intratumourally with either PBS or IFN-γ. PD-L1 expression was evaluated by flow cytometry analysis of dissected and dissociated tumours. PD-L1 levels were depicted as fold-increase in mean fluorescence intensity (MFI) as compared to isotype control staining. *p<0.05.

FIGS. 16A-16F. sdAb K2 and mAb avelumab antagonize PD-1:PD-L1 interactions at the protein and cellular level. (FIG. 16A) Competition studies with equimolar amounts of avelumab and sdAb K2 show that both bind the same epitope on human PD-L1, as determined by SPR. 1: sdAb K2; 2: sdAb K2+ avelumab; 3: avelumab+sdAb K2; 4: avelumab; dashed vertical line: addition of competitor. (FIG. 16B) Dose-response curves of soluble recombinant human PD-L1 protein, mixed with increasing concentrations of sdAb K2, control sdAb, avelumab or control mAb, to immobilized human PD-1 recombinant protein, as determined by SPR. Per condition, maximal RU signal is shown, relative to the sample that only contains recombinant PD-L1 protein. A representative experiment of 2 similar experiments is shown. (FIGS. 16C,D) Schematic representation of the experimental set up of the PD-1$_{POS}$ 2D3 reporter assay. (FIG. 16C) Representative flow cytometry histograms showing human PD-L1 and HLA-A2 expression in parental (PD-L1$_{NEG}$) or lentivirally-transduced, PD-L1$_{POS}$ HLA-A2POS 624-MEL or MCF7 cells that are pulsed with a gp100 peptide. (FIG. 16D) Representative flow cytometry histogram showing parental 2D3 cells or PD-1$_{POS}$ 2D3 cells, electroporated with mRNA encoding a TCR recognizing gp100. 2D3 cells were transduced with lentiviral vectors harbouring human PD-1. When the specific TCR is triggered, 2D3 cells express eGFP under the control of a NFAT promoter (right). (FIGS. 16E,F) Both avelumab and sdAb K2 revert the suppressive effect of PD-L1 on 624-MEL cells (FIG. 16E) or on MCF7 cells (FIG. 16F) on the activation of PD-1 pos 2D3 reporter cells in an antigen-specific manner. The graphs depict the reduction in eGFP expression when PD-1POS 2D3 cells are co-cultured with PD-L1POS cells compared to their co-culture with PD-L1NEG cells, as mean±SEM (n=3). No treatment, a control sdAb or an isotype control mAb served as a negative control. Percentage eGFP-positive CD8pos PD-1pos 2D3 cells was evaluated using flow cytometry. *p<0.05; p<0.01; *p<0.001.

(FIGS. 17A-C) Schematic representation of the experimental set up. (FIG. 17A) Graph bars showing percentage PD-1 or PD-L1-expressing $CD8_{POS}$ PBMCs (mean±SEM) either or not stimulated with anti-CD3 mAb and IL-2. (FIG. 17B) Representative histograms showing PD-L1, HLA-A2 and eGFP levels on $HLA-A2_{POS}$ 624-MEL cells that are lentiviral transduced with vectors encoding human PD-L1 and eGFP (n=3). (FIG. 17C) Total Green object area (µm2/well) of tumour cells, a measure of healthy cancer cells, was followed up every hour for 7 constitutive days using the incuCyte device. (FIG. 17D-G) Graphs showing relative response to treatment with anti-PD-L1 compounds in the 3D spheroid tumour cell cytotoxicity assay (n=3). The total green object area of $PD-L1_{POS}$ tumour cell spheroids was measured over time upon co-culture with stimulated PBMCs and in the presence of 3.6 µM anti-PD-L1 or control mAbs or sdAbs, or both. Data were normalized to the condition where no compounds were added. (FIG. 17D) Avelumab versus isotype control mAb, both added ab initio. (FIG. 17E) sdAb K2 versus control sdAb, both added ab initio. (FIG. 17F) A mixture of sdAb K2 and avelumab versus a mixture of control sdAb and isotype control mAb, all added ab initio. (FIG. 17G) Identical assay as in (FIG. 17E), except that fresh sdAbs were added every 24 hours (indicated with arrows above X-axis).

DETAILED DESCRIPTION TO THE INVENTION

Figures 2C, 2D:
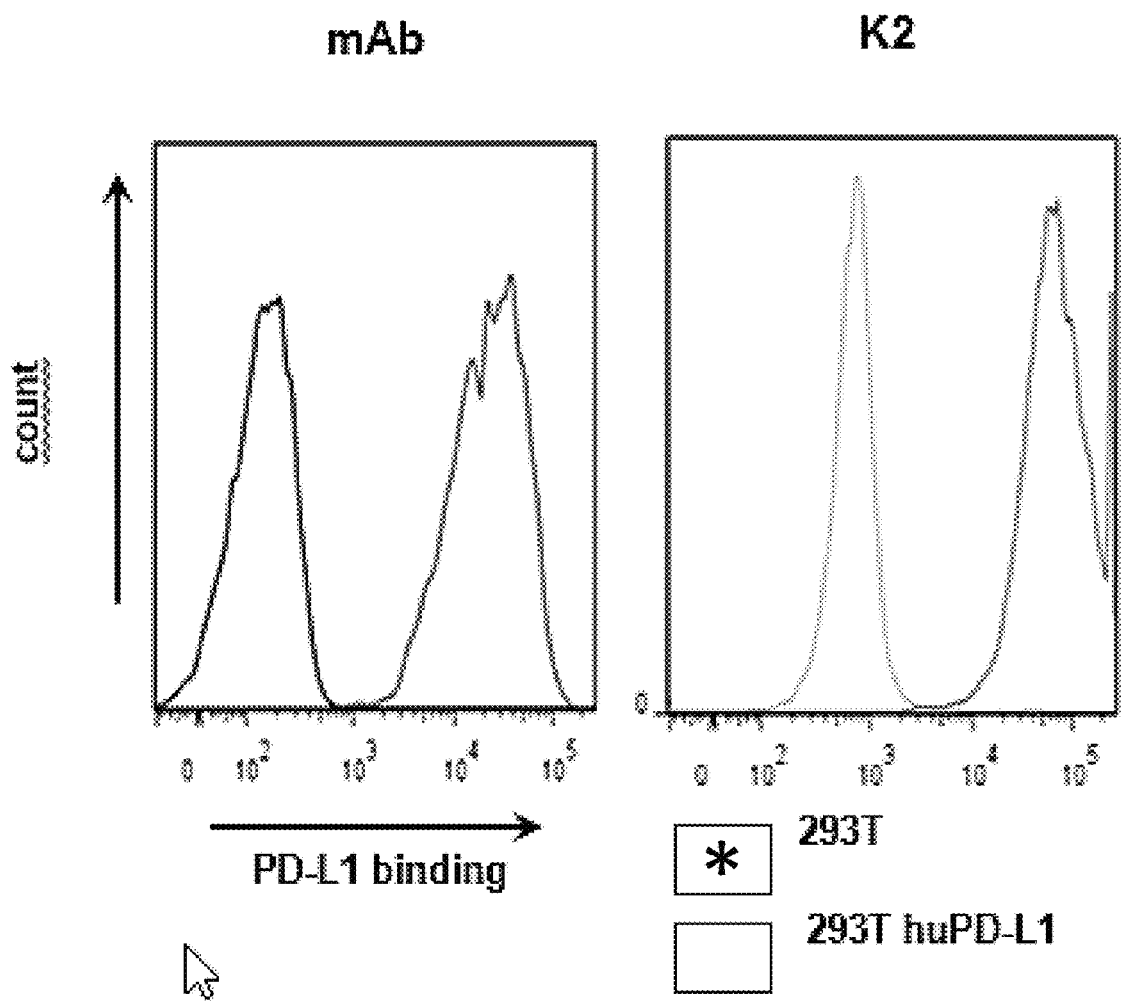

For purposes of diagnostic or molecular imaging in vivo as well as for therapeutic purposes, the imaging agent or therapeutic agent must be able to arrive at its target with high efficiency. This requires a combination of small-enough size in order to be able to achieve sufficient tissue penetration, selective binding to the target in order to achieve a high signal/noise ratio at the target site (applies especially to imaging agent but likewise contributes to the specificity of a therapeutic agent), and low overall body retention or accumulation (as a consequence of elimination from the body; typically in liver or kidneys; and all the more problematic with small-sized imaging agent) to avoid sites of high background signal which negatively influence signals at the target site (imaging agents) or to avoid potential unwanted side effects (therapeutic agents).

In work leading to the current invention, first of all a number of immunoglobulin single variable domain (ISVD) molecules, herein also referred to a single domain antibodies (sdAb), binding with high specificity to human PD-L1 (huPDL1) were identified. Surprisingly, and in contrast to similar ISVD molecules binding to murine (but not human) PD-L1, in contrast to other control ISVD molecules, and in contrast to other small-molecule PD-L1 imaging agents, the huPDL1-binding ISVDs were characterized by an extremely low renal retention whilst providing an excellent target signal/background ratio in vivo.

Anti-PD-L1 sdAbs were identified after screening of alpaca immune libraries and were evaluated for binding and affinity using enzyme-linked immunosorbent assay (ELISA), flow cytometry and Surface Plasmon Resonance (SPR). Single photon emission computed tomography imaging in mice following intravenous injection of Technetium-99m (99mTc)-labelled anti-PD-L1 sdAb revealed that this sdAb has several properties to make it an interesting diagnostic, including (i) high signal to noise ratio's; (ii) strong ability to specifically detect human PD-L1 in melanoma and breast tumours, and (iii) relatively low kidney retention, which is unique as typically radiometal-labelled sdAbs show high retention in the proximal tubuli. Moreover, we showed using SPR that the anti-PD-L1 sdAb binds to the same epitope on PD-L1 as the FDA-approved mAb avelumab, and that the anti-PD-L1 sdAb efficiently antagonizes the PD-1:PD-L1 interaction. Different in vitro human cell-based assays corroborated the PD-1:PD-L1 blocking activity, showing enhanced antigen-specific T-cell receptor signalling and tumour cell killing ability of PD-1-expressing T cells interacting with PD-L1-positive tumour cells; as well as showing enhancement of the capacity of dendritic cells (DCs) to stimulate T-cell activation and cytokine production, opening an avenue to include these anti-PD-L1 ISVDs in DC-vaccination protocols. These combined characteristics render the identified huPDL1-binding ISVDs extremely well-suited as diagnostic agent, e.g. for molecular imaging, besides being useful in therapies implying immune checkpoint inhibitors.

Based hereon, the invention is defined in the following aspects and embodiments, and described in more detail hereafter. As the invention relates to polypeptides comprising complementarity determining regions (CDRs), some explanation is first provided on how such CDRs are determined.

The determination of the CDR regions in an antibody/immunoglobulin sequence generally depends on the algorithm/methodology applied (Kabat-, Chothia-, Martin (enhanced Chothia), IMGT (ImMunoGeneTics information system)-numbering schemes; see, e.g. http://www.bioinf.org.Uk/abs/index.html#kabatnum and http://www.imgt.org/IMGTScientificChart/Numbering/IMGTnumbering.html). Applying different methods to the same antibody/immunoglobulin sequence may give rise to different CDR amino acid sequences wherein the differences may reside in CDR sequence length and/or—delineation within the antibody/immunoglobulin/IVD sequence. The CDRs of the huPDL1-binding polypeptides of the invention can therefore be described as the CDR sequences as present in the single variable domain anti-human PD-L1 antibodies characterized herein, or alternatively as determined or delineated according to a well-known methodology such as according to the Kabat-, Chothia-, Martin (enhanced Chothia), or IMGT-numbering scheme or -method. The CDR sequences defined in SEQ ID NOs: 2-4, 6-7, 9-10, and 12, for instance, have, been delineated from the anti-human PD-L1 single domain antibodies defined by SEQ ID NOs: 1, 5, 8 and 11 by means of the IMGT-method (see FIG. 1). Applying another method may result in CDR sequences (slightly) different from those defined in SEQ ID NOs: 2-4, 6-7, 9-10, and 12.

In a first aspect, the invention relates to polypeptides specifically binding to human PD-L1, wherein the amino acid sequence of the polypeptide is comprising a CDR1 region, a CDR2 region, and a CDR3 region, wherein the CDR1, CDR2 and CDR3 regions are selected from those CDR1, CDR2 and CDR3 regions, respectively, as present in any of huPDL1-binding single domain antibodies defined by SEQ ID Nos:1, 5, 8 or 11.

In particular, the polypeptides specifically binding to human PD-L1 comprise an immunoglobulin variable domain (IVD) conveying specificity of the polypeptide for binding to human PD-L1 wherein the IVD is comprising a CDR1 region, a CDR2 region, and a CDR3 region, wherein the CDR1, CDR2 and CDR3 regions are selected from those CDR1, CDR2 and CDR3 regions, respectively, as present in any of huPDL1-binding single domain antibodies defined by SEQ ID Nos:1, 5, 8 or 11 (see FIG. 1).

In an embodiment thereto, the CDR regions are determined by applying the Kabat, Chothia, Martin, or IMTG method to SEQ ID Nos:1, 5, 8 or 11. In a more specific embodiment, the CDR regions are determined by the IMTG method and further defined as a CDR1 region chosen from SEQ ID Nos: 2 and 6, a CDR2 region chosen from SEQ ID Nos: 3, 7, 9, or 22, and a CDR3 region chosen from SEQ ID Nos:4, 10, or 12. Given the high degree of similarity between individual CDR1 amino acid sequences, between individual CDR2 amino acid sequences, and between individual CDR3 amino acid sequences, any huPDL1-binding polypeptide comprising any possible combination of CDR1-CDR2-CDR3 amino acid sequences (determined with any of the above-described methods) is herewith envisaged (e.g. for the IMTG-delineated CDRs: CDR1-CDR2-CDR3 with respectively SEQ ID Nos:2-3-4, or 6-7-4, or 2-9-10, or 6-3-12, or 2-7-4, or 2-9-12, or 6-9-10, and so on, to list only a few). In one embodiment, the CDR regions are the CDR regions as present in SEQ ID NO:5, or, alternatively, as defined by IMTG as SEQ ID Nos:6, 7, and 4 for CDR1, CDR2, and CDR3, respectively.

In any of the above, the CDR regions and/or the IVD may be humanized. Humanized CDRs and/or IVDs can be obtained in any suitable manner known and thus are not strictly limited to polypeptides that have been obtained using a polypeptide that comprises a naturally occurring VHH domain as starting material. Humanized immunoglobulin single variable domains, may have several advantages, such as a reduced immunogenicity, compared to the corresponding naturally occurring VHH domains. Such humanization generally involves replacing one or more amino acid residues in the sequence of a naturally occurring CDR and/or framework region (FR) with the amino acid residues that occur at the same position in a human VH domain, such as a human VH3 domain. The humanizing substitutions should be chosen such that the resulting humanized immunoglobulin domains still retain the favourable properties of the originator immunoglobulin (or further improved by e.g. affinity maturation). The skilled person will be able to select humanizing substitutions or suitable combinations of humanizing substitutions, which optimize or achieve a suitable balance between the favourable properties provided by the humanizing substitutions on the one hand and the favourable properties of naturally occurring VHH domains on the other hand. In general, the specificity of binding to the target is not significantly (negatively) affected in a humanized antibody/immunoglobulin/IVD (or polypeptide comprising such antibody/immunoglobulin/IVD) and, in general, the affinity and/or avidity of binding to the target is not significantly (negatively) affected in a humanized antibody/immunoglobulin/IVD (or polypeptide comprising such antibody/immunoglobulin/IVD).

The huPDL1-binding polypeptides of the invention may comprise (in a fusion, conjugated therewith, or complexed therewith), one or more non-(poly)peptidic constituents (such as detectable moieties—see further; or such as pegylation—see e.g. WO2017/059397), one or more further polypeptide(s) or polypeptide domain(s) (such as e.g. a His-tag, or sortag motif, i.e., sortase amino acid substrate motif LPXTG (SEQ ID NO:17), e.g. LPETG (SEQ ID NO:18)), referred to herein as "functional moiety". In one instance, the huPDL1-binding polypeptide itself may be duplicated or multiplicated (wherein the monomers are e.g. connected through a flexible linker such as a linker based on Gly-Pro repeats, Pro-Ala repeats, Gly-Ser repeats, or combinations thereof) to form a multivalent (though monospecific) binding molecule. In another instance, the further polypeptide or polypeptide domain (which may be connected through a flexible linker such as a linker based on Gly-Pro repeats, Pro-Ala repeats, Gly-Ser repeats, or combinations thereof, to the huPDL1-binding polypeptide) may confer binding to an entity different from huPDL1, may exert an enzymatic function (such as for, but not limited to, ADEPT (antibody-directed enzyme prodrug therapy)), may exert a toxic function (such as for, but not limited to, ADC (antibody-drug conjugates)), may confer a fluorescent signalling function to the combined polypeptide (e.g. fluorescent protein), may confer increased serum half-life (e.g. a serum albumin binding protein or peptide; less desired for imaging purposes but desired for therapeutic purposes), or may confer an additional therapeutic function. Clearly, any of these can be combined in any way in a huPDL1-binding polypeptide of the invention.

Thus, in any of the above, the huPDL-1 binding polypeptide may further comprise a functional moiety. In one embodiment, the functional moiety is a detectable moiety. HuPDL1-binding polypeptides as defined herein and carrying a detectable moiety therewith may be immunotracers; in case the detectable moiety is a radiolabel, the huPDL-1 binding polypeptides may be radioimmunotracers.

A "detectable moiety" in general refers to a moiety that emits a signal or is capable of emitting a signal upon adequate stimulation, and is detectable by any means, preferably by a non-invasive means, once inside the human body. Furthermore, the detectable moiety may allow for computerized composition of an image, as such the detectable moiety may be called an imaging agent. Detectable moieties include fluorescence emitters, positron emitters, radioemitters, etc.

Measuring the amount of detectable moiety/imaging agent (comprised in, carried by, coupled to, chelated on a huPDL1-binding polypeptide) is typically done with a device counting radioactivity or determining radiation (which can be of photonic nature) density or radiation concentration. The counted or determined radioactivity can be transformed into an image. Depending on the nature of the emission by the detectable moiety, it may be detectable by techniques such as PET (positron emission tomography), SPECT (single-photon emission computed tomography), fluorescence imaging, fluorescence tomography, near infrared imaging, near infrared tomography, optical tomography, etc.

Examples of radioemitters/radiolabels include $^{68}$Ga, $^{110m}$In, $^{18}$F, $^{45}$Ti, $^{44}$Sc, $^{47}$Sc, $^{61}$Cu, $^{60}$Cu, $^{62}$Cu, $^{66}$Ga, $^{64}$Cu, $^{55}$Ca, $^{72}$As, $^{86}$Y, $^{90}$Y, $^{89}$Zr, $^{125}$I, $^{74}$Br, $^{75}$Br, $^{76}$Br, $^{77}$Br, $^{78}$Br, $^{111}$In, $^{114m}$In, $^{114}$In, $^{99m}$Tc, $^{11}$C, $^{32}$Cl, $^{34}$Cl, $^{123}$I, $^{124}$I, $^{131}$I, $^{186}$Re, $^{188}$Re, $^{177}$Lu, $^{99}$Tc, $^{212}$Bi, $^{213}$Bi, $^{212}$Pb, $^{225}$Ac, $^{153}$Sm, and $^{67}$Ga. Fluorescence emitters include cyanine dyes (e.g. Cy5, Cy5.5, Cy7, Cy7.5), indolenine-based dyes, benzoindolenine-based dyes, phenoxazines, BODIPY dyes, rhodamines, Si-rhodamines, Alexa dyes, and derivatives of any thereof.

Many of the radionuclides have a metallic nature and are typically incapable of forming stable covalent bonds with proteins or peptides. One solution is to label proteins or peptides with radioactive metals by means of chelators, i.e. multidentate ligands, which form non-covalent compounds, called chelates, with the metal ions. A huPDL1 binding polypeptide may thus be coupled in any way to such chelator, which enables incorporation of a radionuclide; this allows a radionuclide to be coordinated, chelated or complexed to the huPDL1-binding polypeptide. Chelators include polyaminopolycarboxylate-type chelators which can be macrocyclic or acyclic. A polyaminopolycarboxylate chelator can be conjugated to a huPDL1-binding polypeptide e.g. via a thiol group of a cysteine residue or via an epsilon amine group of a lysine residue. Macrocyclic chelators for radioisotopes such as indium, gallium, yttrium, bismuth, radioactinides and radiolanthanides include DOTA (1,4,7,10-tetraazacyclododecane-1,4,7,10-tetraacetic acid) and derivatives thereof such as maleimidomonoamide-DOTA (1,4,7,10-tetraazacyclododecane-1,4,7-tris-acetic acid-10-maleimidoethylacetamide), DOTAGA (2,2',2''-(10-(2,6-dioxotetrahydro-2H-pyran-3-yl)-1,4,7,10-tetraazacyclododecane-1,4,7-triyl)triacetic acid) with said polypeptide. Other chelators include NOTA (1,4,7-triazacyclononane-1,4,7-triacetic acid), and derivatives thereof such as NODAGA (2,2'-(7-(1-carboxy-4-((2,5-dioxopyrrolidin-1-yl)oxy)-4-oxobutyl)-1,4,7-triazonane-1,4-diyl)diacetic acid). Acyclic polyaminopolycarboxylate chelators include different derivatives of DTPA (diethylenetriamine-pentaacetic acid). Further chelating agents include DFO, CB-DO2A, 3p-C-DEPA, TCMC, Oxo-DO3A, TE2A, CB-TE2A, CB-TE1A1P, CB-TE2P, MM-TE2A, DM-TE2A, diamsar, NODASA, NETA, TACN-TM, 1B4M-DTPA, CHX-A''-DTPA, TRAP, NOPO, AAZTA, DATA, H2dedpa, H4octapa, H2azapa, H5decapa, H6phospa, HBED, SHBED, BPCA, CP256, PCTA, HEHA, PEPA, EDTA, TETA, and TRITA.

The detectable moiety in a huPDL1-binding polypeptide, may itself be comprised in a prosthetic group and the prosthetic group may be linked to the polypeptide through a chelator or conjugating moiety such as a cyclooctyne comprising a reactive group that forms a covalent bond with an amine, carboxyl, carbonyl or thiol functional group on the huPDL1-binding polypeptide. Cyclooctynes include dibenzocyclooctyne (DIBO), biarylazacyclooctynone (BARAC), dimethoxyazacyclooctyne (DIMAC) and dibenzocyclooctyne (DBCO), DBCO-PEG4-NHS-Ester, DBCO-Sulfo-NHS-Ester, DBCO-PEG4-Acid, DBCO-PEG4-Amine or DBCO-PEG4-Maleimide. An example of an $^{18}$F-labelled prosthetic group is $^{18}$F-3-(2-(2-(2-(2-azidoethoxy)ethoxy)ethoxy)ethoxy)-2-fluoropyridine ($^{18}$F-FFPEGA). Other $^{18}$F-labelled prosthetic groups include N-Succinimidyl-4-[$^{18}$F] fluorobenzoate ([$^{18}$F]SFB) (e.g. Li et al. 2014, Applied Radiation and Isotopes 94:113-117); I-labelled prosthetic groups include N-succinimidyl 4-guanidinomethyl-3-[(*)I] iodobenzoate ([(*)I]SGMIB) and N-succinimidyl 3-guanidinomethyl-5-[(*)I]iodobenzoate (iso-[(*)I]SGMIB) wherein (*)I is for instance 131I (see e.g. Choi et al. 2014, Nucl Med Biol 41:802-812).

Conjugation methods as described above may result in heterogeneous tracer populations. Site-specific conjugation strategies try to overcome this shortcoming and include chemoenzymatic methods to couple polypeptides such as antibodies/immunoglobulins/IVDs with a chelator or detectable moiety such as via sortase-mediated transpeptidation (Antos et al. 2009, Curr Protoc Protein Sci, Chapter 15:unti-15.3) (reviewed by e.g. Massa et al. 2016, Exp Opin Drug Deliv 13:1149-1163).

Other aspects relate to isolated nucleic acids encoding a huPDL1-binding polypeptide as described hereinabove; to vectors comprising such nucleic acid; and to host cells comprising such nucleic acid or vector, and/or expressing huPDL1-binding polypeptide as described hereinabove.

A further aspect relates to pharmaceutical compositions comprising a huPDL1-binding polypeptide as described hereinabove (huPDL1-binding polypeptides without/not comprising a functional moiety, huPDL1-binding polypeptides with/comprising a functional moiety, or huPDL1-binding polypeptides with/comprising a detectable moiety).

Yet a further aspect relates to huPDL-1 binding polypeptide as described hereinabove, or to a pharmaceutical composition comprising it, for use as a medicament, for use in diagnosis, for use in surgery, for use in treatment, for use in therapy monitoring, for use in dendritic cell vaccination, and in particular for use as an imaging agent.

Diagnosis

In general "diagnosis" herein refers to detection of human PD-L1. This can be ex vivo or in vitro such as in a sample from a human subject (and such as by for instance ELISA, immunocytochemistry (ICH), western blot, or surface Plasmon resonance). This can also be in vivo diagnosis, in particular non-invasive in vivo diagnosis such as by medical imaging or molecular imaging as described hereinabove. Diagnosis, whether on a sample from a human subject or by in vivo (imaging) methods allows to identify patients eligible to treatment with a PD1- or PDL-1-based immune checkpoint inhibitor (such as with huPDL1-binding polypeptides of the current invention without/not comprising a detectable moiety), therewith avoiding non-effective treatment and saving on payer's budgets, and/or to monitor the effect of such immune checkpoint therapy and to monitor whether, at any time, such immune checkpoint therapy is expected to still be effective. Diagnosis, and especially imaging, may also assist in defining e.g. a tumour in need of surgical resection, thus in assisting surgery.

Treatment

"Treatment"/"treating" refers to any rate of reduction, delaying or retardation of the progress of the disease or disorder, or a single symptom thereof, compared to the progress or expected progress of the disease or disorder, or single symptom thereof, when left untreated. More desirable, the treatment results in no/zero progress of the disease or disorder, or single symptom thereof (i.e. "inhibition" or "inhibition of progression"), or even in any rate of regression of the already developed disease or disorder, or single symptom thereof. "Suppression/suppressing" can in this context be used as alternative for "treatment/treating". Treatment/treating also refers to achieving a significant amelioration of one or more clinical symptoms associated with a disease or disorder, or of any single symptom thereof. Depending on the situation, the significant amelioration may be scored quantitatively or qualitatively. Qualitative criteria may e.g. by patient well-being or quality of life. In the case of quantitative evaluation, the significant amelioration is typically a 10% or more, a 20% or more, a 25% or more, a 30% or more, a 40% or more, a 50% or more, a 60% or more, a 70% or more, a 75% or more, a 80% or more, a 95% or more, or a 100% improvement over the situation prior to treatment. The time-frame over which the improvement is evaluated will depend on the type of criteria/disease observed and can be determined by the person skilled in the art. Treatment also refers to prevention of disease relapse. Relapse in this context refers to the return of a disease or the signs and symptoms of a disease after a period of improvement. In particular herein, treatment is meant to be a treatment including a PD1- or PDL1-based immune checkpoint inhibitor (such as with huPDL1-binding polypeptides of the current invention without/not comprising a detectable moiety). Such treatment including a PD1- or PDL-1-based immune checkpoint inhibitor may also be combined with other complementary forms of treatment, such as surgery, chemotherapy, radiotherapy, oncolytic viruses, blocking of immune checkpoints other than PD1 or PDL-1, adoptive transfer of natural or engineered immune cells (such as the so-called chimeric antigen receptor T cells or CAR-T cells) and/or vaccination using proteins, nucleic acids or cells (such as dendritic cells). Alternatively, the anti-PD-L1 IVDS as described herein can be combined in any way (in the same or in separate (pharmaceutical) compositions; concurrent or sequentially in any order; in one or more or multiple doses or administrations) with one or more other immunotherapeutic or immunogenic agents.

Therapy Monitoring

The FDA has approval anti-PD-1 mAbs pembrolizumab and nivolumab, and anti-PD-L1 mAbs durvalumab, atezolizumab and avelumab, which have since become available as standard-of-care for several cancer types. The downside of this success story is the high cost of such treatments, easily surpassing $100,000 per patient (Aguiar et al. 2017, Ann Oncol 28:2256-2263), and the observation that these immune checkpoint blockers are only of benefit for a subset of patients (Alsaab et al. 2017, Front Pharmacol 8:561). The failure rate, combined with the high cost for society, drives the search for predictive biomarkers that can help select the right treatment for the right patient. Currently the most commonly used predictive biomarker is PD-L1 expression assessed via IHC on tumor biopsies, although limitations are obviously present. Limitations such as heterogeneous expression, the role of expression outside of the tumor, and its dynamic expression during the disease process could be overcome by noninvasive molecular imaging using radiolabeled tracers that allow deep tumor penetration and repeated quantification of PD-1 and/or PD-L1 expression, which should enable mapping of primary tumors and metastatic lesions both before and during the treatment. Data generated by England et al. 2018 (Eur J Nucl Med Mol Imaging 45:110-120) show that PD-1-targeted tumor imaging in vivo can assist in disease diagnostics, patient stratification (determining which patients are more likely to respond to immunotherapy), disease monitoring (changes in the tumor images obtained during therapy reflect response or non-response to immunotherapy) and the design and development of new immunotherapies (throughout pre-clinical or clinical development). In particular, imaging (such as immunoPET imaging) of cancer and immune cells based on labeled anti-PL1 moieties of the current invention can likewise assist in monitoring the efficacy of immunotherapy or immunogenic therapy, while also assisting in patient stratification and providing valuable information when designing and/or developing new immunotherapies or immunogenic therapies.

Dendritic Cells (DC) and DC Vaccination

Dendritic cell [DC] vaccines can induce durable clinical responses, at least in a fraction of previously treated, late-stage cancer patients. Several preclinical studies suggest that shielding programmed death-ligand 1 [PD-L1] on the DC surface may be an attractive strategy to extend such clinical benefits to a larger patient population. Dendritic cell [DC] vaccination is therefore extensively studied as a strategy to activate cancer-specific cytotoxic T lymphocytes [CTLs]. To induce potent antitumour CTLs three requirements need to be fulfilled: first, the peptide/MHC-I complex on the surface of DCs must be correctly recognized by the T-cell receptor [TCR] expressed on $CD8^{pos}$ T cells. Second, co-stimulatory molecules, like CD80 and CD86, expressed on DCs, need to bind with co-stimulatory receptors, like CD28, expressed on $CD8^{pos}$ T cells. Finally, a third signal is provided by DCs under the form of cytokine secretion. Only, when those requirements are fulfilled, activated and effective T cells will be able to attack tumour cells (Santos & Butterfield 2018, J Immunol 200:443-449).

DCs also express inhibitory molecules, like programmed death-ligand 1 [PD-L1], which binds to its receptor programmed death-1 [PD-1] on activated CTLs, and acts as a brake on T-cell activation (Liechtenstein et al. 2012, J Clin Cell Immunol S12). Interaction of PD-L1 with PD-1 during antigen presentation results in TCR down-modulation (Karwacz et al. 2011, EMBO Mol Med 3:581-592; Yokosuka et al. 2012, J Exp Med 209:1201-1217). As a consequence TCR-signalling is down-regulated as well, preventing T-cell hyper activation (Boding et al. 2009, J Immunol 183:4994-5005). However, in the case of vaccination in the context of cancer as wells as of infectious diseases (see, e.g., Qu et al. 2014, Int J Infect Dis 19:1-5 "Monocyte-derived dendritic cells: targets as potent antigen-presenting cells for the design of vaccines against infectious diseases"), hyperactivation of T-cells is warranted.

Several strategies have been successfully employed to interfere with PD-L1:PD-1 interactions during antigen presentation by DCs to $CD8^{pos}$ T cells. These include silencing of PD-L1 (Karwacz et al. 2011, EMBO Mol Med 3:581-592; Hobo et al. 2010, Blood 116:4501-4511), use of soluble PD-1 or PD-L1 (He et al. 2005, Anticancer Res 25:3309-3313; Pen et al. 2014, Gene Ther 21:3309-3313) and use of antibodies (Karwacz et al. 2011, EMBO Mol Med 3:581-592; Ge et al. 2013, Cancer Lett 336:253-259; Lichtenegger et al. 2018, Front Immunol 9:385).

Reported in the Examples herein is the development of a single domain antibody [sdAb] that binds human PD-L1 with high affinity on the same epitope as the monoclonal antibody [mAb] avelumab. This sdAb was demonstrated in the Examples hereinto have high potential for imaging of PD-L1 expressed on tumour cells. It was further established that the sdAb blocks the interaction between PD-1 and PD-L1 on the protein level, and that this blocking ability facilitates killing of tumour cells by cytolytic immune cells present in peripheral blood mononuclear cells [PBMCs]. As sdAbs are versatile antigen binding moieties, further studies pointed to the applicability of the sdAb to enhance the activation of tumour antigen-specific $CD8^{pos}$ T cells by monocyte-derived DCs [moDCs]. In particular, a high affinity, antagonistic, PD-L1-specific sdAb (single domain antibody) was evaluated for its ability to enhance DC-mediated T-cell activation, and benchmarked against the use of the monoclonal antibodies [mAbs], MIH1, 29E.2A3 and avelumab. Similar to mAbs, the sdAb enhanced antigen-specific T-cell receptor signaling in PD-$1^{pos}$ reporter cells activated by DCs. It was further shown that the activation and function of antigen-specific $CD8^{pos}$ T cells, activated by DCs, was enhanced by inclusion of an sdAb, but not mAbs. This was most pronounced when less mature DCs were used for T-cell activation. The failure of mAbs to enhance T-cell activation might be explained by their low efficacy to bind PD-L1 on DCs when compared to binding of PD-L1 on non-immune cells and binding of PD-L1 by an sdAb. These data provide a rationale for the inclusion of anti-PD-L1 sdAb in DC-based immunotherapy strategies (such as for treating or inhibiting cancer or infectious diseases).

Immunotherapy and Immunogenic Therapy

Immunotherapy in general is defined as a treatment that uses the body's own immune system to help fight a disease, more specifically cancer in the context of the current invention. Immunotherapeutic treatment as used herein refers to the reactivation and/or stimulation and/or reconstitution of the immune response of a mammal towards a condition such as a tumour, cancer or neoplasm evading and/or escaping and/or suppressing normal immune surveillance. The reactivation and/or stimulation and/or reconstitution of the immune response of a mammal in turn in part results in an increase in elimination of tumorous, cancerous or neoplastic cells by the mammal's immune system (anticancer, antitumour or anti-neoplasm immune response; adaptive immune response to the tumour, cancer or neoplasm). Immunotherapeutic agents of particular interest include immune checkpoint inhibitors (such as anti-PD-1, anti-PD-L1 or anti-CTLA-4 antibodies), bispecific antibodies bridging a cancer cell and an immune cell, dendritic cell vaccines, Immunotherapy is a promising new area of cancer therapeutics and several immunotherapies are being evaluated pre-clinically as well as in clinical trials and have demonstrated promising activity (Callahan et al. 2013, J Leukoc Biol 94:41-53; Page et al. 2014, Annu Rev Med 65:185-202). However, not all the patients are sensitive to immune checkpoint blockade and sometimes PD-1 or PD-L1 blocking antibodies accelerate tumour progression. An overview of clinical developments in the field of immune checkpoint therapy is given by Fan et al. 2019 (Oncology Reports 41:3-14). Monoclonal antibodies targeting and inhibiting PD-1 include pembrolizumab, nivolumab, and cemiplimab. Monoclonal antibodies targeting and inhibiting PD-L1 include atezolizumab, avelumab, and durvalumab. Monoclonal antibodies targeting and inhibiting CTLA-4 include ipilimumab. Combinatorial cancer treatments that include chemotherapies can achieve higher rates of disease control by impinging on distinct elements of tumour biology to obtain synergistic antitumour effects. It is now accepted that certain chemotherapies can increase tumour immunity by inducing immunogenic cell death and by promoting escape in cancer immunoediting, such therapies are therefore called immunogenic therapies as they provoke an immunogenic response. Drug moieties known to induce immunogenic cell death include bleomycin, bortezomib, cyclophosphamide, doxorubicin, epirubicin, idarubicin, mafosfamide, mitoxantrone, oxaliplatin, and patupilone (Bezu et al. 2015, Front Immunol 6:187). Other forms of immunotherapy include chimeric antigen receptor (CAR) T-cell therapy in which allogeneic T-cells are adapted to recognize a tumour neo-antigen and oncolytic viruses preferentially infecting and killing cancer cells. Treatment with RNA, e.g. encoding MLKL, is a further means of provoking an immunogenic response (Van Hoecke et al. 2018, Nat Commun 9:3417), as well as vaccination with neo-epitopes (Brennick et al. 2017, Immunotherapy 9:361-371).

In a final aspect, the invention relates to methods for producing a huPDL1-binding polypeptide according to the invention, such methods comprising the steps of:
expressing the huPDL1-binding polypeptide in a suitable host cell (such as comprising a nucleic acid or vector as described herein; and
purifying the expressed huPDL1-binding polypeptide.

Such methods may further comprise a step of coupling, incorporating, binding, ligating, bonding, complexing, chelating, conjugating (e.g. site-specifically conjugating) or otherwise linking, covalently or non-covalently, a detectable moiety to the purified huPDL1-binding polypeptide.

Other Definitions

The present invention is described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, N.Y. (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

The term "defined by SEQ ID NO:X" as used herein refers to a biological sequence consisting of the sequence of amino acids or nucleotides given in the SEQ ID NO:X. For instance, a CDR defined in/by SEQ ID NO:X consists of the amino acid sequence given in SEQ ID NO:X. A further example is an amino acid sequence comprising SEQ ID NO:X, which refers to an amino acid sequence longer than the amino acid sequence given in SEQ ID NO:X but entirely comprising the amino acid sequence given in SEQ ID NO:X (wherein the amino acid sequence given in SEQ ID NO:X can be located N-terminally or C-terminally in the longer amino acid sequence, or can be embedded in the longer amino acid sequence), or to an amino acid sequence consisting of the amino acid sequence given in SEQ ID NO:X.

The term "antibody" as used herein, refers to an immunoglobulin (Ig) molecule, which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The term "immunoglobulin domain" as used herein refers to a globular region of an antibody chain (such as e.g., a chain of a conventional 4-chain antibody or a chain of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel β-strands arranged in two (3-sheets, optionally stabilized by a conserved disulphide bond.

The specificity of an antibody/immunoglobulin/IVD for an antigen is defined by the composition of the antigen-binding domains in the antibody/immunoglobulin/IVD (usually one or more of the CDRs, the particular amino acids of the antibody/immunoglobulin/IVD interacting with the antigen forming the paratope) and the composition of the antigen (the parts of the antigen interacting with the antibody/immunoglobulin/IVD forming the epitope). Specificity of binding is understood to refer to a binding between an antibody/immunoglobulin/IVD with a single target molecule or with a limited number of target molecules that (happen to) share an epitope recognized by the antibody/immunoglobulin/IVD.

Affinity of an antibody/immunoglobulin/IVD for its target is a measure for the strength of interaction between an epitope on the target (antigen) and an epitope/antigen binding site in the antibody/immunoglobulin/IVD. It can be defined as:

$$K_A = \frac{[Ab-Ag]}{[Ab][Ag]}$$

Wherein KA is the affinity constant, [Ab] is the molar concentration of unoccupied binding sites on the antibody/immunoglobulin/IVD, [Ag] is the molar concentration of unoccupied binding sites on the antigen, and [Ab–Ag] is the molar concentration of the antibody-antigen complex.

Avidity provides information on the overall strength of an antibody/immunoglobulin/IVD-antigen complex, and generally depends on the above-described affinity, the valency of antibody/immunoglobulin/IVD and of antigen, and the structural interaction of the binding partners.

The term "immunoglobulin variable domain" (abbreviated as "IVD") as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) (IVDs) that confer specificity to an antibody for the antigen by carrying the antigen-binding site. Methods for delineating/confining a CDR in an antibody/immunoglobulin/IVD have been described hereinabove.

The term "immunoglobulin single variable domain" (abbreviated as "ISVD"), equivalent to the term "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation. In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen. In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs. As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit). In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody. For example, the immunoglobulin single variable domain may be a (single) domain antibody (or an amino acid sequence that is suitable for use as a (single) domain antibody), a "dAb" or dAb (or an amino acid sequence that is suitable for use as a dAb) or a Nanobody® (as defined herein, and including but not limited to a VHH); other single variable domains, or any suitable fragment of any one thereof. In particular, the immunoglobulin single variable domain may be a Nanobody® (as defined herein) or a suitable fragment thereof. Note: Nanobody®, Nanobodies® and Nanoclone® are registered trademarks of Ablynx N.V. For a general description of Nanobodies®, reference is made to the further description below, as well as to the prior art cited herein, such as e.g. described in WO2008/020079.

"VHH domains", also known as VHHs, VHH domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al (1993) Nature 363: 446-448). The term "VHH domain" has been chosen to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHHs and Nanobody®, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. As described in these references, Nanobody® (in particular VHH sequences and partially humanized Nanobody®) can in particular be characterized by the presence of one or more "Hallmark residues" in one or more of the framework sequences. A further description of the Nanobody®, including humanization and/or camelization of Nanobody®, as well as other modifications, parts or fragments, derivatives or "Nanobody® fusions", multivalent constructs (including some non-limiting examples of linker sequences) and different modifications to increase the half-life of the Nanobody® and their preparations can be found e.g. in WO 08/101985 and WO 08/142164.

"Domain antibodies", also known as "Dabs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutic use in humans. It should also be noted that single variable domains can be derived from certain species of shark (for example, the so-called "IgNAR domains", see for example WO 05/18629).

Immunoglobulin single variable domains such as Domain antibodies and Nanobody® (including VHH domains and humanized VHH domains), can be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. MoI. Biol. 226: 889 896, 1992), Johnson and Hawkins (Affinity maturation of antibodies using phage display, Oxford University Press, 1996). The process of designing/selecting and/or preparing a polypeptide, starting from an immunoglobulin single variable domain such as a Domain antibody or a Nanobody®, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats for instance to avoid glycosylation will be clear to the skilled person based on the disclosure herein.

Immunoglobulin single variable domains such as Domain antibodies and Nanobody® (including VHH domains) can be subjected to humanization, i.e. increase the degree of sequence identity with the closest human germline sequence. In particular, humanized immunoglobulin single variable domains, such as Nanobody® (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring VHH sequence with the corresponding framework sequence of one or more closely related human VH sequences, after which one or more of the potentially useful humanizing substitutions (or combinations thereof) thus determined can be introduced into said VHH sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person. Also, based on what is described before, (the framework regions of) an immunoglobulin single variable domain, such as a Nanobody® (including VHH domains) may be partially humanized or fully humanized.

A "serum albumin binding agent", or "serum albumin binding polypeptide", as used herein, is a protein-based agent capable of specific binding to serum albumin. In various embodiments, the serum albumin binding agent may bind to the full-length and/or mature forms and/or isoforms and/or splice variants and/or fragments and/or any other naturally occurring or synthetic analogues, variants or mutants of serum albumin. In various embodiments, the serum albumin binding agent of the invention may bind to any forms of serum albumin, including monomeric, dimeric, trimeric, tetrameric, heterodimeric, multimeric and associated forms. In an embodiment, the serum albumin binding agent binds to the monomeric form of serum albumin. In an embodiment, the present serum albumin binding polypeptide comprises immunoglobulin variable domain with an antigen binding site that comprises three complementarity determining regions (CDR1, CDR2 and CDR3). In an embodiment said antigen binding site recognizes one or more epitopes present on serum albumin. In various embodiments, the serum albumin binding agent comprises a full length antibody or fragments thereof. In an embodiment, the serum albumin binding agent comprises a single domain antibody or an immunoglobulin single variable domain (ISVD). In a specific embodiment, the serum albumin binding agent binds to serum albumin of rat (Uniprot P02770). In a specific embodiment, the serum albumin binding agent binds to serum albumin of mouse (Uniprot P07724). In a specific embodiment, the serum albumin binding agent binds to human serum albumin (Uniprot P02768).

The aspects and embodiments described above in general may comprise the administration of a huPDL1-binding polypeptide or pharmaceutical composition comprising it to a mammal in need thereof, i.e., harbouring a tumour, cancer or neoplasm in need of (non-invasive) medical imaging, diagnosis, treatment, surgery, therapy monitoring, or dendritic cell vaccination. In general a (therapeutically) effective amount of the huPDL1-binding polypeptide or pharmaceutical composition comprising it is administered to the mammal in need thereof in order to meet the desired effect. The (therapeutically) effective amount will depend on many factors such as route of administration and will need to be determined on a case-by-case basis by the physician. In general the maximum dose of (therapeutically) effective amount of huPDL1-binding polypeptide or pharmaceutical composition comprising it that may be administered to a mammal is determined by the possible toxicity and is reflected in the maximum tolerated dose (MTD), i.e. the highest dose that does not cause unacceptable side effects. "Administering" means any mode of contacting that results in interaction between an agent (e.g. a huPDL1-binding polypeptide as described herein) or composition comprising the agent (such as a medicament or pharmaceutical composition) and an object (e.g. cell, tissue, organ, body lumen) with which said agent or composition is contacted. The interaction between the agent or composition and the object can occur starting immediately or nearly immediately with the administration of the agent or composition, can occur over an extended time period (starting immediately or nearly immediately with the administration of the agent or composition), or can be delayed relative to the time of administration of the agent or composition. More specifically the "contacting" results in delivering an effective amount of the agent or composition comprising the agent to the object.

The term "effective amount" refers to the dosing regimen of the agent (e.g. huPDL1-binding polypeptide as described herein) or composition comprising the agent (e.g. medicament or pharmaceutical composition). The effective amount will generally depend on and/or will need adjustment to the mode of contacting or administration. To obtain or maintain the effective amount, the agent or composition comprising the agent may be administered as a single dose or in multiple doses. The effective amount may further vary depending on the severity of the condition that needs to be diagnosed, imaged, or treated; this may depend on the overall health and physical condition of the mammal or patient and usually a doctor's or physician's assessment will be required to establish what is the effective amount. The effective amount may further be obtained by a combination of different types of contacting or administration.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

The content of the documents cited herein are incorporated by reference.

EXAMPLES

1. Materials and Methods
1.1. Reagents

All Biacore consumables were from GE Healthcare. A recombinant His-tagged human PD-L1 protein (SINO Biologicals, 10084-H08H) was used to determine the affinity of purified single domain antibodies (sdAbs) in Surface Plasmon Resonance (SPR). Recombinant Fc-tagged human PD-L1 (R&D Systems, 156-B7) or PD-1 (R&D Systems, 1086-PD) proteins were used to evaluate the $IC_{50}$ in SPR. Avelumab (Bavencio) was provided by Merck KGaA [EMD Serono] and Pfizer. A sdAb specific for a multiple myeloma paraprotein, designated R3B23 (Lemaire et al. 2014, Leukemia 28:444-447), and trastuzumab (Herceptin®, Roche) served as negative controls.

The following blocking anti-PD-L1 mAbs were used in the functional assays; the IgG1 mAbs, MIH1 [eBioscience] and avelumab [Bavencio®, Merck KGaA], and the IgG2b mAb 29E.2A3 [Bioxcell]. The isotype-matched control mAbs, P3.6.2.8.1 [IgG1, eBiosciences] and MOPC-21 [IgG2b, Bioxcell], were used as controls. The human PD-L1-specific sdAb K2 is described herein. An sdAb specific for the 5T2MM paraprotein, sdAb R3B23, was used as a control (Lemaire et al. 2014, Leukemia 28:444-447).

An anti-His monoclonal antibody (mAb) (AbD Serotec, AD1.1.10) and phycoerythrin (PE) conjugated anti-mouse IgG antibody (BD biosciences, A85-1) was used to detect binding of purified His-tagged sdAbs to PD-L1 expressed on cells in flow cytometry. An allophycocyanin (APC) conjugated antibody specific for human PD-L1 (eBioscience, MIH5) was used in flow cytometry to evaluate PD-L1 expression on cells. A PE conjugated anti-HLA-A2 antibody (BD Biosciences, BB7.2) and conjugated anti-CD45 antibody were used to discriminate tumour cells from immune cells. An anti-human PE-labelled IgG1 antibody (Miltenyi Biotec, IS11-12E4.23.20) was used to detect binding of avelumab to PD-L1POS 293T cells.

Expression of PD-L1 on cells was evaluated with anti-PD-L1 antibodies coupled to allophycocyanin (APC, eBioscience, MIH1) or PE-CF594 (Biolegend, MIH1), HLA-A2 using a PE-conjugated anti-HLA-A2 antibody (BD biosciences, BB7.2), PD-1 using a PE-conjugated anti-PD-1 antibody (Biolegends, EH12.2H7). 2D3 cells were discriminated from tumour cells in the 2D3 functional assay using an APC-H7-labelled anti-CD8 antibody (BD biosciences, SK1). Expression of the T-cell receptor (TCR) on electroporated 2D3 cells was evaluated with a PE-labelled anti-TCRα/β antibody (Biolegend, IP26). Isotype-matched antibodies served as controls (BD biosciences).

The following antibodies were used to phenotype the cells used in functional assays: a PECF594 conjugated anti-CD3 (Biolegend, UCHT1) and anti-CD70 (BD Biosciences, Ki-24), a PerCP-Cy5.5 conjugated anti-CD4 (BD Biosciences, RPA-T4), an APC-H7 conjugated anti-CD8 (BD Biosciences, SK1), a PE conjugated anti-PD-1 (BD Biosciences, MIH4) and anti-HLA-A2 (BD Biosciences, BB7.2), a PE-Cy7 conjugated anti-HLA-DR (BD Biosciences, G46-6), a fluorescein isothiocyanate conjugated anti-CD86 (BD Biosciences, FUN-1), an APC conjugated anti-PD-L2 (BD Biosciences, MIH18), a PerCPEF710 conjugated anti-CD80 (eBiosciences, 2D10.4), an anti-PD-L1-APC [eBioscience, MIH5], an anti-PD-1-PE [Biolegend, EH12.2H7], an anti-CD11c-AF700 [BD biosciences, clone B-ly6], an anti-PD-L1-PE-CF594 [BD Biosciences, clone MIH1], an anti-CD86-BV421 [BD Biosciences, clone HB15e], an anti-CD83-PE [BD Biosciences, clone HB15e], an anti-CD40-APC [Biolegend, clone 5C3], an anti-CD80-PerCP-EF710 [eBioscience, clone 2D10.4], an anti-HLA-ABC-FITC [BD biosciences, clone G46-2.6]. Isotype matched control (IC) antibodies were purchased from BD Biosciences.

A Melan-A/MART-1 HLA-A2 dextramer conjugated to PE (ELAGIGILTV, SEQ ID NO:19; Immudex) was used to detect Melan-A specific T cells in flow cytometry. A gp100 HLA-A2 dextramer conjugated to PE (YLEPGPVTV, SEQ ID NO:20; Immudex) was used as a control.

The $gp100_{280-288}$ peptide (YLEPGPVTA, SEQ ID NO:21; Eurogentec) was used to pulse antigen presenting cells in the 2D3 assay. A blocking anti-PD-L1 antibody (eBioscience, MIH1) and an isotype matched control antibody (eBioscience, P3.6.2.8.1) were used in the 2D3 assay. The anti-PD-L1 antibody (29E.2A3) and its isotype matched control antibody (MPC-11) purchased from Bioxcell were used in the other functional assays.

Avelumab (Bavencio®, provided by Merck KGaA [EMD Serono] and Pfizer), an isotype-matched control antibody (Bioxcell, MOPC-21) and R3B23 were used in the 2D3 and 3D spheroid assays as controls.

1.2. Generation and Selection of PD-L1 Specific sdAbs

Human PD-L1 specific sdAbs were generated in alpacas. Briefly, alpacas were immunized subcutaneously for 5 to 6 times at a weekly to biweekly interval with either 10×10E6 RAW264.7 cells or with 100 µg recombinant human PD-L1-Fc protein (R&D Systems, 156-B7). Peripheral blood lymphocytes were purified and used as a source to create a sdAb phage display library. PD-L1 reactive sdAbs were identified by biopanning of this library and ELISA screening of periplasmatic extracts of individual sdAb clones on recombinant mouse or human PD-L1 protein. Sequence analysis was performed on sdAb clones that specifically bound PD-L1. Anti-PD-L1 sdAbs and the control sdAb R3B23 were produced and purified as described (Broos et al. 2017, Oncotarget 8:41932-41946). Therefore, the sdAb cDNA was cloned in the vector pHEN6 to incorporate a C-terminal HIS-tag.

1.3. Large-Scale Selection, Production and Purification of sdAbs

The selected sdAbs and sdAb R3B23, specific for the 5T2MM paraprotein (Lemaire et al. 2014, Leukemia 28:444-447), were produced and purified including cloning of the sdAb encoding cDNAs into the vector pHEN6 as to incorporate a C-terminal HIS-tag.

1.4. Surface Plasmon Resonance

All measurements were performed on a Biacore T200 device (GE Healtcare) at 25° C. and using Hepes-buffered saline (0.01M HEPES, pH 7.4; 0.15M NaCl, 3 mM EDTA, 0.005% Tween20) as running buffer. All recombinant proteins were dissolved to 10 µg/mL in 10 mM Na-acetate (pH 5.0) for immobilization on a CM5 sensor chip using linkage chemistry with 1-(3-(dimethylamino)propyl)-3-ethylcarbodiimide (EDC) and N-hydroxy-succinimide (NETS). Unreacted EDC-NHS linkers were blocked with 1M ethanolamine-HCl. For all measurements, SPR signals in the flow cell with immobilized protein were subtracted with those in a flow cell that underwent the same manipulations but where recombinant protein was omitted, to obtain specific binding signals (response units, RU). Affinity for human PD-L1 of the purified sdAbs was evaluated on immobilized PD-L1 protein.

To evaluate the sdAb's $IC_{50}$, the sdAb concentration at which the relative response of the interaction between PD-1 and PD-L1 is inhibited by half, Fc-PD-1 protein was immobilized on a CM5 chip. Different concentrations of the sdAb (400 to 0.78 nM using a 2-fold dilution series or an excess amount of 1000 nM) were mixed with recombinant human Fc-PD-L1 protein using the $K_D$-value concentration of the PD-L1:PD-1 interaction (25 nM), and run over the chip. The maximum relative response values were plotted in function of competing sdAb concentration and analyzed with a "Log inhibitor versus response (variable lope)" model in Prism to calculate $IC_{50}$ values. To evaluate competition between sdAbs and avelumab for binding to PD-L1, competition studies were performed as described (Vaneycken et al. 2011, FASEB J 25:2433-2446).

1.5. Mice and Cell Lines

Female C57BL/6 mice and athymic nude mice (Crl:NU (NCr)-Foxn1nu) were supplied by Charles River Laboratories (France) at 6 weeks of age. All experiments were performed in accordance to the European guidelines for animal experimentation under licenses LA1230214 and LA1230272. Experiments were approved by the Ethical Committee for the use of laboratory animals of the Vrije Universiteit Brussel (ECD 15-214-1 and 17-272-6).

Human embryonal kidney (HEK) 293T cells and HLA-A*0201+ breast carcinoma cells (MCF7) were purchased from the American Type Culture Collection (ATCC).

HLA-A*0201+ 624-MEL or 938-MEL cells were provided by S.L. Topalian (National Cancer Institute, USA). 624-MEL and 938-MEL cells were cultured in RPMI1640 medium supplemented with 10% Fetal clone I serum (Thermoscientific), 2 mM L-Glutamine, 100 U/ml penicillin, 100 µg/ml streptomycin, 1 mM sodium pyruvate and nonessential amino acids (Sigma-Aldrich). HEK293T cells were cultured in Dulbecco's modified Eagle's medium (Sigma-Aldrich) supplemented with 10% foetal bovine serum (FBS, Harlan), 2 mM L-Glutamine (L-Glu, Sigma Aldrich) and 100 U/ml penicillin, 100 µg/ml streptomycin (PS, Sigma-Aldrich). MCF7 cells were cultured in Roswell Park Memorial Institute (RPMI) 1640 medium supplemented with FBS, L-Glu, PS, 1 mM sodium pyruvate and nonessential amino acids (Sigma-Aldrich). 2D3 cells were generated as described in Versteven et al. 2018 (Oncotarget 9:27797-27808) and maintained in Iscove's Modified Dulbecco's Medium (IMDM, Invitrogen) supplemented with 10% FBS.

Experiments were performed using blood samples from healthy HLA-A*0201+ donors provided by the Blood Transfusion Center of the University Hospital Brussel (Brussels, Belgium). Isolation of peripheral blood mononuclear cells (PBMCs), CD14+ monocytes and their differentiation to monocyte derived dendritic cells (moDCs) as well as isolation of CD8+ T cells from the remaining PBMCs was performed as described in Tuyaerts et al. 2002 (J Immunol Methods 264:135-151). This study was approved by the Ethics Committees of the Brussels University Hospital (2013/198).

1.6. Lentiviral Production, Characterization and Transduction

The plasmids pCMVΔR8.9 and pMD.G were a gift from D. Trono (Ecole Polytechnique Federal de Lausanne, Swiss). The transfer plasmids encoding eGFP, human PD-L1 and PD-1 were described (Pen et al. 2014, Gene Ther 21:262-271; Breckpot et al. 2003, Gene Med 5:654-667). The production and characterization of lentiviral vectors was described in Goyvaerts et al. 2013 (Gene Ther 19:1133-1140). Transduction of HEK293T, MCF7 and 624-MEL cells with PD-L1 or eGFP encoding lentiviral vectors was carried out at a MOI of 10, while transduction of 2D3 cells with PD-1 encoding lentiviral vectors was carried out at a MOI of 5 using the protocol described to transduce human moDCs (Breckpot et al. 2003, J Gene Med 5:654-667).

1.7. Tumour Challenge

Athymic nude mice were injected subcutaneously with 5×10E6 MCF7, 624-MEL, 938-MEL, or PD-L1 modified MCF7 or 624-MEL cells. One day before transplanting MCF7 cells, mice were implanted with oestrogen pellets (Innovative research of America; 0.36 mg/mice). When mice developed a palpable tumour, tumour volume was followed using an electronic calliper. The tumour length and width were measured using an electronic calliper, and used to calculate the tumour volume using the formula: (length× width$^2$)/2. One day prior to imaging, 938-MEL tumour bearing mice were injected intratumourally with 50 µl phosphate buffered saline (PBS; Sigma-Aldrich) or IFN-gamma (2×10$^6$ IUs/ml, ImmunoTools). Tumour tissue was reduced to single cells using the GentleMACS tumour dissociation protocol (Miltenyi Biotec) (Maenhout et al. 2014, Oncotarget 30:6801-6815).

1.8. $^{99m}$Tc-sdAb Labelling, Pinhole SPECT-Micro-CT Imaging and Image Analysis The sdAbs were labelled as described by Xavier et al. 2012 (Methods Mol Biol 911:485-490). Briefly, the sdAb's C-terminal HIS-tag was coupled to $^{99m}$Tc-tricarbonyl intermediate [$^{99m}$Tc(H$_2$O)$_3$(CO)$_3$]$^{99m}$, which was synthesized using the Isolink® labelling kit (Mallinckrodt Medical BV). The $^{99m}$Tc-sdAb solution was purified on a NAP-5 column (GE Healthcare) pre-equilibrated with PBS to remove unbound ($^{99m}$Tc(H$_2$O)$_3$(CO)$_3$)$^+$ and finally filtered through a 0.22 µm filter (Millipore) to remove aggregates. The labelling efficiency was determined both directly after labelling and after purification by instant thin-layer chromatography (iTLC) with 100% acetone as the mobile phase. Mice were injected intravenously with 100-200, of 45-155MBq of $^{99m}$Tc-labelled sdAbs (10 µg), one hour prior to pinhole SPECT-micro-CT imaging. Imaging was performed as described (Put et al. 2013, J Nucl Med 54:807-814). Micro-CT was performed using a dual-source CT scanner (Skyscan 1178; Skyscan) with 60 kV and 615 mA at a resolution of 83 µm. CT images were reconstructed using filtered back projection (NRecon; Skyscan). Pinhole SPECT micro-CT imaging and image analysis in naive C57BL6 mice, the MCF7 and 624-MEL tumour model were performed as described (Broos et al. 2017, Oncotarget 8:41932-41946). For the 938-MEL model, SPECT/CT was performed on a MILabs VECTor/CT camera. The CT-scan was set to 60 kV and 615 mA. CT scan time was 139 seconds. SPECT-images were obtained using a rat SPECT-collimator (1.5-mm pinholes) in spiral mode, 6 positions for whole-body imaging, with 150 seconds per position, total body SPECT scan was 15 minutes. Images were reconstructed with 0.4 mm voxels with 2 subsets and 4 iterations, without post-reconstruction filter.

SPECT images were reconstructed using an iterative reconstruction algorithm (ordered-subset expectation maximization) modified for the 3-pinhole geometry and automatically reoriented for fusion with CT images based on six $^{57}$Co landmarks (Vanhove et al. 2009, Eur J Nucl Med Mol Imaging 36:1049-1063). Images were further visually analyzed and quantified where appropriate using AMIDE (Medical Image Data Examiner software) (Loening & Gambhir 2003, Mol Imaging 2:131-137). Maximum intensity projections (MIP) were generated using OsiriX Lite software. After imaging, mice were sacrificed and selected organs were isolated to measure radioactivity using a γ-counter (Cobra Inspector 5003, Packard). The amount of radioactivity in organs is expressed as percent injected activity per gram (% IA/g).

1.9. mRNA Production, Electroporation

The human gp100 TCRα and TCRβ pGEM-vectors were kindly provided by Prof. N. Schaft (Universitätsklinikum Erlangen, Germany) (Schaft et al. 2003, J Immunol 170: 2186-2194). The peTheRNA plasmids encoding CD40 Ligand, CD70 and a constitutively active form of TLR4 were described in De Keersmaecker et al (in press). The pGEM-sig-Melan-A-DCLamp plasmid encoding the full-length Melan-A/MART-1 antigen containing the optimized immunodominant Melan-A:HLA-A2 epitope linked to the HLA-II targeting sequence of DC-Lamp was described in Bonehill et al. 2008 (Mol Ther 16:1170-1180). The production, purification, quantification and quality control of mRNA was performed as described (Tuyaerts et al. 2002, J Immunol Meth 264:135-151).

Human gp100 TCRα and β mRNA (2.5 µg each/10E6 cells) was electroporated into 2D3 cells in 2004, OptiMEM medium (Life Technologies) in a 4 mm electroporation cuvette (Cell Projects) using a time constant protocol (300V, 7 ms) and the Gene Pulser Xcell™ device (BIORAD). Electroporation of moDCs with mRNA was performed as described (Tuyaerts et al. 2002, J Immunol Meth 264:135-151).

1.10. 2D3 Assay

The 2D3 assay is detailed elsewhere (Versteven et al., submitted for publication). Briefly, 2D3 cells electroporated to express the TCR recognizing the gp100$_{280-288}$ peptide (YLEPGPVTA, SEQ ID NO:21) restricted to HLA-A2 and modified (or not) to express PD-1 were plated in a 96-well round-bottom plate at 10E5 cells in 200 µL IMDM containing 10% FBS (triplicate). moDCs, MCF7, 624-MEL, PD-L1 engineered MCF7 or 624-MEL cells were pulsed with 50 µg/mL gp100$_{280-288}$ peptide and added to the cultures at effector-stimulator ratios of 10:1 in 100 µL medium. Co-cultures were performed for 24 hours at 37° C., 5% CO$_2$ in the presence of 1 µg/200 µL neutralizing anti-PD-L1 antibody, avelumab (360 nM), or anti-PD-L1 sdAb. Isotype matched control antibodies or sdAb R3B23 were used as controls. The activation of 2D3 cells was measured in flow cytometry as percentage eGFP$^+$ cells within CD8$^+$ 2D3 cells.

1.11. Stimulation of CD8$^+$ Melan-A Specific T Cells by Dendritic Cells

CD8$^+$ T cells were plated at 10E5 cells in triplicate in a 96-well round-bottom plate in 100 µL IMDM containing 1% heat-inactivated human AB serum (Innovative Research), PS, L-Glu and non-essential amino acids. moDCs were electroporated with CD40 Ligand, CD70 and constitutively active TLR4 (10 µg each per 4×10E6 cells) and 10 µg Melan-A mRNA (referred to as TriMixDC-MEL) or solely 10 µg Melan-A mRNA (referred to as DC-MEL). Electroporated DCs were added to the T cells at an effector: stimulator ratio of 10:1 in 100 µL medium. Co-cultures with TriMixDC-MEL were performed for 7 days at 37° C., 5% CO$_2$ in the presence of 1 µg/200 µL neutralizing anti-PD-L1 antibody or anti-PD-L1 sdAb. Isotype matched control antibodies or sdAb R3B23 were used as controls. Stimulation of T cells with DC-MEL was performed in analogy to the stimulation with TriMixDC-MEL, however, T cells were in this case restimulated on day 7 and analysis of T cell activation through dextramer staining (flow cytometry) and evaluation of the production of cytokines IFN-γ (ELISA, Thermo Scientific) was performed on day 14.

1.12. Proliferation Assay

PBMCs depleted from CD14$^+$ cells from healthy donor were labelled with 0.5 µM CellTrace Violet (Invitrogen). These cells (10E5) were co-cultured for 6 days with or without TriMixDC-MEL (4.8 µg each per 4×10E6 cells) or DC-MEL (4.8 µg Melan-A mRNA) at a effector:stimulator ratio of 10:1 in 200 µL IMDM containing 1% heat-inactivated human AB serum, PS, L-Glu and non-essential amino acids. T-cell proliferation was measured in flow cytometry as the dilution of the CellTrace Violet dye in the CD8+ T-cell population. Proliferation observed in cultures without TriMixDC-MEL or DC-MEL was considered as background.

1.13. Quantitative Reverse Transcriptase Polymerase Chain Reaction

Isolation of total RNA from CD8$^+$ T cells and its reverse transcription to cDNA was performed as described in Van der Jeught et al. 2014 (Oncotarget 5:10100-10113). To evaluate PD-1 mRNA levels, samples were subjected to a SYBRgreen (Thermofisher) based real-time PCR-analysis on a BIORAD device. Primers for amplification of PD-1 were as follow: reverse: 5'-CTTCTCTCGCCACTG-GAAAT-3' (SEQ ID NO:13) and forward: 5'-CCGCACGAGGGACAATAG-3' (SEQ ID NO:14) (Integrated DNA Technologies). Primers for the amplification of peptidylprolyl isomerase A (Ppia) were as follow: 5'-TT-CACCTTCCCAAAGACCAC-3' (SEQ ID NO:15) and 5'CAAACACAAACGGTTCCCAG-3' (SEQ ID NO:16) (Integrated DNA Technologies).

1.14. Preparation of Single Cell Suspensions from In Vivo Grown Tumours

Single cell suspensions were prepared after isolation of tumours from mice using the GentleMACS single cell isolation protocol (Miltenyi Biotec) in order to perform flow cytometry to analyze expression of PD-L1 on tumour cells.

1.15. Flow Cytometry

The procedure for staining of cellular surface markers was previously described (Breckpot et al. 2003, J Gene Med 5:654-667). All cells were acquired on the LSRFortessa flow cytometer (BD Biosciences) and data were analyzed with FACSDiva (BD Biosciences) or FlowJo (Tristar Inc.) software.

1.16. Statistical Analysis

Results are expressed as mean±standard error of the mean. A non-parametric Mann-Whitney U test was carried out to compare data sets. Sample sizes and number of times experiments were repeated are indicated in the figure legends. The number of asterisks in the figures indicates the statistical significance as follows: *$P<0.05$; $P<0.01$; *$P<0.001$.

1.17. 3D Spheroid Cytotoxicity Assay

624-MEL cells engineered to express eGFP and PD-L1, were plated at 200 cells in an ultra-low attachment 96-well plate (Costar®, ref 7007) and kept in culture for 1 day to form 3D spheroids. Subsequently, PBMCs stimulated for 24 hours with 10 ng/mL interleukin-2 (IL-2) (Peprotech) and 10 ng/mL anti-CD3 mAb (BioLegend, ref 317302) were added to the cells at a ratio of 1:50 in the presence of 3.6 µM avelumab, isotype-matched mAbs, K2, R3B23, or the combination of mAbs and sdAbs. In a separate assay, K2 or R3B23 were added every 24 hours to the co-culture after centrifuging the plate at 1200 rpm for 10 minutes and removing 50 µl of the co-culture. The reduction of total amount of green object area within each well containing eGFPPOS and PD-L1POS cells was evaluated every hour for seven consecutive days in an IncuCyte Zoom® live cell imaging system (EssenBio).

1.18. Evaluation of DC Maturation in Response to Endotoxins Present in sdAb Preparations To evaluate the effect of any endotoxins in the sdAb solutions, we incubated moDCs for 24 hours with 10 µg sdAb K2 or sdAb R3B23 at 37° C. and 5% $CO_2$. Untreated moDCs and moDCs treated with 1 ng/ml lipopolysaccharide [LPS] served as negative and positive controls, respectively. Up-regulation of maturation markers was evaluated in flow cytometry.

2. Results 2.1. Generation of High Affinity Single Domain Antibodies Specific for PD-L1 sdAbs were raised against PD-L1 through immunization of alpacas with recombinant human PD-L1 protein or with RAW624.7 macrophages that expressed mouse PD-L1. Peripheral blood lymphocytes from these alpacas were used to create a sdAb phage display library. Biopanning and screening on the immunogen was performed, resulting in a total of 42 sdAbs that were selected for binding to human and/or mouse PD-L1, both on recombinant proteins and on cells. Based on the amino acid sequence of the CDR1, 2 and 3 regions, these sdAbs were divided into 13 sequence families of which the mouse PD-L1 binding sdAbs were reported in Broos et al. 2017 (Oncotarget 8:41932). Several sdAbs bound to human PD-L1. Of these, the sequence family K, represented by sdAbs K2, K3 and K4, showed high affinity binding to human PD-L1 (FIG. 1, FIG. 2A-B). We showed that sdAbs K2, K3 and K4 bind with similar nanomolar affinity ($K_D$=5.2, 3.5 and 4.5 nM respectively) to human PD-L1 (FIG. 2 B-D). Furthermore, we showed that sdAbs K2, K3 and K4 and avelumab were able to bind with human PD-L1 expressed on HEK293T cells (FIG. 2C). The affinity of avelumab for human PD-L1 was determined as $K_D$=1.6 nM.

Figure 3B:
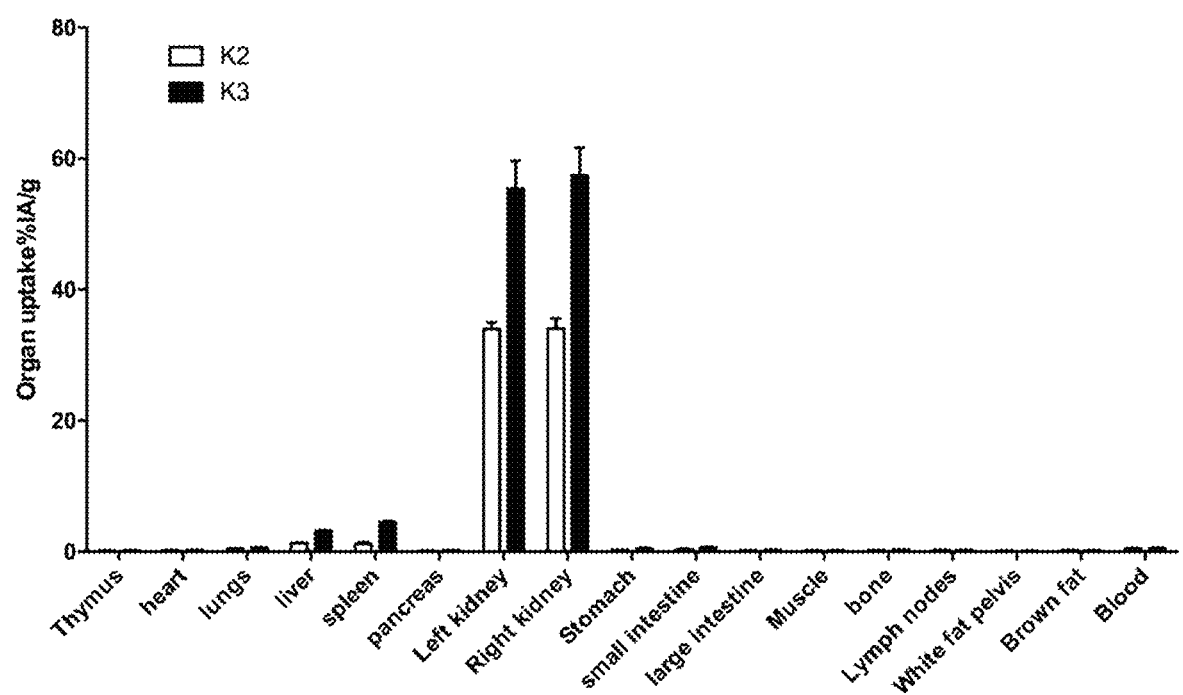

2.2. The PD-L1 Specific sdAb K2 Generates Strong Positive Contrast in SPECT/CT Imaging We radiolabelled sdAb K2, K3 and K4 with $^{99m}Tc$ through complexation of the $^{99m}Tc$-tricarbonyl with its HIS-tag followed by purification by filtration and NAP-5 column. This resulted in a radiochemical purity of >98% for sdAb K2 and K3, however, yielded low radiochemical purity (93%) for sdAb K4 (Table 1). Therefore, sdAb K4 was excluded for further analysis. The biodistribution of sdAbs K2 and K3 was evaluated in healthy C57BL/6 mice using SPECT/CT imaging, showing low signals in the liver, kidneys and bladder (FIG. 3A). These signals are a consequence of the metabolization and renal excretion typically observed in sdAb mediated imaging. Quantification of tracer uptake by ex vivo biodistribution analysis, revealed that uptake of sdAb K2 and K3 in liver (1.292±0.063 and 3.191±0.060% IA/g, respectively), left kidney (33.99±1.014 and 55.39±4.27% IA/g) and right kidney (34.06±1.530 and 57.42±4.219% IA/g) were extremely low when compared to values typically obtained with sdAbs used for imaging of other marker (Broisat et al. 2012, Circ Res 110:927-937) (FIG. 3B). We selected sdAb K2 for further analysis, because this sdAb showed the lowest uptake in liver and kidneys.

TABLE 1

| sdAb | Nap5 (mCi) | Eluate (mCi) | Filter (mCi) | filtrate mCi | Radiochemical purity after purification |
|---|---|---|---|---|---|
| K2 | 3.49 | 23.54 | 3.61 | 19.86 | 98% |
| K4 | 12.06 | 4.45 | 2.03 | 2.30 | 93% |
| K3 | 5.23 | 22.51 | 5.82 | 16.24 | 98% |

Figure 4A:
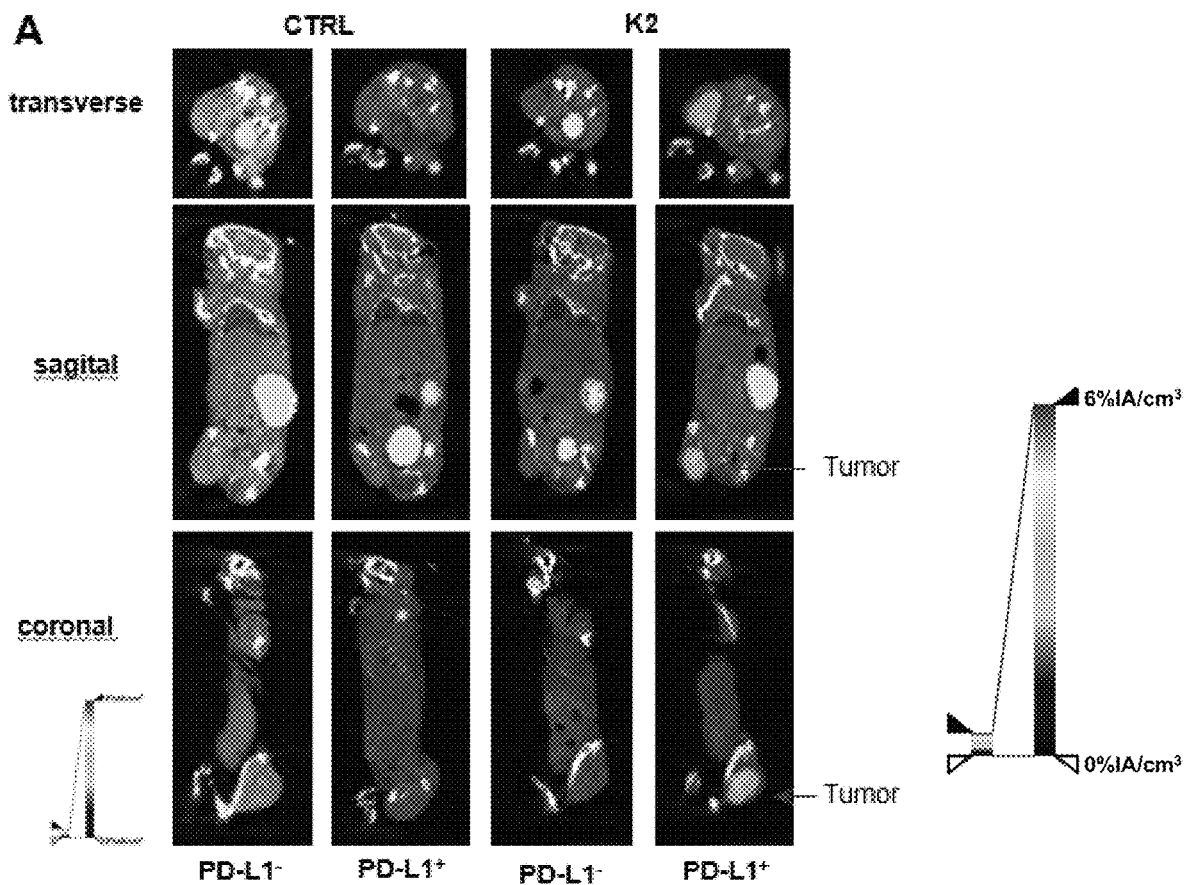
FIGS. 4A-4C.
Figure 7A:
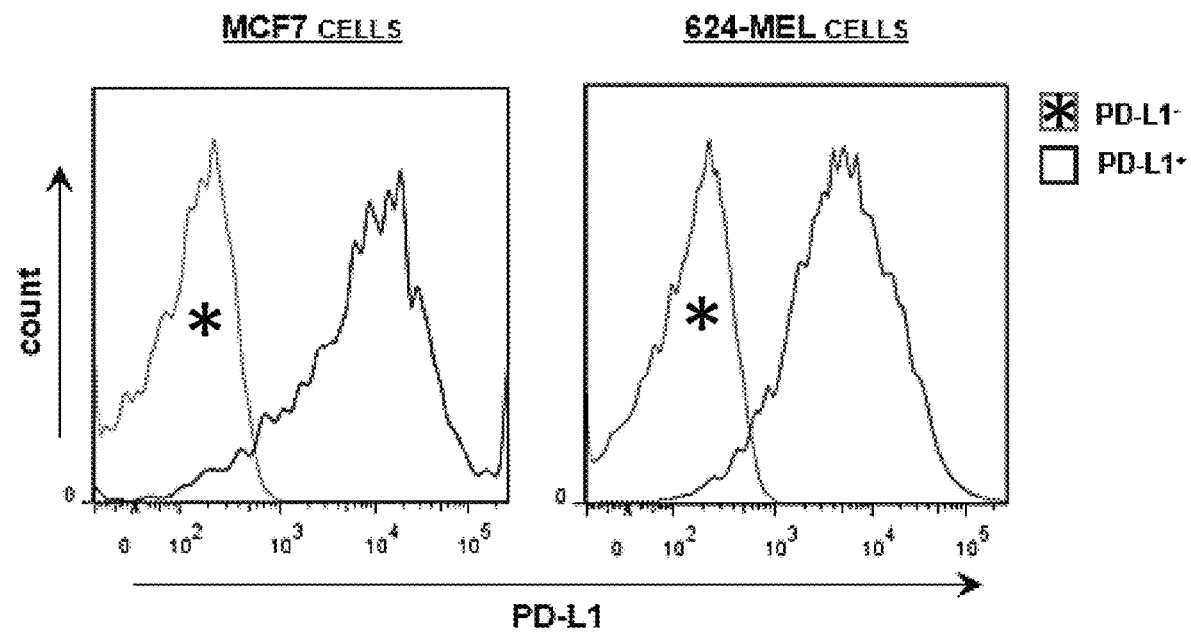
Figure 8A:
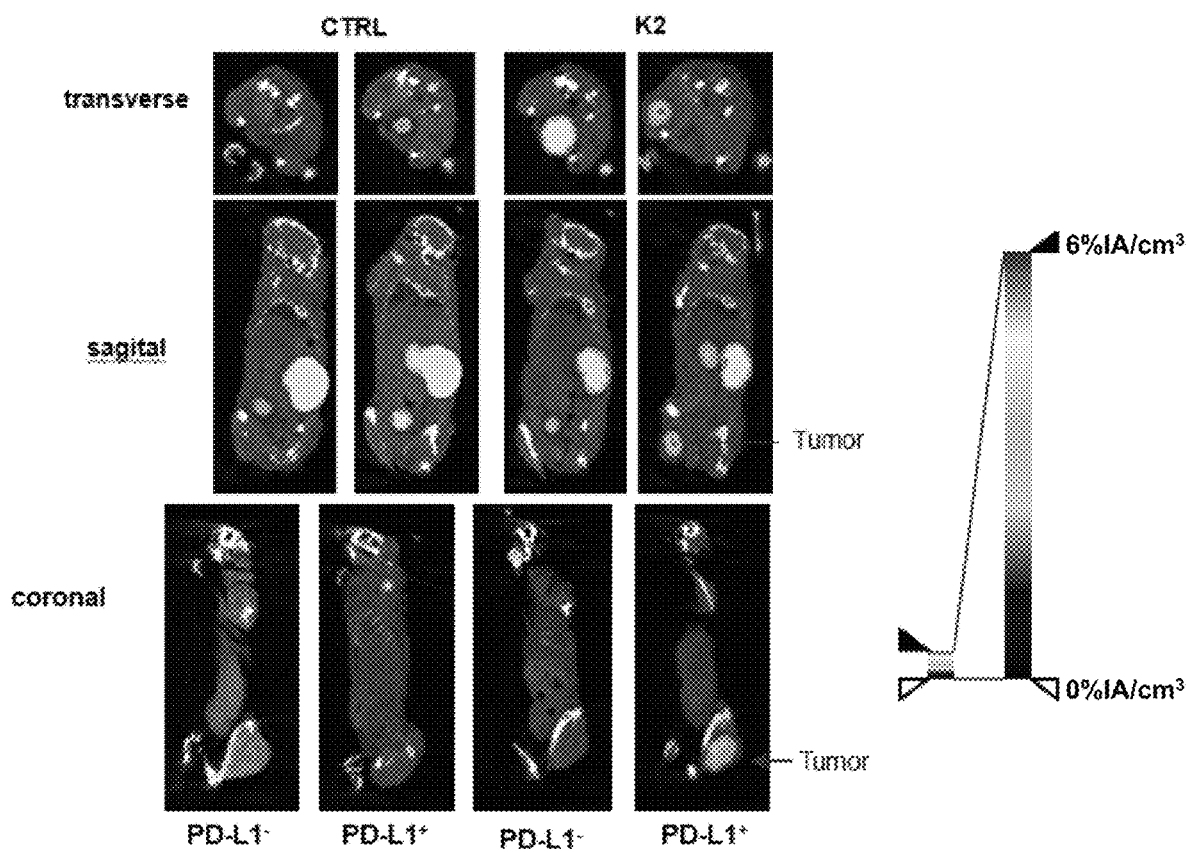
FIGS. 8A-8C.
Figure 8B:
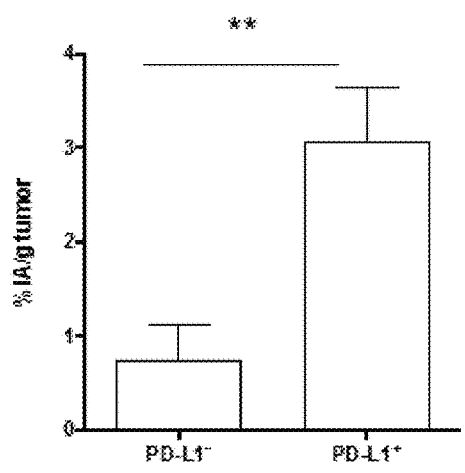
Figure 8C:
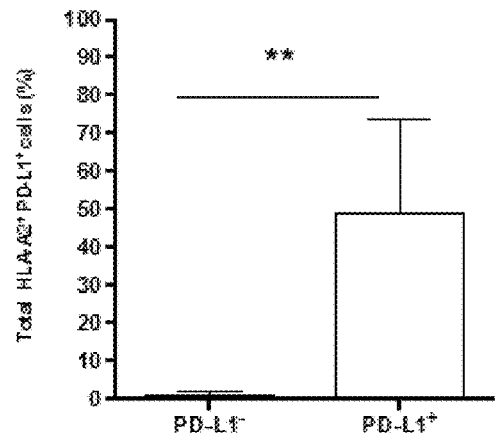

We transplanted MCF7 breast cancer and 624-MEL melanoma cells, or their PD-L1 engineered counterparts subcutaneously in athymic nude mice (FIG. 7A-B). SPECT/CT imaging was performed, generating strong positive contrast images in mice bearing PD-L1$^+$ tumours (FIG. 4A & FIG. 8A). Ex vivo analysis (gamma-counting) confirmed the accumulation of sdAb K2 in PD-L1$^+$ MCF7 and 624-MEL tumours (3.07±0.24 and 4.86±0.73% IA/g, respectively) when compared to PD-L1$^-$ MCF7 and 624-MEL tumours (0.73±0.15 and 0.85±0.24% IA/g, respectively) (FIG. 3B & FIG. 8B). Using flow cytometry we confirmed the expression of PD-L1 on the tumour cells (FIG. 3C & FIG. 8C). See also FIGS. 13 and 14.

Figure 5A:
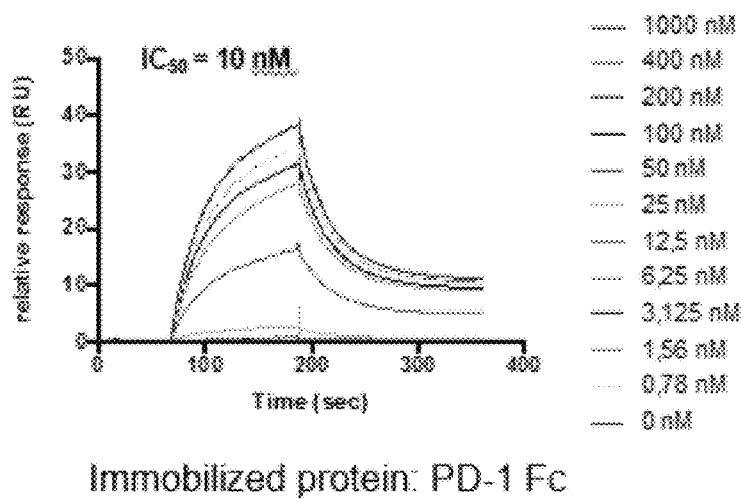
FIGS. 5A-5E.
Figure 5B:
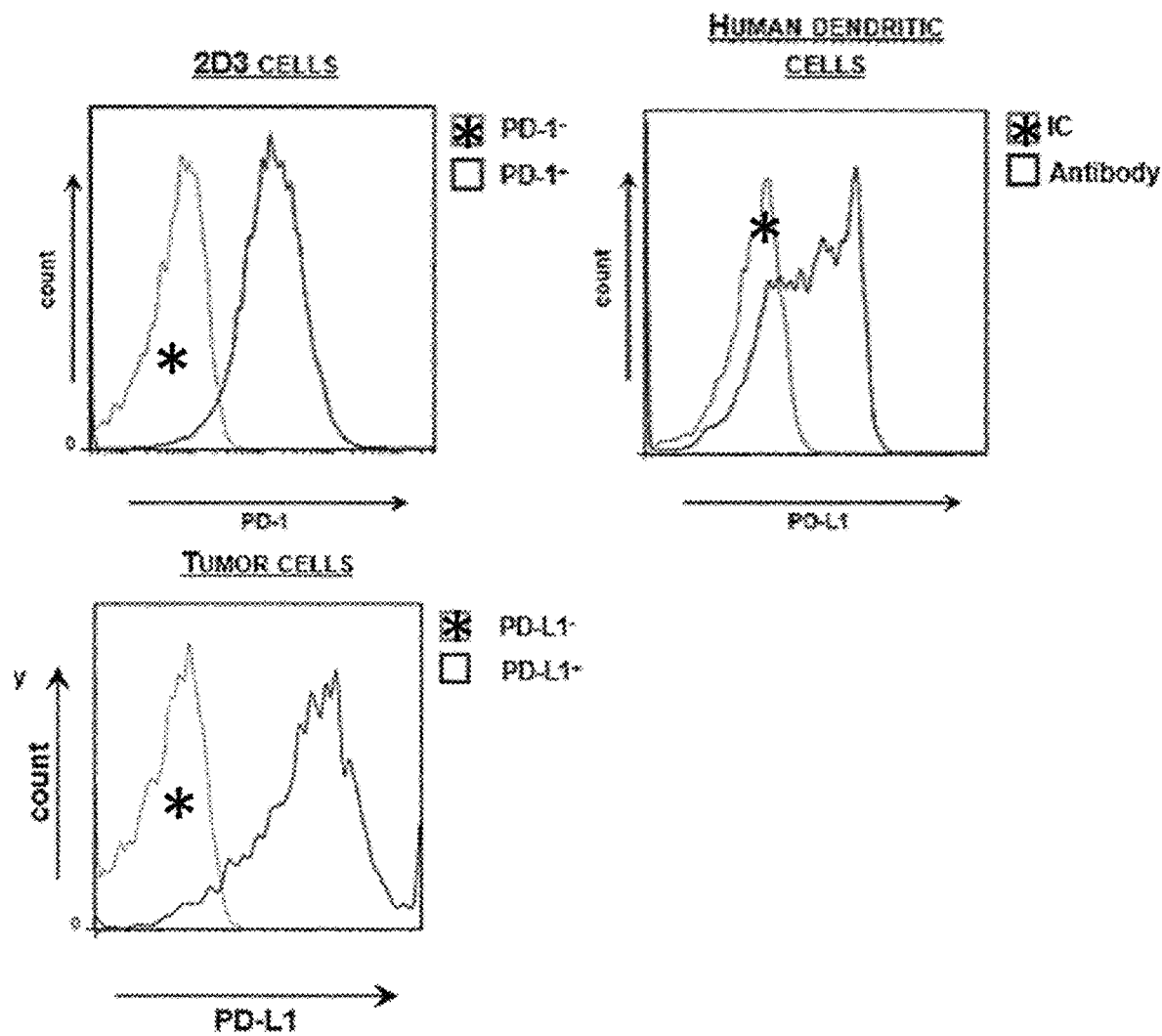
Figure 5C:
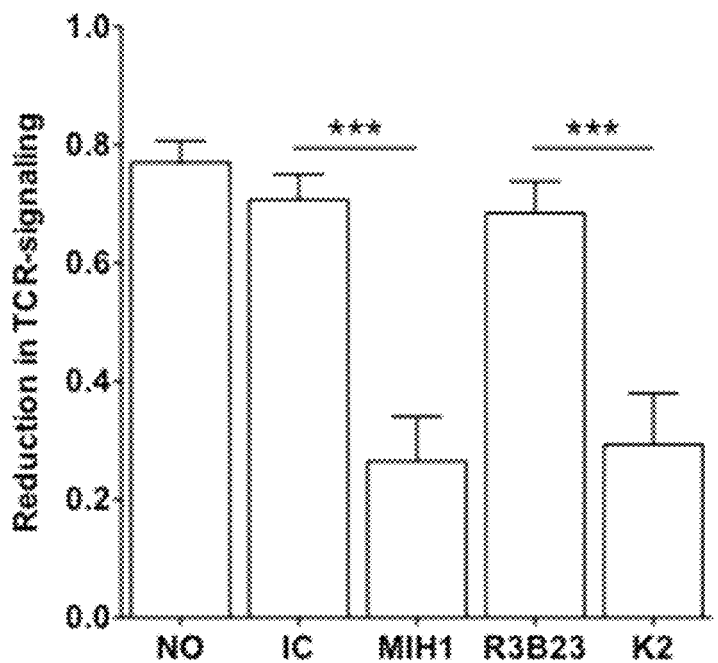
Figure 5D:
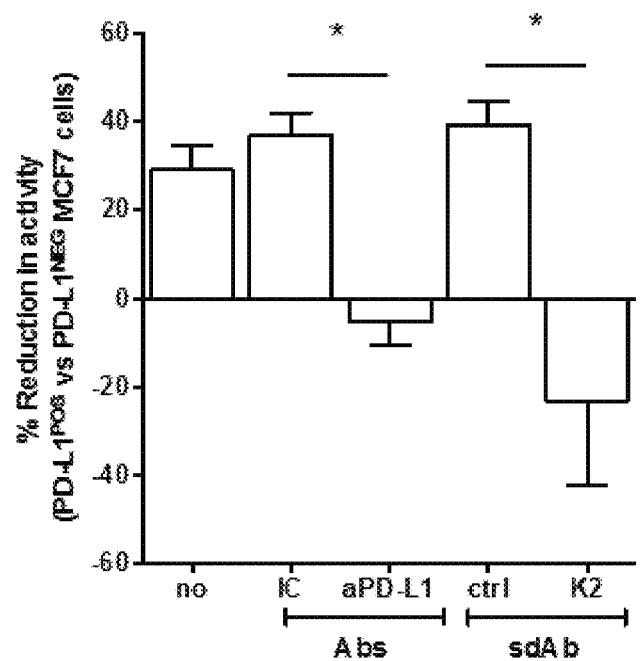
Figure 5E:
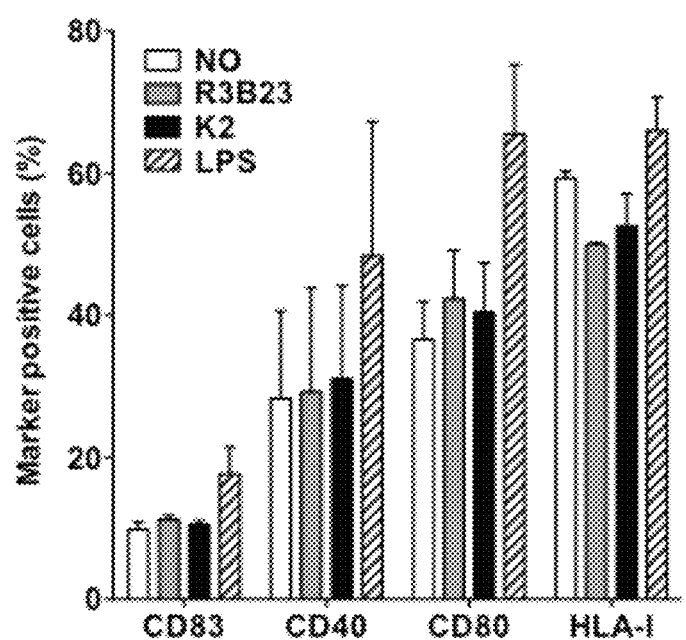

2.3. sdAb K2 Facilitates Activation of 2D3 Cells by Dendritic Cells and Tumour Cells Because sdAb K2 showed high capacity to penetrate tumours, we decided to evaluate whether it has blocking activity and therefore might be used as a therapeutic agent. We showed in SPR that sdAb K2 is able to reduce the interaction between PD-1:PD-L1 with an $IC_{50}$ value of 9.5 nM (FIG. 5A). We previously optimized a functional cell based assay to evaluate the blocking capacity of mAbs targeting PD-1 or PD-L1, using 2D3 cells engineered to express a specific TCR and PD-1 (Versteven et al, Oncotarget, under review). Therefore, we decided to use this platform to evaluate the blocking ability of sdAb K2 using HLA-A2$^+$ moDCs or MCF7 cells pulsed with the gp100$_{280-288}$ peptide as cells to activate PD-F or PD-1$^+$ 2D3 cells expressing the TCR recognizing gp100$_{280-288}$ in the context of HLA-A2 (FIG. 5B). We observed that the activation of 2D3 cells as measured by their expression of eGFP in flow cytometry was inhibited upon interaction of PD-1:PD-L1, and that this inhibition could be alleviated through addition of blocking anti-PD-L1 mAbs [MIH, IgG1) or sdAb K2 but not isotype matched mAbs or sdAb R3B23 (recognizing the 5T2MM paraprotein) (FIG. 5C-D). Comparable results as with mAb MIH1 and sdAb K2 were obtained with the IgG1 mAb avelumab (results not shown). To exclude that the activation of 2D3 cells in the context of moDC stimulation was due to maturation of the moDCs through endotoxins present in the sdAb preparations (3.96EU/mL), we compared the phenotype of moDCs that were untreated with moDCs treated with sdAb K2 or sdAb R3B23. Upregulation of activation associated phenotypic markers like PD-L1, CD83, CD40, CD80 and MHC-I was only observed when moDCs were treated with LPS ((FIG. 5E). These results indicate that the increase in TCR-signalling in PD-1$^{pos}$ 2D3 cells during antigen-presentation by PD-L1$^{pos}$ moDCs in the presence of sdAb K2 is due to inhibition of the PD-1/PD-L1 interaction and not due to an increase in HLA-I expression, therefore antigen presentation.

In conclusion sdAb K2 potently inhibits the interaction between PD-1/PD-L1 during antigen presentation by moDCs and as such enhances TCR-signalling, as shown by the NFAT-mediated up-regulation of eGFP in PD-1$^{pos}$ 2D3 cells.

Figure 16A:
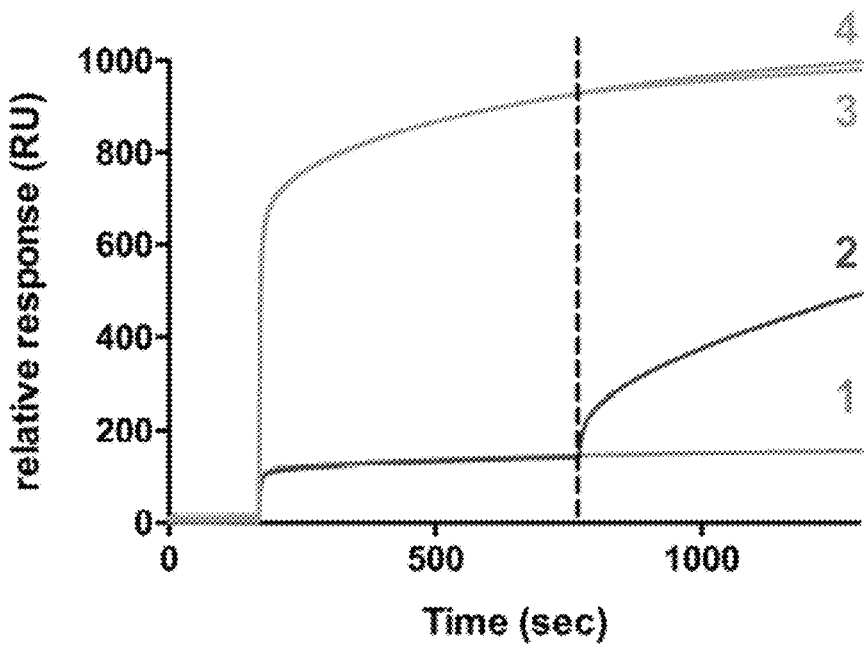
Figure 16B:
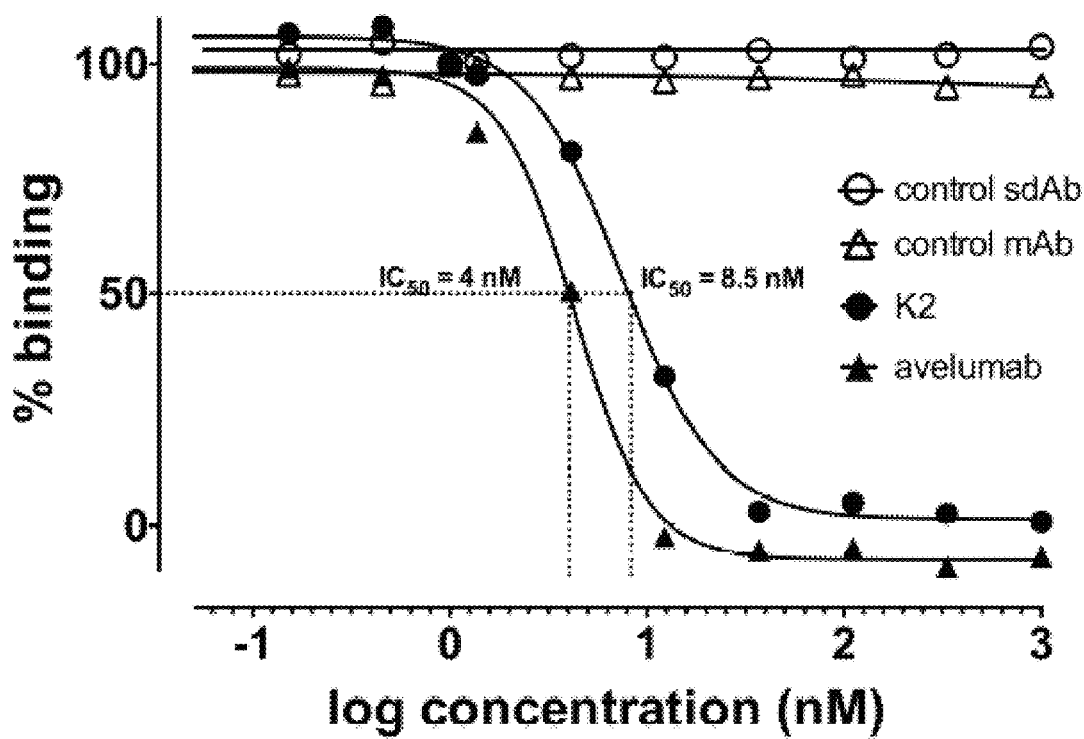
Figure 16C:
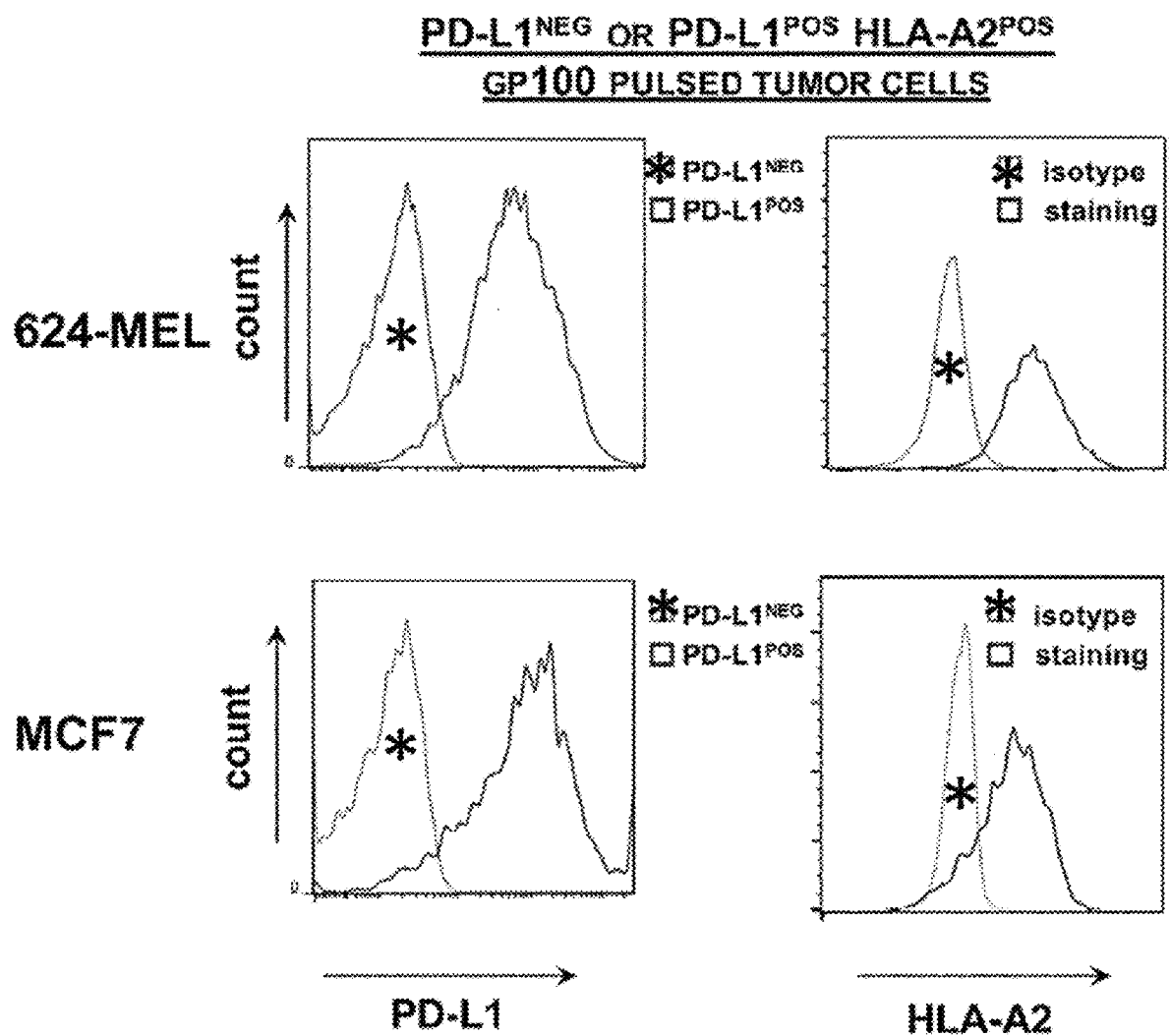

The above platform was further relied on to evaluate the blocking ability of sdAbK2, as schematized in FIG. 16C,D. HLA-A2POS PD-L1POS or PD-L1NEG 624-MEL melanoma cells or MCF7 breast cancer cells (FIG. 16C) were pulsed with the gp100$_{280-288}$ peptide and used to activate PD-1POS 2D3 cells expressing the TCRαβ recognizing gp100$_{280-288}$ in the context of HLA-A2 (FIG. 16D). In the absence of PD-L1 blocking agents (FIG. 16E-F, condition 'no'), co-culture of PD-1POS 2D3 cells with PD-L1POS 624-MEL tumour cells reduced the percentage of eGFPPOS cells as compared to co-culture with PD-L1NEG tumour cells. This reflects the interaction of PD-1 on 2D3 cells with PD-L1 on melanoma cells, which inhibits TCR signalling (Karwacz et al. 2011, EMBO Mol Med 3:581-592). The inhibition could be alleviated through addition of avelumab or sdAb K2 but not of isotype matched mAbs or R3B23 (FIG. 16E). A similar experiment was performed using HLA-A2POS PD-L1POS or PD-L1NEG MCF7 breast cancer cells as stimulator cells, confirming in another tumour model that sdAb K2 is able to block the interaction between PD-1 and PD-L1 and as such enhances TCR signalling (FIG. 16F).

2.4. sdAb K2 Facilitates Activation of T Cells by Dendritic Cells

We previously developed a DC-manufacturing protocol in which moDCs were electroporated with 4 different mRNA molecules. More-specifically mRNA encoding for a melanoma antigen fused to an HLA-II targeting signal, and 3 mRNA molecules encoding for proteins that enhance the immunogenicity of the moDCs; CD40 ligand, CD70 and a constitutively active toll-like receptor 4, together referred to as TriMix. These moDCs are referred to as TriMixDCs, and were shown to be potent activators of antigen-specific CD8$^{pos}$ T cells (Bonehill et al. 2009, Clin Cancer Res 15:3366-3375). Moreover, these TriMixDCs induce durable objective responses in 4 out of 15 [26.7%] pre-treated advanced-stage melanoma patients, thereby being among the most potent DC-vaccines described in literature (Wilgenhof et al. 2013, Ann Oncol 24:2686-2693).

Figure 6A:
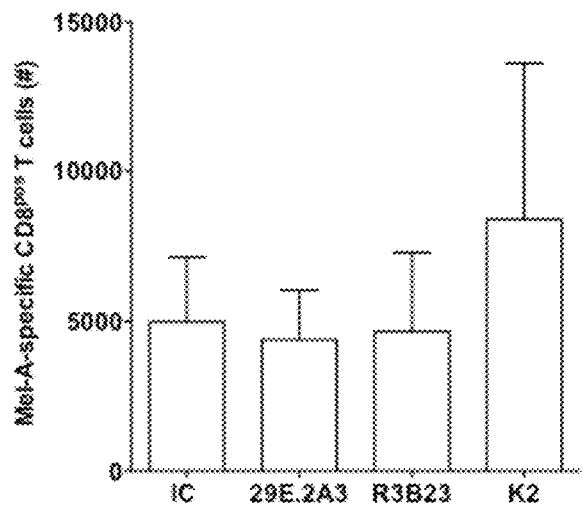
Figure 6B:
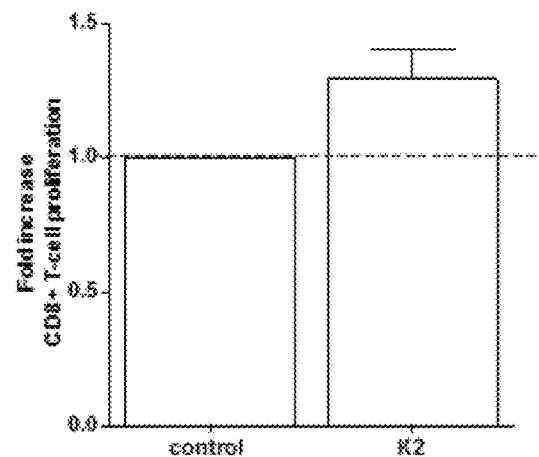
Figure 6C:
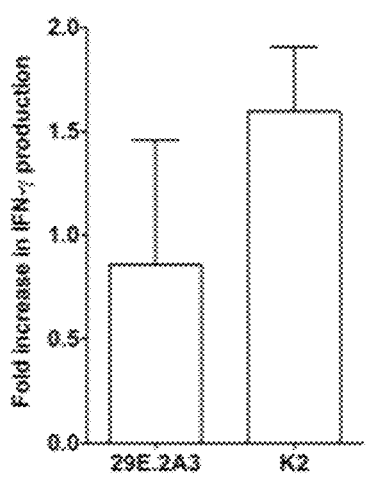
Figure 6D:
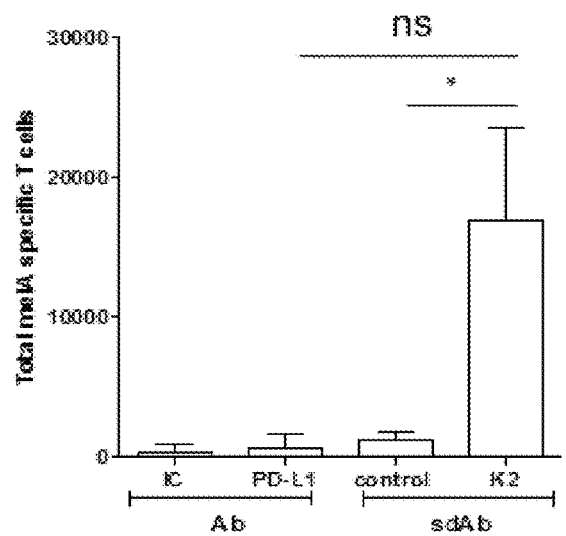
Figure 9A:
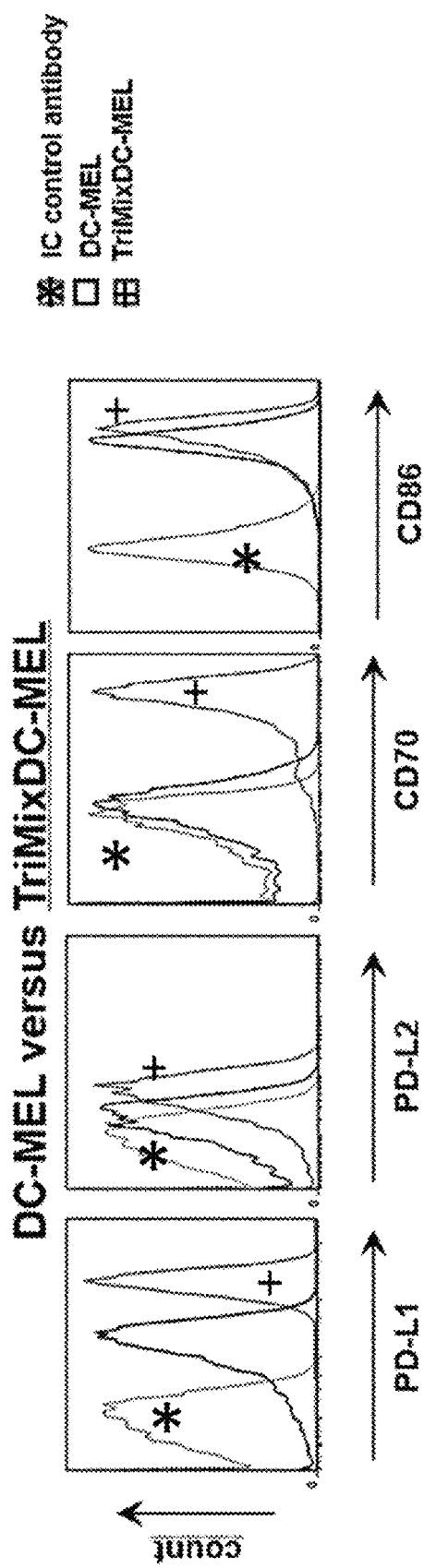
FIGS. 9A-9C.
Figure 9B:
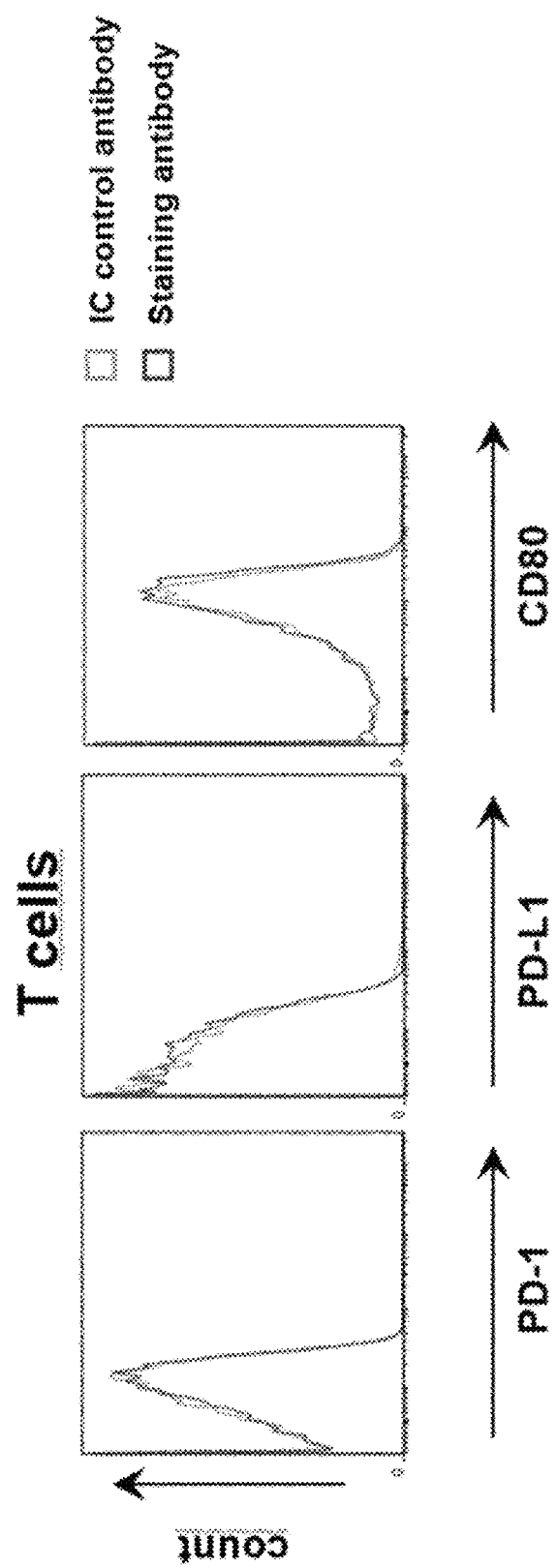
Figure 9C:
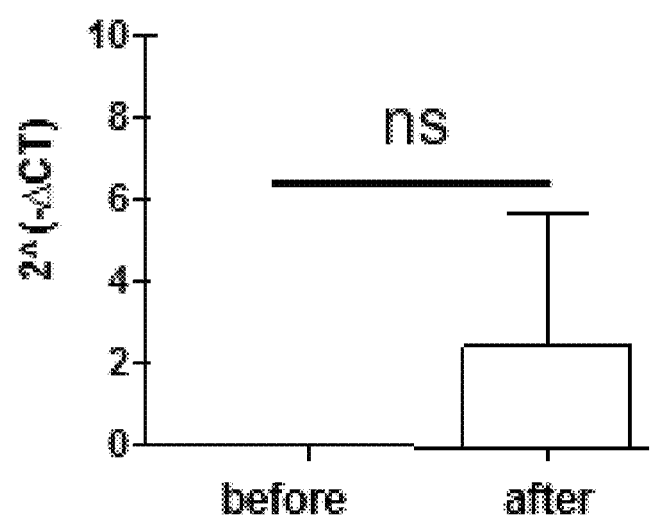

Vaccination with moDCs in particular TriMixDC-MEL was shown to be a promising strategy to treat patients with melanoma (Wilgenhof et al. 2013, Annals Oncol 24:2686-2693; Van Lint et al. 2014, Cancer Immunol Immunother 63:959-967; Wilgenhof et al. 2015, Cancer Immunol Immunother 64:381-388). Since TriMixDC-MEL represent mature, PD-L1 expressing moDCs, we assessed whether we could improve this vaccination strategy by supplementing the TriMixDC-MEL vaccine with sdAb K2 during the antigen presentation process (FIG. 9A). We stimulated CD8$^+$ T cells from HLA-A2-positive healthy donors with TriMixDC-MEL (TriMixDC modified to present Melan-A, FIG. 6G) in the presence of blocking anti-PD-L1 mAbs (mAb 29E.2A3, IgG2b), sdAb K2, isotype matched mAbs or sdAb R3B23. In these cultures, CD8$^+$ T cells showed no expression of PD-1, PD-L1 or CD80 at the start of culture as assessed by flow cytometry (FIGS. 6H and 9B). Quantitative real time PCR confirmed the lack of PD-1 at the start of culture, however, showed upregulation of PD-1 during stimulation (FIG. 9C). We showed that the presence of sdAb K2 or the blocking anti-PD-L1 mAb 29E.2A3 during antigen presentation by TriMixDC-MEL to CD8+ T-cells did not significantly increase the number of Melan-A specific T cells. Corroborating these data, no significant increase in secretion of IFN-γ by Melan-A-specific T cells was observed in the presence of mAb 29E.2A3 compared to isotype-matched control mAb, or in the presence of sdAb K2 compared to sdAb R3B23 (FIG. 6A-C). These results suggest that the co-inhibitory signal provided by PD-L1 is a lesser determinant in the degree of T-cell activation when co-stimulatory signals such as CD70, CD86, . . . , are abundantly provided by the antigen-presenting cells, in this case TriMixDC-MEL.

Figure 6I:
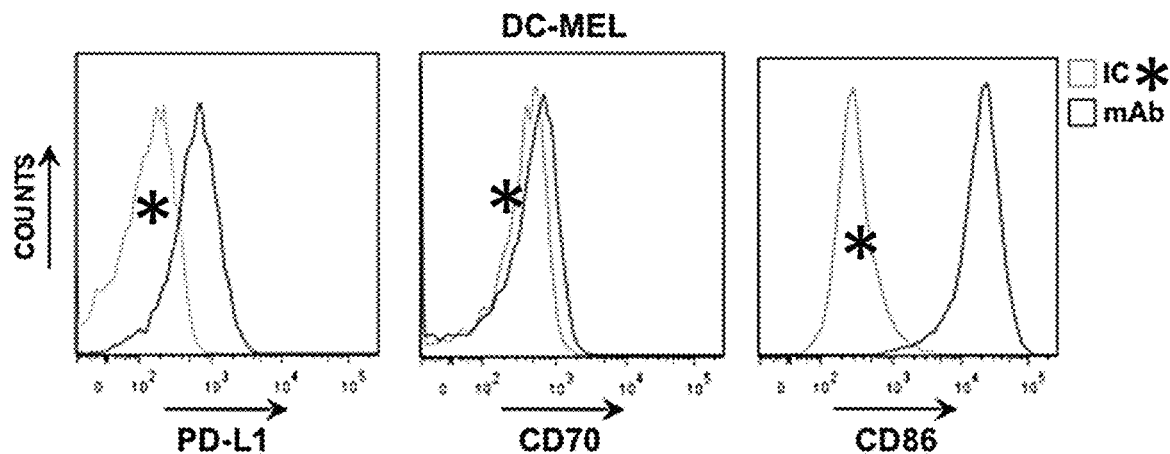

We hypothesized that the lack of a statistical significant increase in T-cell activation could be due to the fact that TriMixDC-MEL, which express the strong co-stimulatory molecules CD70, CD80 and CD86, are already optimally equipped to activate T cells, while this might not be the case for DC vaccines that are less mature, and even lack CD70, CD80 and CD86 expression. Therefore, we repeated the T-cell stimulation experiment using DC-MEL, moDCs electroporated with Melan-A mRNA as antigen presenting cells (FIGS. 6I and 9A). Two rounds of stimulation were performed with these less mature, Melan-A presenting moDCs to obtain sufficient Melan-A specific CD8$^+$ T cells for analysis both in the presence of blocking anti-PD-L1 mAbs (29E.2A3), sdAb K2, isotype matched mAbs or sdAb R3B23. We showed that the presence of sdAb K2 but not the mAb resulted in significantly higher amounts of Melan-A specific T cells, which showed higher proliferation and secretion of IFN-γ (FIGS. 6D-F, and 6J).

It was previously shown that an increase in antigen-specific CD8$^{pos}$ T cells in cultures with PBMCs was more pronounced when using mAbs with an IgG1 isotype [avelumab, MIH1] when compared to mAbs with an IgG2b isotype [29E.2A3] (Grenga et al. 2016, Clin Transl immunol 5:e83). Therefore, we repeated these experiments using avelumab as an IgG1 blocking mAb. Similar to the findings with the IgG2b mAb 29E.2A3, we did not observe enhanced CD8$^{pos}$ T-cell activation by DC-MEL in the presence of avelumab [data not shown].

Figure 11A:
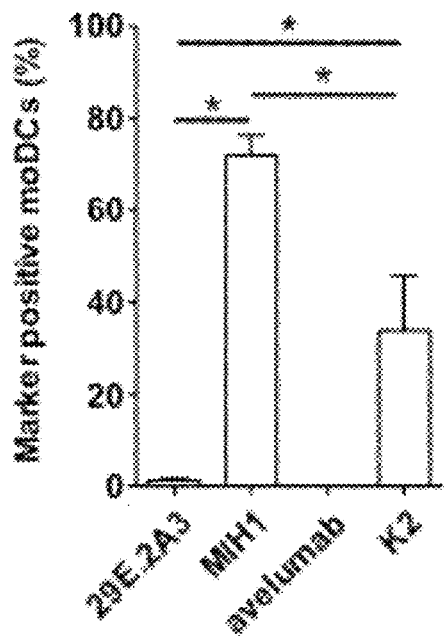
FIG. 11. Binding of anti-PD-L1 mAbs and sdAb K2 on PD-L1$^{pos}$ moDCs versus 293T cells. Graph summarizing the percentage PD-L1$^{pos}$ moDCs (A) or 293T cells (B) detected in flow cytometry upon staining with the mAbs 29E.2A3, MIH1 or avelumab, or sdAb K2. Cells stained with isotype-matched control mAbs or sdAb R3B23 served as a control [n=3].
Figure 11B:
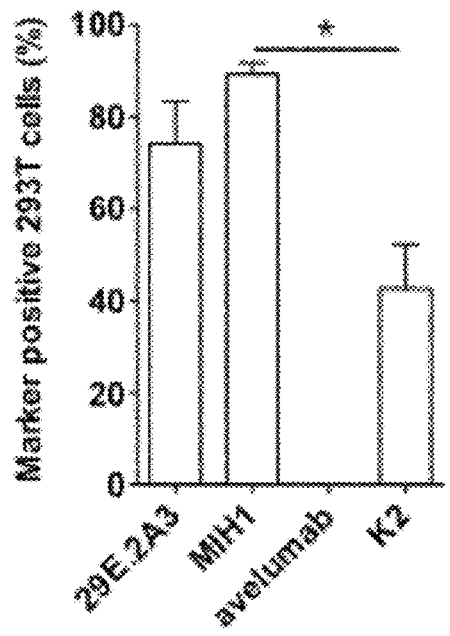
Figure 12A:
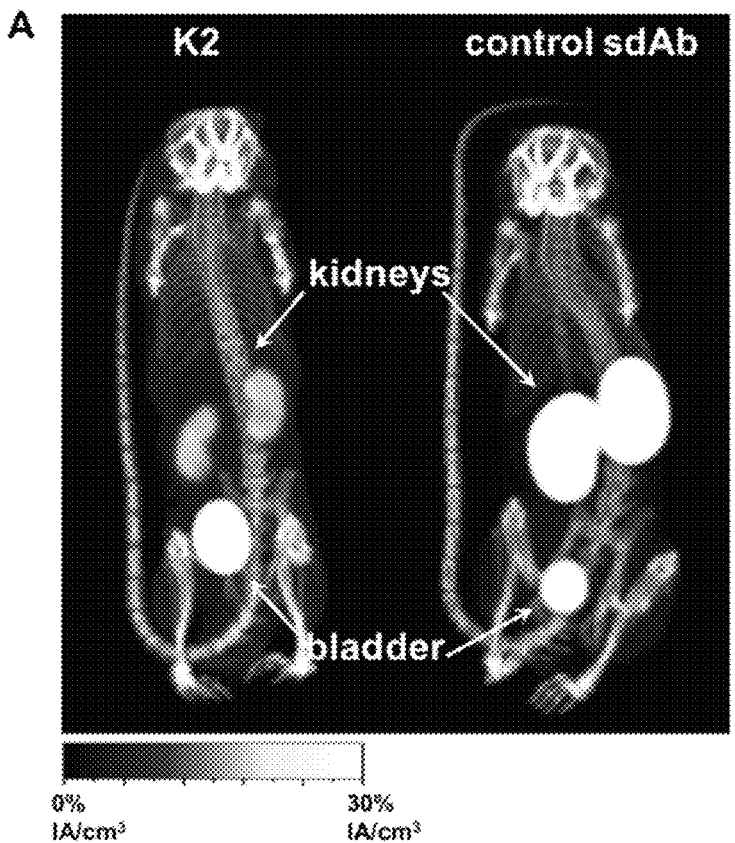
FIGS. 12A-12B. Radiolabelled anti-human PD-L1 sdAb K2 shows low non-specific signals in healthy mice.
Figure 12B:
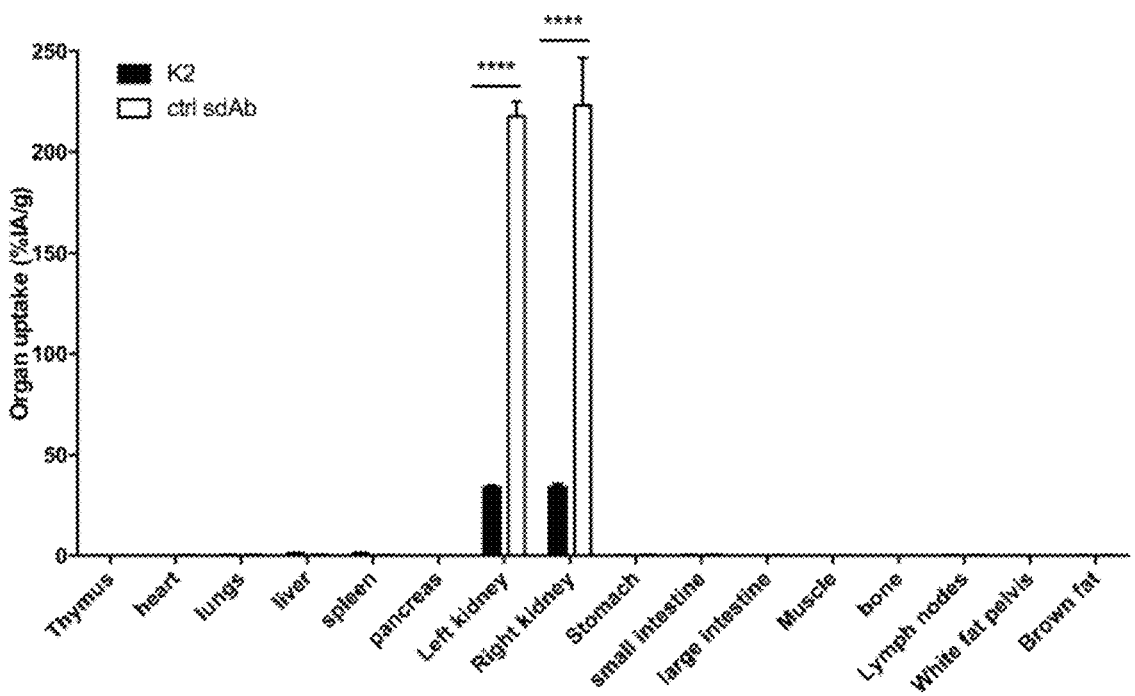
Figure 13A:
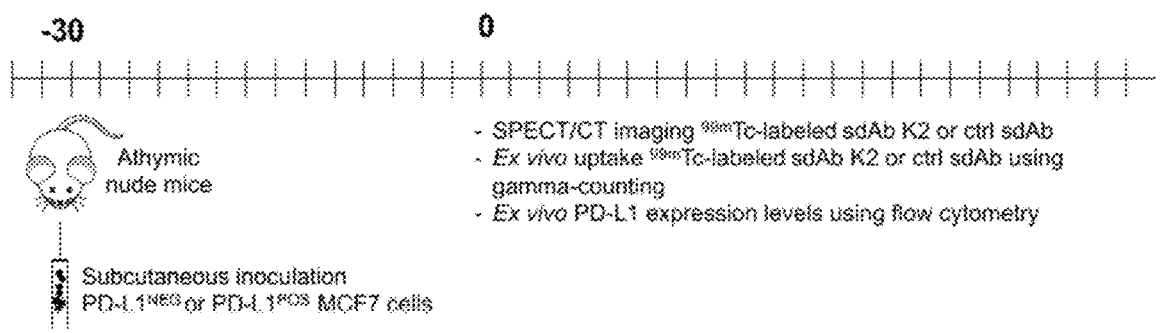
FIGS. 13A-13E. Radiolabelled sdAb K2 allows visualization of human PD-L1 expressing breast tumours by nuclear imaging.
Figure 13B:
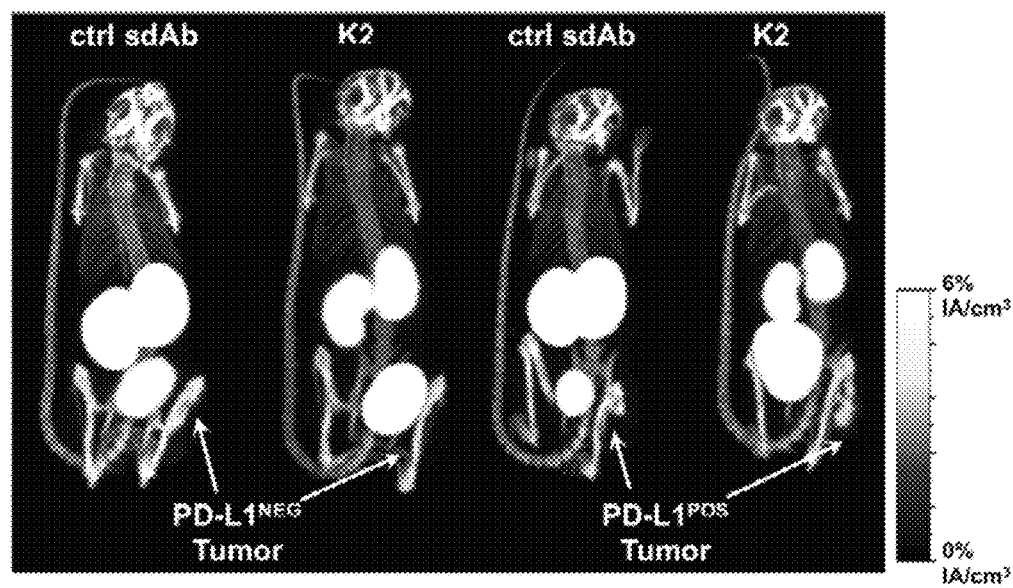
Figure 13C:
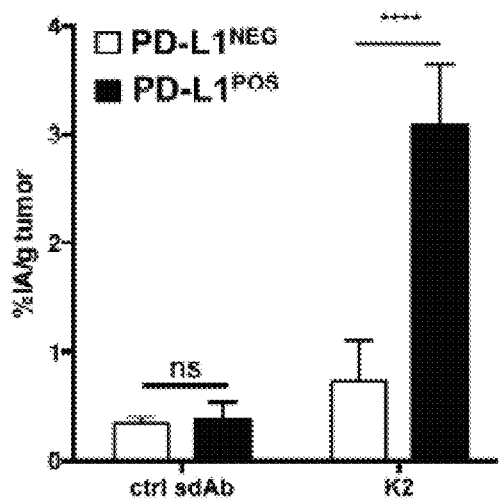
Figure 13D:
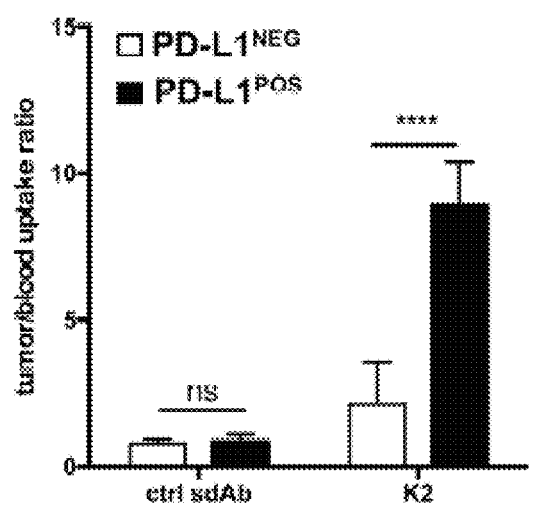
Figure 13E:
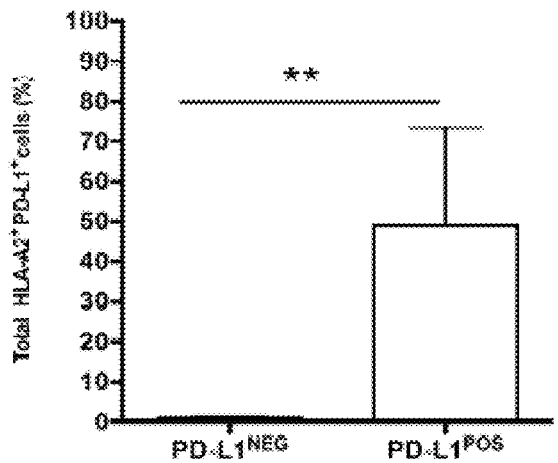
Figure 14A:
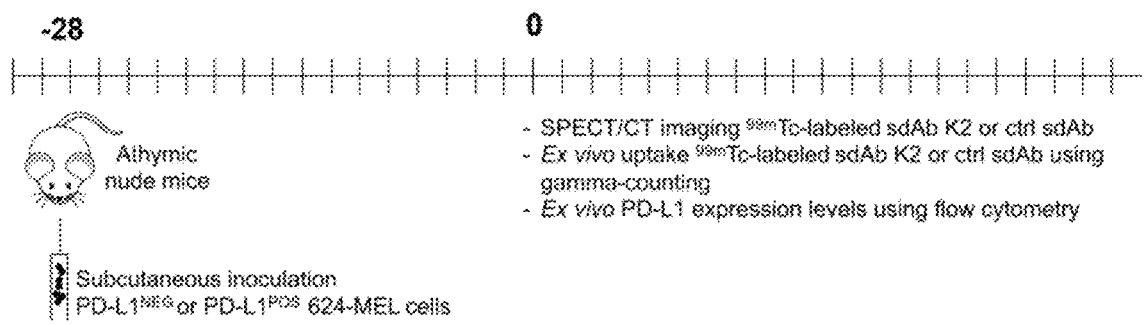
FIGS. 14A-14E. Radiolabelled sdAb K2 allows visualization of human PD-L1 expressing melanoma tumours by nuclear imaging.
Figure 14B:
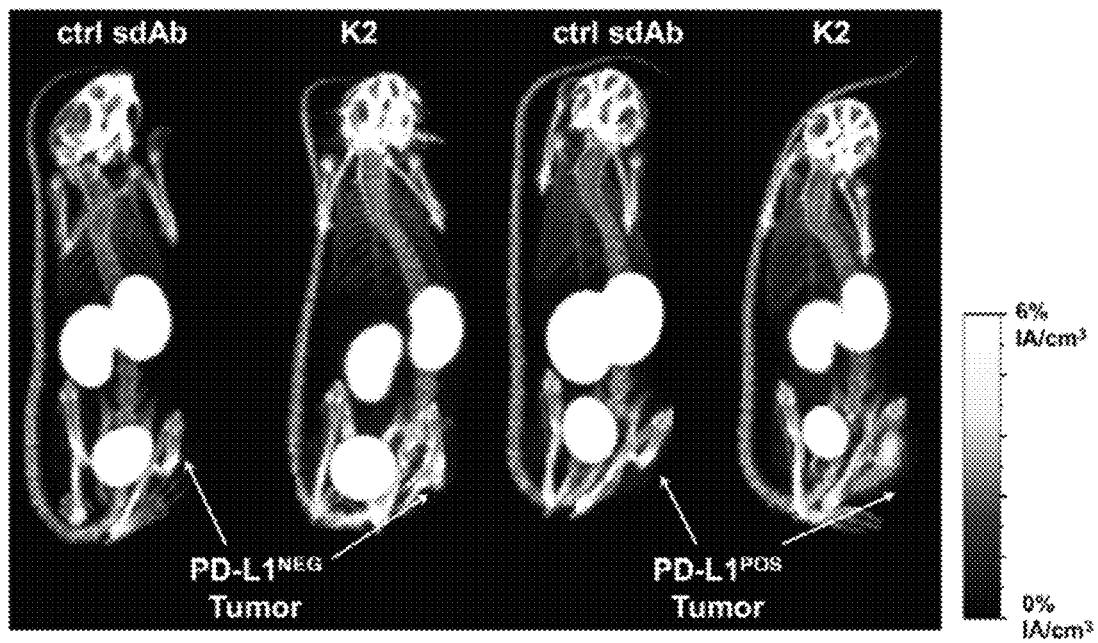
Figure 14C:
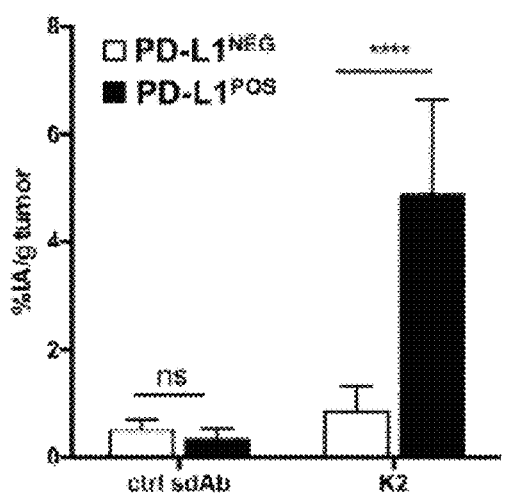
Figure 14D:
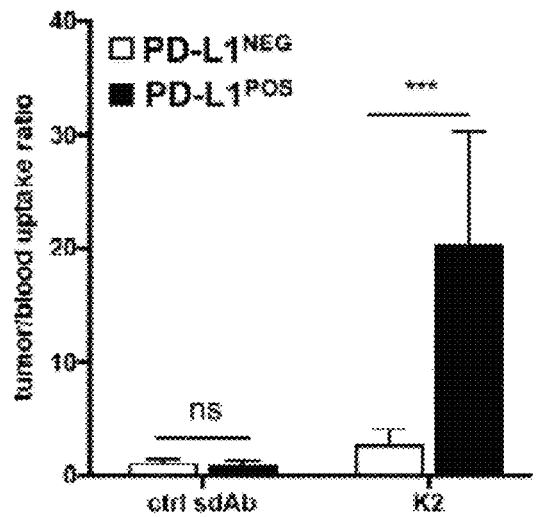
Figure 14E:
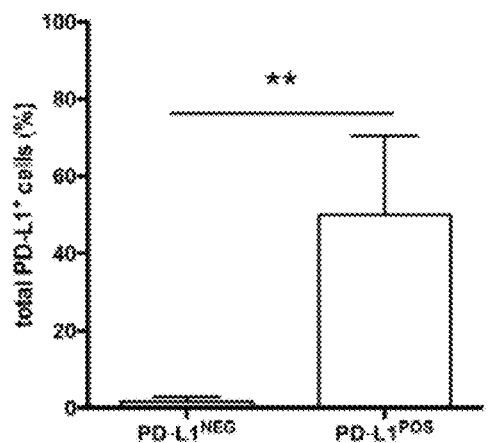

It was unexpected that the anti-PD-L1 mAbs used in the DC-MEL study, both 29E.2A3 and avelumab, were unable to enhance the activation of Melan-A-specific CD8$^{pos}$ T cells by DC-MEL, as both have been described as a blocking mAbs, and have been previously used to enhance activation of antigen-specific CD8$^{pos}$ T cells by PBMCs (Grenga et al. 2016, Clin Transl immunol 5:e83). In search for an explanation for this lack of effect, we studied binding of mAbs 29E.2A3 and avelumab to moDCs. Staining of moDCs with mAb MIH1 and sdAb K2 were performed for comparison. We observed that mAb MIH1 was the most efficient in detecting PD-L1 on moDCs followed by sdAb K2, avelumab and mAb 29E.2A3 [FIG. 11a]. In fact, in flow cytometry mAb 29E.2A3 was not proficient in staining PD-L1. In contrast, efficient staining of PD-L1 on PD-L1$^{pos}$ 293T cells was observed [FIG. 11b], suggesting a different sensitivity of mAb 29E.2A3 for binding to PD-L1 on immune cells versus non immune cells. Such differences in immune cell versus tumour cell sensitivity of mAbs used for detection of PD-L1 in immunohistochemistry (IHC) was previously described (Schats et al. 2018, Arch Pathol Lab Med 142:982-991).

In conclusion, these results suggest that the inability and low efficacy to bind PD-L1 on moDCs when compared to binding of PD-L1 on non-immune cells explains the lack of effect with mAb 29E.2A3 and avelumab, respectively. Furthermore, the results generated with sdAb K2 in the context of TriMixDC-MEL and DC-MEL-mediated CD8$^{pos}$ T-cell activation suggest that in the absence of strong co-stimulatory signals, PD-L1 is a major determinant of T-cell activation. Finally, the data generated with DC-MEL and sdAb K2 provide a rationale for the inclusion of sdAb K2 in DC-based immunotherapy strategies.

The inhibitory function of PD-1/PD-L1 interaction during antigen presentation by DCs to T cells is generally recognized, pinpointing this inhibitory pathway as an attractive therapeutic target to enhance the potency of DC-vaccines. Several strategies have been successfully employed in preclinical studies to interfere with PD-1/PD-L1 interactions during antigen presentation by DCs to CD8$^{pos}$ T cells. In particular the use of mAbs in combination with DC-vaccination has found its way to the clinic, as evidenced by a number of clinical trials in a range of malignancies (Versteven et al. 2018, Front Immunol 9:394). However, the immune synapse clears and even excludes molecules above a certain size, including mAbs (Cartwright et al. 2014, Nat Commun 5:5479). Therefore, the use of small-sized, blocking PD-1/PD-L1 agents might be more advantageous. Described herein are human PD-L1-specific sdAbs, more specifically sdAb K2, as a PD-1/PD-L1 neutralizing moiety with high target specificity and affinity. Its small size (≈15 kDa) and therefore predicted high potential to penetrate within cell-cell interfaces like immune synapses (Cartwright et al. 2014, Nat Commun 5:5479), make it an interesting candidate for implementation in combination therapy with DCs.

We showed that sdAb K2 could shift the balance between stimulatory and inhibitory signals during the early stage of T-cell activation when using DCs with a low stimulatory profile. Although DC-activation, here achieved through delivery of TriMix mRNA, results in enhanced expression of PD-L1, we could not observe a significant increase in CD8$^{pos}$ T-cell activation when sdAb K2 was added during the antigen presentation by mature DCs. This might be explained by the fact that activation of moDCs coincides with up-regulation of various co-stimulatory molecules, creating an environment in which co-stimulatory signals supersede co-inhibitory signals. This finding corroborates previous studies in which moDCs of different potency were used to activate allogeneic CD4$^{pos}$ T cells in the presence of PD-L1 blocking mAbs (Brown et al. 2003, J Immunol 170:1257-1266), and suggests that blockade of the PD-1/PD-L1 pathway has most impact in conditions of 'weak' stimulation.

We were unable to show any benefit of adding mAbs to the moDC-CD8$^{pos}$ T-cell co-cultures. This is in contrast to other studies reporting on the use of avelumab and/or mAb 29E.2A3 to enhance the activation of human T-cell populations of healthy donors (Grenga et al. 2016, Clin Transl immunol 5:e83; Brown et al. 2003, J Immunol 170:1257-1266). Several reasons can explain this discrepancy. Grenga et al. 2016 (Clin Transl immunol 5:e83) studied interaction between PBMCs and CD8$^{pos}$ T cells, rather than moDCs and CD8$^{pos}$ T cells, showing that in this setting, activation of virus-specific CD8$^{pos}$ T cells was most pronounced in the presence of avelumab when compared to mAb 29E.2A3. The use of viral peptides as antigens is a major difference, as in this case most likely memory CD8$^{pos}$ T cells are activated rather than naïve T cells. Brown et al. 2003 (J Immunol 170:1257-1266) used moDCs as stimulator cells, however, performed allogeneic mixed lymphocyte reactions, evaluating CD4$^{pos}$ T-cell activation in the presence of the mAb 29E.2A3. In this setting the presence of allogeneic HLA-antigens may serve as a danger signal, also inducing overall T-cell activation, including memory T-cell activation (Merrick et al. 2008, Cancer Immunol immunother 57:897-906). Re-activation of antigen-experienced effector memory T cells was suggested to be the driver of the efficacy of PD-L1/PD1 blockade in human cancer therapy, while activation of CD8$^{pos}$ effector T cells was not reported (Ribas et al. 2016, Cancer Immunol Res 4:194-203). The source of stimulator cells might also contribute to the difference in experimental outcome. We observed that mAb 29E.2A3 was unable to detect PD-L1 in flow cytometry on the moDCs we generated, and that detection of PD-L1 with avelumab was less evident as with mAb MH1 and sdAb K2. Staining op PD-L1 expressed on 293T cells precludes that this observation is a technical artefact, as avelumab, mAbs 29E.2A3 and MIH1 as well as sdAb K2, were able to stain PD-L1 on these cells. The reason for this different sensitivity to PD-L1 expressed on moDCs versus 293T cells is at present unclear, however, provides an explanation as to why de novo activation of antigen-specific CD8$^{pos}$ T cells was not observed in the presence of these mAbs in our study. It is conceivable that our moDCs differ from the moDCs used by Brown et al. 2003 (J Immunol 170:1257-1266), as different culture conditions were used [e.g. culture medium]. For sure, the moDCs used in this study are different from the PBMCs used by Grenga et al. 2016 (Clin Transl immunol 5:e83). Further studies are required to assess binding of different mAbs to different PD-L1$^{pos}$ immune and non-immune cell populations, including DCs. Such studies have already been performed with other antibodies in the context of immunohistochemical detection of PD-L1 in tumour tissue and lymph nodes, showing that different antibodies indeed have different propensities to bind PD-L1 on tumour cells versus immune cells, and sometimes even discriminate between lymphocyte-like cells versus DCs (Schats et al. 2018, Arch Pathol Lab Med 142:982-991). In our study, sdAb K2, similar to mAb MIH1, did not make the distinction between PD-L1 expressed on moDCs versus 293T cells.

We previously showed that sdAb K2 competes with avelumab for binding to PD-L1. Studies showed that avelumab binds mainly with its VH domain on the strands of the front β-sheet face of the IgV domain of PD-L1, which is different from the epitopes bound by other PD-L1 targeting mAbs, such as durvalumab, atezolizumab and BMS-936559 (Liu et al. 2017, Cell Res 27:151-153; Tan et al. 2018, Protein Cell 9:135-139). As such sdAb K2 is a unique small-sized, biological inhibitor, when compared to other small molecule inhibitors, such as the anti-PD-L1 sdAb KN035 and the non-peptide anti-PD-L1 inhibitors, BMS-202 and BMS-8, which show similar binding to PD-L1 as durvalumab (Tan et al. 2018, Protein Cell 9:135-139; Zhang et al. 2017, Cell Discov 3:17004). We showed that sdAb K2 blocks PD-1/PD-L1 interactions on the protein level and tumour cell-T cell level. We now show that sdAb K2 can also block PD-1/PD-L1 interactions at the immunological synapse created when DCs interact with $CD8^{pos}$ T cells. The single domain nature of sdAbs offers interesting perspectives in view of DC-vaccine development. Many protocols are available to deliver tumour antigens and activation stimuli to DCs. Many of these are based on genetic engineering using viral and non-viral vectors (Breckpot et al. 2004, J Gene Med 6:1175-1188; Benteyn et al. 2015, Expert Rev Vaccines 14:161-176). While cloning of classical mAbs or mAb-fragments offers serious challenges, cloning of sdAbs is straightforward, therefore can be easily incorporated into existing DC-engineering protocols. Several of these ex vivo DC-engineering strategies have also been used to specifically engineer DCs in situ, even in the tumour environment (Van Lint et al. 2012, Cancer Res 72:1661-1671; Van Lint et al. 2016, Cancer Immunol Res 4:146-156; Goyvaerts et al. 2013, J Virol 87:11304-11308; Van der Jeught et al. 2018, ACS Nano 12:9815-9829; Verbeke et al. 2019, ACS Nano). The targeted delivery of sdAb K2, and its release in the immunological synapse offers attractive safety considerations compared to systemic mAb or sdAb-administration. It will tip the balance from immune inhibitory to stimulatory signals only between antigen and sdAb K2-engineered DCs and cognate T cells, thereby ensuring increased on-target T-cell responses with little to no off-target T-cell activation.

In conclusion, we report on the use of sdAb K2, a versatile PD-L1/PD-1 blocking moiety, to enhance the capacity of DCs to stimulate T-cell activation and cytokine production. Inclusion of sdAb K2 in DC-vaccination protocols may have therapeutic potential in the clinical setting where several technologies to modify DCs for T-cell activation are investigated in the setting of cancer as well as infectious disease.

2.5. sdAb K2 Maintains T-Cell Activation During Interaction with Tumour Cells

The PD-1:PD-L1 immune checkpoint axis is a major culprit in the tumour microenvironment. Therefore, we evaluated whether T cells electroporated with mRNA encoding PD-1 and the TCR recognizing $gp100_{280-288}$ in the context of HLA-A2 were hampered in their ability to proliferate and produce IFN-gamma upon interaction with $gp100_{280-288}$ presenting HLA-A2$^+$ tumour cells that are PD-L1$^-$ or PD-L1$^+$.

2.6. sdAb K2 is a Promising Theranostic

The first patient studies with blocking antibodies were correlated to the PD-L1 status of tumours using immunohistochemical staining (IHC) of tumour biopsies, confirming that responses were significantly higher in PD-L1 expressing tumours. Nonetheless, in subsequent studies, responses were also observed in PD-L1 negative cancers, although to a lesser extent (Topalian et al. 2012, N Engl J Med 366:2443-2454). These observations highlight the need for tools that allow assessment of PD-L1 expression, and that can target PD-L1 within the tumour microenvironment to maintain the function of T cells. As sdAb K2 is suited for imaging of PD-L1 and as our in vitro assays suggest it has the potential to activate and maintain the function of CD8$^+$ T cells, we studied whether PD-L1 upregulation on 624-MEL cells upon interaction with tumour specific T cells could be visualized in SPECT/CT imaging with $^{99m}$-Tc sdAb K2, and whether the signal predicted the outcome of therapy with sdAb K2.

2.7 Kidney Uptake of Various huPDL1-Binding Agents.

Table 2 lists kidney uptake values for the huPDL1-binding nanobodies of the current invention, and for other huPDL1-binding agents and murine PDL1-binding nanobodies:

- murine PDL1-binding nanobody C3: Broos et al. 2017 (Oncotarget 8:41932)
- affibody: Gonzalez et al. 2017 (J Nucl Med 58:1852)
- adnectins: Donnely et al. 2017 (J Nucl Med doi:10.2967/jnumed.117.199596)
- macrocyclic peptide: Chatterjee et al. 2017 (Biochem Biophys Res Comm 483:258)
- ectodomain huPD-1: Maute et al. 2015 (Proc Natl Acad Sci 112:E6506).

Figure 4B:
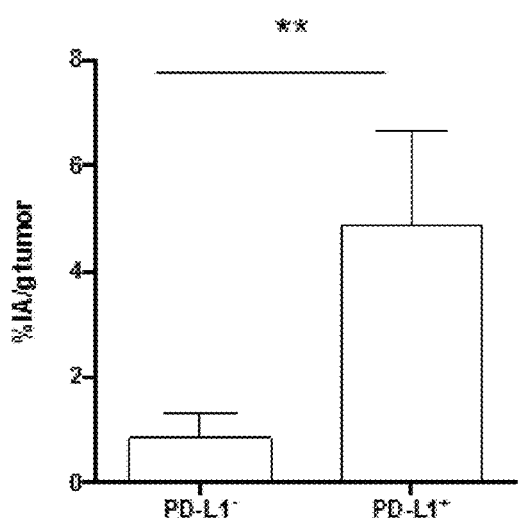
Figure 4C:
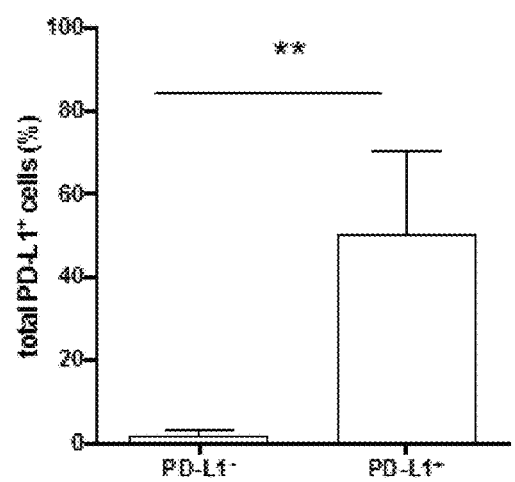

% IA/g (as also referred to in Legends to FIGS. 3, 4, and 8, and in Examples 1.8 and 2): uptake of the radiolabel in different tissues is expressed by % IA/g or % of injected activity per gram of tissue. If it refers to organs (such as kidneys), it means that at the indicated time point post injection, the mouse was killed, dissected and organs (such as kidneys) were removed. All organs are weighed and radioactivity was counted in a gamma counter. This results in a number of counts per minute (or second). This is arbitrary as it will go down over time with the decay of the radionuclide. Therefore, a standard is also measured in the gamma counter and the counts in the organs (e.g. kidneys) is then correlated to the counts in the standard by which it is extrapolated to the amount of radioactivity that was injected (IA). The uptake in the organs is then expressed as the relative uptake of the injected activity (so % of total amount of injected activity or % IA). This is then divided by the weight of the organs, resulting in a value in % IA/g. This can be higher than 100%, because the kidneys do not weigh a full gram in mice (typically around 100 mg).

| agent | labelling | animal model | time point post injection | uptake kidneys (% IA/g) |
|---|---|---|---|---|
| K2 (huPDL1 nanobody) | 99m-Tc | naive C57BL/6 mice | 80 min | 34.02 |
| K3 (huPDL1 nanobody) | 99m-Tc | naive C57BL/6 mice | 80 min | 56.41 |

| agent | labelling | animal model | time point post injection | uptake kidneys (% IA/g) |
|---|---|---|---|---|
| K2 (huPDL1 nanobody) | 99m-Tc | athymic nude mice bearing MCF7 PD-L1 negative tumor | 80 min | 14.40 |
| K2 (huPDL1 nanobody) | 99m-Tc | athymic nude mice bearing MCF7 PD-L1 positive tumor | 80 min | 15.23 |
| K2 (huPDL1 nanobody) | 99m-Tc | athymic nude mice bearing MEL624 PD-L1 negative tumor | 80 min | 17.22 |
| K2 (huPDL1 nanobody) | 99m-Tc | athymic nude mice bearing MEL624 PD-L1 positive tumor | 80 min | 17.10 |
| K2 (huPDL1 nanobody) | 68-Ga (site specific coupling) | naive C57BL/6 mice | 80 min | 10.06 |
| K2 (huPDL1 nanobody) | 68-Ga (random coupling) | naive C57BL/6 mice | 80 min | 19.18 |
| C3 (muPDL1 nanobody) | 99m-Tc | naive C57BL/6 mice | 80 min | 212.00 |
| C3 (muPDL1 nanobody) | 99m-Tc | PD-L1 KO mice | 80 min | 316.10 |
| C3 (muPDL1 nanobody) | 99m-Tc | C57BL/6 mice bearing PD-L1 positive tumor (TC-1 WT) | 80 min | 114.30 |
| C3 (muPDL1 nanobody) | 99m-Tc | PD-L1 KO mice bearing PD-L1 knock-out tumor (TC-1 KO) | 80 min | 178.00 |
| C3 (muPDL1 nanobody) | 99m-Tc | C57BL/6 mice bearing PD-L1 overexpressing tumor (TC-1 KI) | 80 min | 197.30 |
| C3 (muPDL1 nanobody) | 99m-Tc | C57BL/6 mice bearing TC-1 WT PD-L1 knock down tumor | 80 min | 205.40 |
| huPD-1 ectodomain | 64-Cu | NSG mice with CT26 tumor models | 1 h | between 100 and 125 |
| huPDL1 affibody | 18-F | Female SCID Beige mice bearing LOX tumor | 90 min | 312.69 |
| huPDL1 affibody | 18-F | Female SCID Beige mice bearing SUDHL6 tumor | 90 min | 254.59 |
| huPDL1 adrectin | 18-F | mice implanted with L2987 and HT-29 xenografts | 90 min | cpm/ID/ tissue weight |
| huPDL1 macrocyclic peptide WL-12 | 64Cu | NSG mice bearing hPD-L1 positive and negative tumors | 1 h | between 30 en 40 |

3. Site-Specific Radiolabelling

Immune checkpoints such as Programmed death-ligand 1 (PD-L1) limit the T-cell function, and tumour cells have developed this receptor to escape the anti-tumour immune response. Monoclonal antibody-based treatments have shown long-lasting responses, but only in a subset of patients. Therefore, there is a need to predict response to treatments. In support of this, an IVD-based probe to assess human PD-L1 (hPD-L1) expression using PET imaging was developed by site-specific coupling of the anti-PD-L1 sdAb to the NOTA-chelator for $^{68}$Ga labelling, or to the RESCA-chelator for [$^{18}$F]AlF labelling. As a comparison study, anti-PD-L1 IVD was also coupled to the NOTA-chelator by the random coupling strategy, since this strategy is already implemented in the production of other sdAbs in clinical trials.

The anti-hPD-L1 sdAb K2 with a sortag-motif (sortase A amino acid substrate motif) at its C-terminal was site-specifically coupled to a bifunctional chelator (BFC) via the Sortase A enzyme coupling reaction. BFCs were synthesized by attaching p-SCN-Bn-NOTA or RESCA-(tBu)—COOH to a GGGYK peptide. Site-specifically modified anti-hPD-L1 sdAb K2 were purified by incubation with 150 M EDTA solution, by IMAC and by size exclusion chromatography (SEC).

For random functionalization, 6×Histidine-tagged anti-hPD-L1 sdAb K2 in 0.05 M sodium carbonate buffer, pH 8.7 was added to a twenty-fold excess of the p-SCN-Bn-NOTA BFC, pH adjusted to 8.5-8.7 with 0.2 M Na2CO3. After 2 h incubation at room temperature (RT), the pH of the reaction mixture was lowered to pH 7.4 by adding HCl 1N. The NOTA-(anti-hPD-L1 sdAb K2) protein solution was loaded on a SEC column. The collected fractions containing monomeric NOTA-anti-hPD-L1 sdAb K2 protein were pooled.

Modified anti-hPD-L1 sdAb K2 were characterized by Mass Spectrometry (ESI-Q-TOF), SDS-PAGE and Western Blot. NOTA-(anti-hPD-L1 sdAb K2), site-specific and random, were labelled with 68Ga and RESCA-(anti-hPD-L1 sdAb K2) with [$^{18}$F]AlF. Radiochemical purity (RCP) was assayed by SEC and iTLC. Stability of site-specifically radiolabelled probes was evaluated in vitro. Binding capacity of [$^{68}$Ga]Ga-NOTA-(anti-hPD-L1 sdAb K2) was evaluated in vitro on PD-L1 positive mel624 cells and compared with the randomly $^{68}$Ga-labelled anti-hPD-L1 sdAb K2, while affinity and specificity were tested on PD-L1 negative cells and on PD-L1 positive cells in presence of a 100 fold excess of unlabelled sdAb K2. In vivo stability (Blood curve and metabolization study) was performed with both random and site-specific [$^{68}$Ga]Ga-NOTA-(anti-hPD-L1 sdAb K2), as well as with site-specific [$^{67}$Ga]Ga-NOTA-(anti-hPD-L1 sdAb K2) by analyzing blood and urine samples from different time points. In vivo biodistribution in C57BL/6 mice was performed with both random and site-specific [$^{68}$Ga]Ga-NOTA-(anti-hPD-L1 sdAb K2), as well as with site-specific [$^{67}$Ga]Ga-NOTA-(anti-hPD-L1 sdAb K2) and [$^{18}$F]AlF-RESCA-(anti-hPD-L1 sdAb K2). In vivo tumour targeting studies were performed with both random and site-specific [$^{68}$Ga]Ga-NOTA-(anti-hPD-L1 sdAb K2) in xenografted-athymic nude mice bearing PD-L1 positive cells, or PD-L1 negative cells as a control. In vivo tumour targeting was also performed with site-specific [$^{67}$Ga]Ga-NOTA-(anti-hPD-L1 sdAb K2) in xenografted-athymic nude mice bearing PD-L1 positive cells. PET/CT and SPECT/CT imaging of tumour-bearing mice was performed with site-specific [$^{68}$Ga]Ga-NOTA-(anti-hPD-L1 sdAb K2) and [$^{67}$Ga]Ga-NOTA-(anti-hPD-L1 sdAb K2) respectively.

Site-specifically functionalized anti-hPD-L1 sdAb K2 with NOTA and RESCA were obtained with high purity (≥99%) in 56% and 59% yield respectively. Functionalization did not affect affinity nor specificity. Randomly functionalized anti-hPD-L1 sdAb K2 was obtained in 52% yield.

Radiolabelling of both random and site-site-specific NOTA-(anti-hPD-L1 sdAb K2) with $^{68}$Ga was performed at RT for 10 min at pH 4.4-4.7 in a 80% decay corrected radiochemical yield (DC-RCY) and ≥99% RCP. Apparent molar specific activity of 85 GBq/μmol was obtained for the site-specifically radiolabelled sdAb K2, and 63 GBq/μmol for the randomly radiolabelled sdAb K2. Over 4 hours, the site-specifically radiolabelled probe and metal complex were stable in injection buffer and in presence of DTPA excess (≥99% RCP). RCP after 1 hour at 37° C. in human serum was ≥94%.

Site-specific radiolabelling with $^{67}$Ga was performed at rt for 10 min at pH 4.4-4.7 in a 86% DC-RCY, ≥95% RCP with an apparent molar specific activity up to 40 GBq/μmol. The radiolabelled probe was stable in injection buffer over 17 h (≥98% RCP) and in human serum at 37° C. over 4 h (≥0.95% RCP).

In vivo metabolization studies with site-specific [$^{67}$Ga] Ga-NOTA-(hPD-L1) showed that the probe was ≥95% intact in the blood and ≥90% intact in the urines after 2 hours.

Figure 10A:
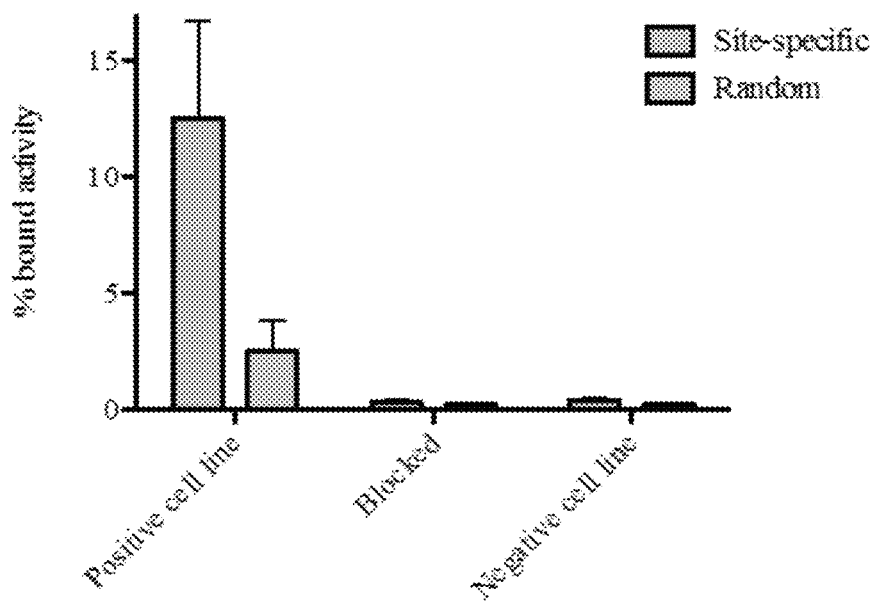
FIGS. 10A-10C.
Figure 10B:
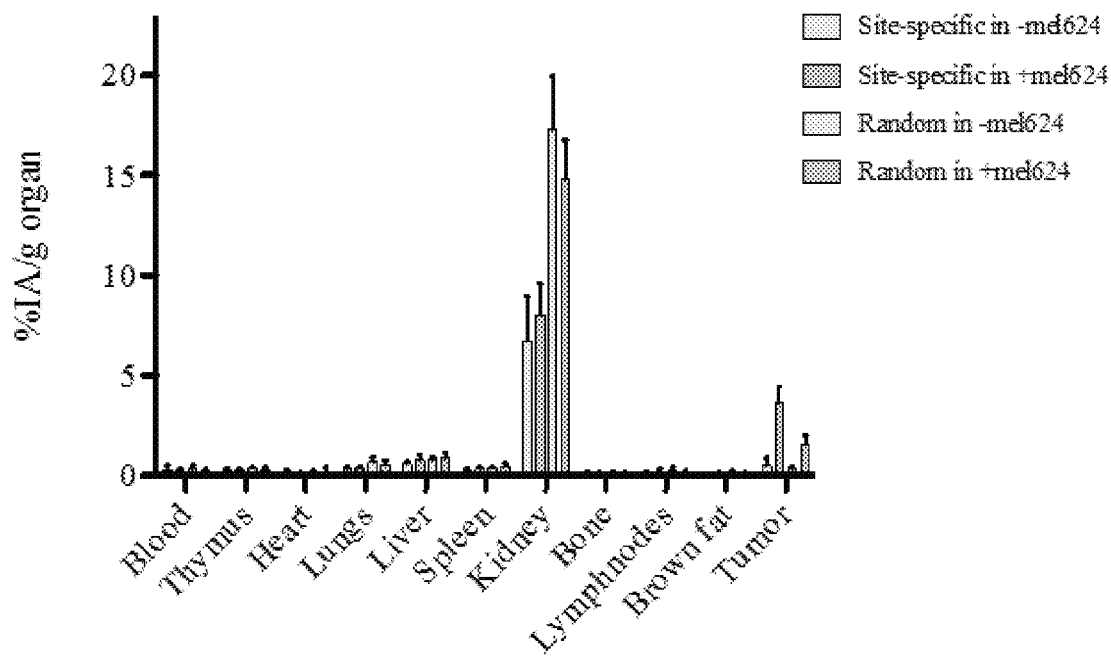

In vivo tumour targeting and biodistribution studies with both random and site-specific [$^{68}$Ga]Ga-NOTA-(anti-hPD-L1sdAb K2) revealed high tumour uptake of (3.664±0.764) % IA/g organ for the site-specific compared to (1.551±0.467) % IA/g organ for the random (see FIG. 10B). No unspecific organ targeting was observed, except in the kidneys (see FIG. 10B) and excretion to the bladder (expected route of excretion). Compared to random $^{68}$Ga-labelled sdAb K2, kidney accumulation of site-specific $^{68}$Ga-labelled sdAb K2 is lower whereas tumour uptake of site-specific $^{68}$Ga-labelled sdAb K2 is higher, therewith increasing the signal/noise ratio and increasing tumour-selective labelling. Similar selectivity of site-specific $^{68}$Ga-labelled sdAb K2 compared to random $^{68}$Ga-labelled sdAb K2 was observed on PD-L1+ cells (see FIG. 10A).

Figure 10C:
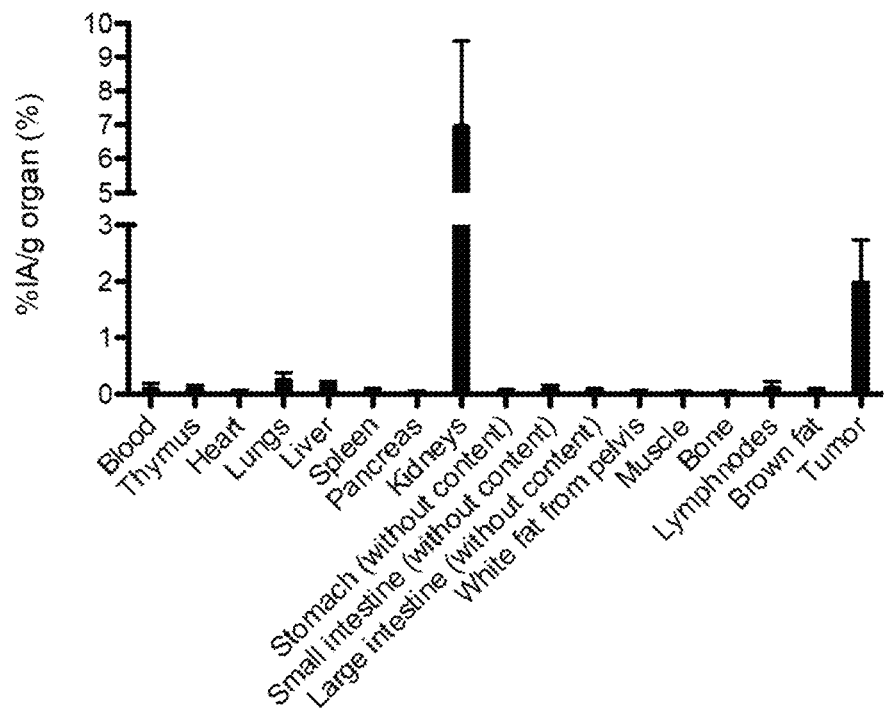

In vivo tumour targeting and biodistribution studies profiles obtained with site-specific [$^{67}$Ga]Ga-NOTA-(anti-hPD-L1 sdAb K2) were similar as for $^{68}$Ga labelled probe (see FIG. 10C). Tumour uptake was slightly lower as previous experiments, which can be explained by the different position of the tumour (neck region instead of leg) and a longer tumour growing period in vivo, leading to necrotic tumours.

Quantification of SPECT/CT scans with $^{67}$Ga-labeled allowed to quantify tumour uptake, giving similar results as the ex-vivo measurement: 0.328% of total injected activity quantified from scan compared with 0.350% of total injected activity calculated dissected tumour.

Radiolabelling of RESCA-(anti-hPD-L1 sdAb K2) with [$^{18}$F]AlF was performed at rt for 12 min at pH 4.4-4.7 in a 29% DC-RCY and with a RCP≥99%. The radiolabelled probe was stable over 2.5 hours in injection buffer (RCP≥98%). Biodistribution in healthy animals was similar as for [$^{68}$Ga]Ga-NOTA-(hPD-L1), except for slightly higher bone uptake.

The Sortase enzyme-mediated labelling approach thus allowed to obtain a site-specifically functionalized anti-hPD-L1 sdAbs, which could be easily radiolabelled with $^{67}$Ga, $^{67}$Ga or [$^{18}$F]AlF. [$^{68}$Ga]Ga-NOTA-(anti-hPD-L1 sdAbs) proved to specifically target the hPD-L1 receptor in vivo and the targeting experiment will be repeated with [$^{18}$F]AlF-RESCA-(anti-hPD-L1 sdAbs). SPECT/CT images obtained with 67Ga-labelled probe proved to be quantifiable.

4. Detection of Human PD-L1 Induced by IFN-γ in Xenograft Tumour Models by sdAb K2

Figure 15A:
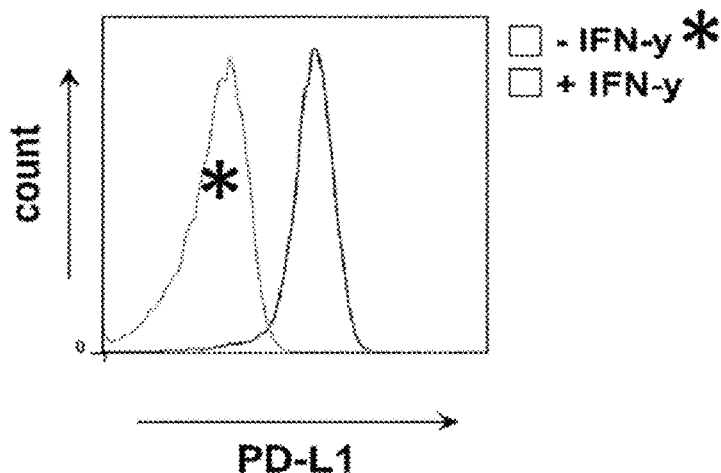
FIGS. 15A-15E. Radiolabelled sdAb K2 allows specific visualization of human PD-L1 induced by IFN-γ in 938-MEL tumours.
Figure 15B:
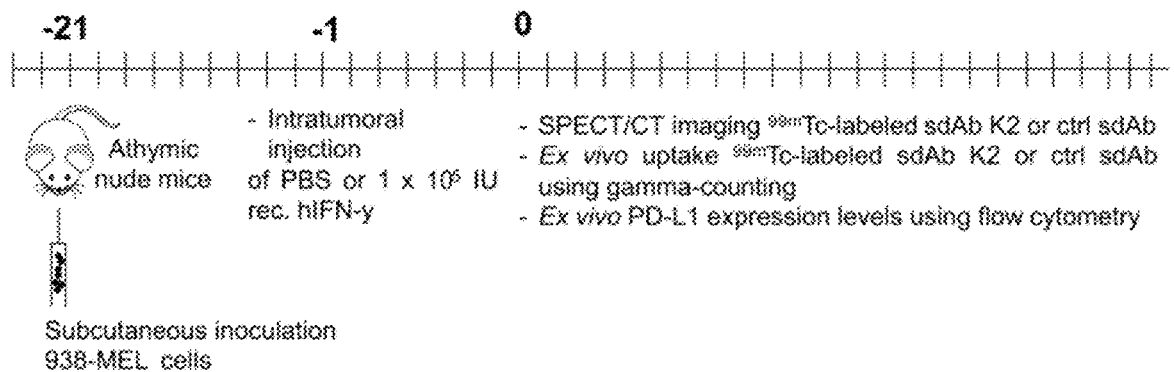
Figure 15C:
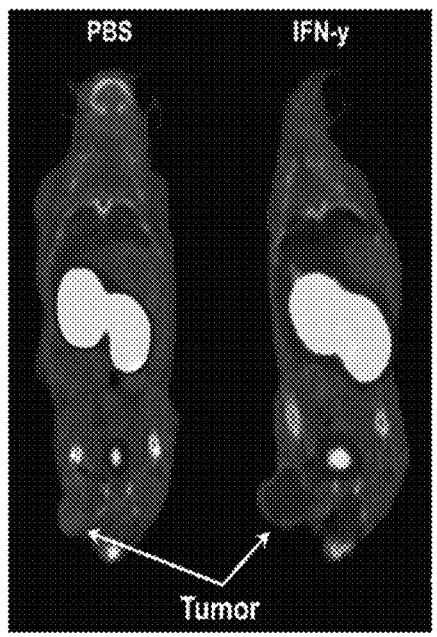
Figure 15D:
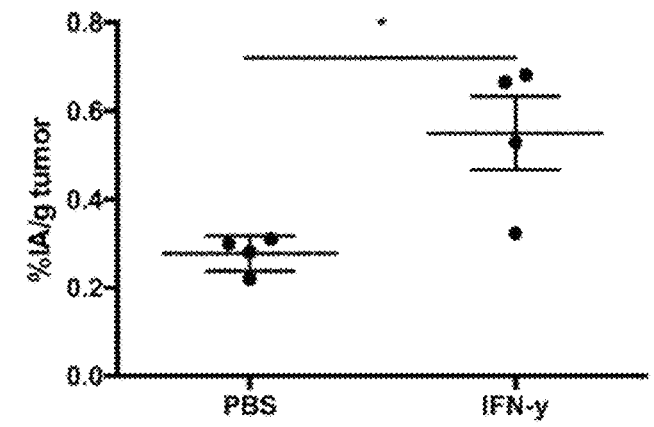
Figure 15E:
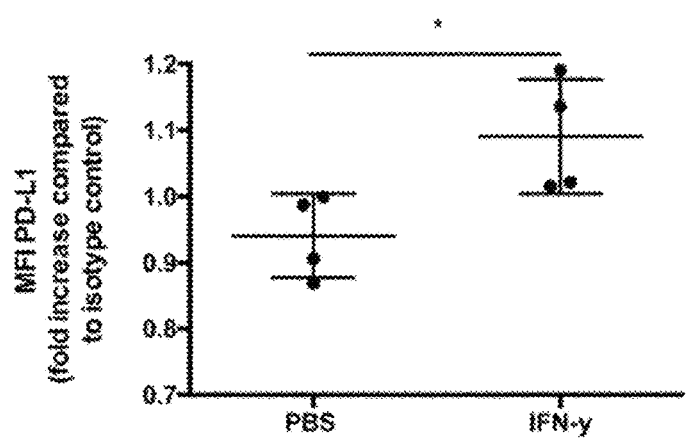

Following validation in two PDL1-engineered tumour cell mouse models, we evaluated whether sdAb K2 can be used to detect PD-L1 expression in response to IFN-γ. The 938-MEL model was used as we observed in flow cytometry that in vitro treatment of 938-MEL cells with 100 IU/mL IFN-γ leads to upregulation of PD-L1 (FIG. 15A). We next injected recombinant IFN-γ in 938-MEL tumours grown in athymic nude mice and used 99m Tc-sdAb K2 and SPECT/CT imaging to evaluate PD-L1 expression (FIG. 15B). Tumours of on average 150 mm3 were injected with PBS (negative control) or 104 IUs IFN-γ. One day later, we performed SPECT/CT imaging, showing detection of PD-L1 in the tumour of IFN-γ but not of PBS-treated mice (FIG. 15C). Furthermore, ex vivo γ-counting showed higher uptake of 99m Tc-sdAb K2 in mice treated with IFN-γ (0.55±0.08% IA/g) compared to mice treated with PBS (0.28±0.02% IA/g) (FIG. 15D). Evaluation of PD-L1 expression on tumour cells using flow cytometry confirmed higher PD-L1 expression on IFN-γ-treated tumours compared to PBS-treated tumours, although PD-L1 expression levels were low (FIG. 15E).

5. sdAb K2 Competes with Avelumab for Binding to PD-L1 and has PD-1:PD-L1 Blocking Capacity We showed that sdAb K2 serves as a potential diagnostic tool to detect PD-L1 expression levels in vivo on tumour cells and as such might select patients for anti-PD-L1 treatment. We next wondered whether sdAb K2 also has therapeutic potential and evaluated whether sdAb K2 is able to inhibit the PD-1:PD-L1 interaction leading to enhanced T-cell activity. We showed by SPR that sdAb K2 recognizes the same epitope on PD-L1 as avelumab (FIG. 16A). Moreover, sdAb K2 is able to inhibit the interaction between PD-1:PD-L1 with an IC50 of 8.5 nM. In the same assay, the IC50 value of avelumab was 4 nM, whereas both controls, R3B23 and trastuzumab, did not influence the PD-1:PD-L1 interaction (FIG. 16B).

6. sdAb K2 Restores the Tumour Cell Killing Ability of Activated PBMCs

Figure 17A:
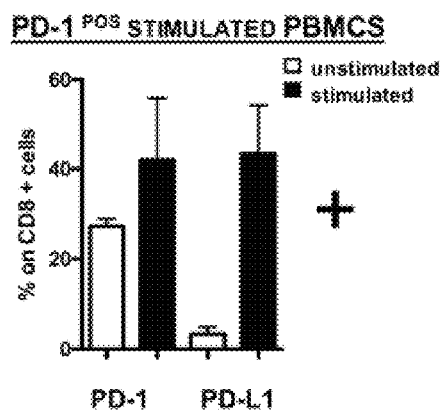
FIGS. 17A-17G. sdAb K2 and avelumab show in vitro therapeutic effects with different kinetics.
Figure 17B:
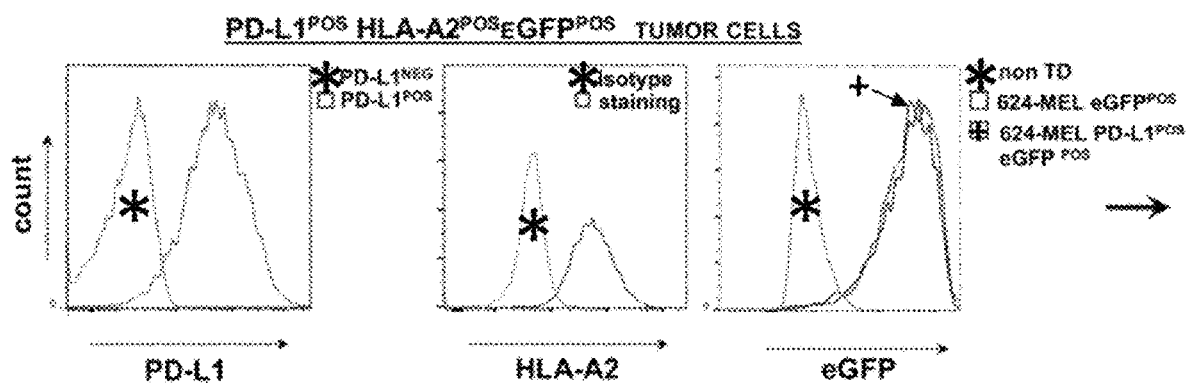
Figure 17C:
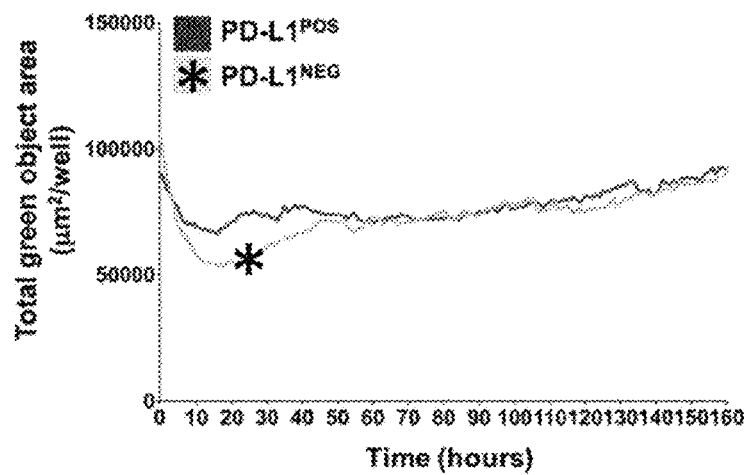
Figure 17D:
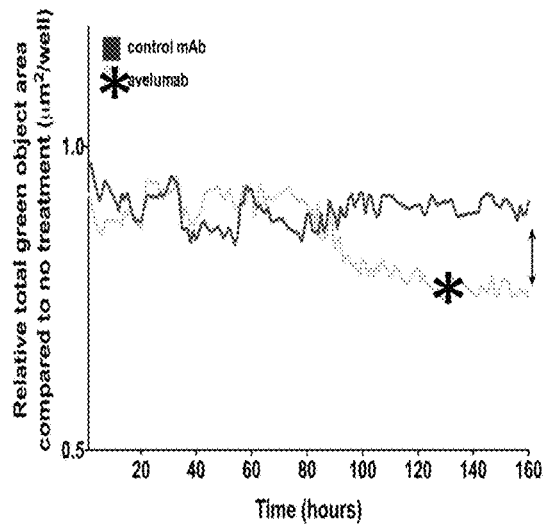
Figure 17E:
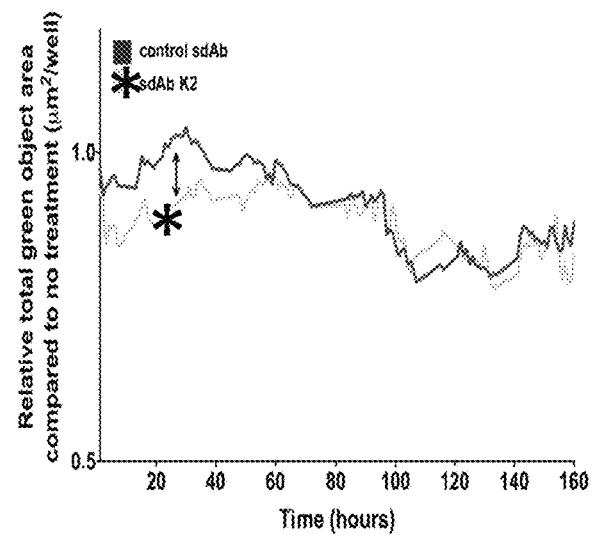
Figure 17F:
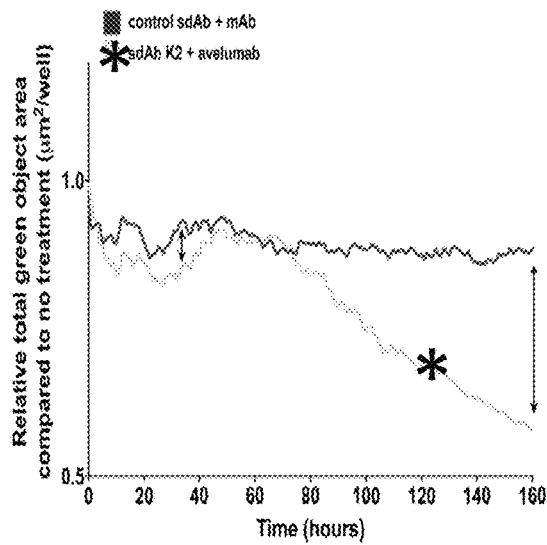
Figure 17G:
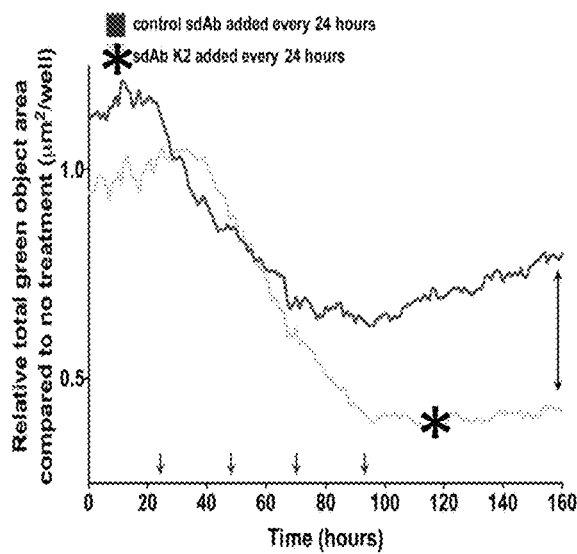

We explored the effect of adding sdAb K2 to co-cultures of activated PBMCs and tumour cells. First, we evaluated the expression of PD-1 and PD-L1 on CD8POS T cells, present within the pool of PBMCs stimulated with a cocktail of anti-CD3 antibodies and IL-2, as these cells are critical to mediate tumour cell killing. We showed using flow cytometry that both PD-1 and PD-L1 were upregulated on CD8POS T cells, thereby confirming activation of these cells (FIG. 17A). The activated cells were added to PD-L1pos 624-MEL cells that were lentivirally engineered to express eGFP (FIG. 17B) and that were grown in a 3D spheroid. In the absence of PD-1:PD-L1 blocking moieties, we observed that the amount of eGFPPOS tumour cells, measured as green objective area, increased in time, or in other words were not destroyed sufficiently by activated T cells, confirming the inhibitory role of PD-L1 on T cell-mediated tumour cell killing (FIG. 17C). Addition of avelumab or sdAb K2 to PD-L1POS tumour cells and stimulated PBMCs enhanced tumour cell killing when compared to addition of a control mAbs or R3B23, as measured as reduction in green objective area (FIG. 17D-E). The effect of adding avelumab on tumour cell killing could be observed at 80 hours (FIG. 17D), while the effect of sdAb K2 was observed in the first hours of culture (FIG. 17E). Hence, sdAb K2 showed early and short therapeutic activity, while avelumab showed a more durable blocking activity. To enhance the blocking activity, we evaluated 329 the effect of combined sdAb K2 and avelumab treatment, showing more efficient tumour cell killing (after 70 hours) compared to addition of avelumab or sdAb K2 separately (FIG. 17F). Remedying the short action of sdAb K2, we tested the effect of repeated administrations of sdAb K2 with 24-hour intervals. This resulted in efficient tumour cell killing by activated PBMCs after 50 hours (FIG. 17G), supporting the therapeutic potential of sdAb K2.

7. Discussion

In this study we showed that the sdAb, designated sdAb K2, is able to detect human PD-L1 expression levels in the tumour microenvironment and to block PD-L1 on tumour cells resulting in enhanced T-cell activity. sdAb K2 binds with nanomolar affinity to human PD-L1 and can be used as a diagnostic to detect PD-L1 expression in the tumour as fast as one hour after injection. PD-L1 expression could even be detected after intratumoural administration of IFN-γ, which led to in situ upregulation of PD-L1, although expression levels remained low. Moreover, we showed that sdAb K2 has therapeutic potential as it exhibits an IC50 of 8.5 nM to block PD-1:PD-L1 interactions and releases the break on antigen-specific TCR signalling and on tumour killing activity in vitro. Nowadays, in clinical trials, PD-L1 expression is mainly evaluated by IHC, which has some limitations. Staining of fixed selected tissue samples does not allow assessment of heterogenic expression of tumour markers, or the dynamic PD-L1 expression during treatment. Molecular imaging is a good alternative to assess PD-L1 expression, as this non-invasive method can show regional differences within the tumour environment and can assess PD-L1 expression in metastatic lesions. Here, we showed that sdAb K2 has several properties to make it an interesting diagnostic. Ideal radiotracers combine fast renal clearance and efficient tumour penetration with good affinity for their target, resulting in high tumour-to-background ratios shortly after tracer administration. We showed that 99m Tc-sdAb K2 fulfils these requirement since administration in healthy C57BL/6 mice revealed little to no signals in all organs except in the kidneys and urinary bladder, which is due to the renal uptake and elimination because of their small size (Chakravarty et al. 2014, Theranostics 4:386-398). Noteworthy, the uptake of 99m Tc-sdAb K2 in the kidneys was much lower compared to 99m Tc-R3B23, the sdAb used as a negative control, and to our knowledge any other sdAb that was labelled in a similar fashion. This low kidney retention makes sdAb K2 particularly suited as a radiotracer, since such important decrease in kidney retention not only lowers the irradiation burden for the patient but also improves the assessment of lesions in the vicinity of the kidneys. This can be useful to assess patients with renal cell carcinoma for expression of PD-L1, as these patients can derive benefit from such treatments (Alsaab et al. 2017, Front Pharmacol 8:561). 99m Tc-sdAb K2 showed intense and specific uptake in two human PD-L1-expressing tumour models, melanoma and breast cancer, with tumour-to-blood ratios of 20.2 and 8.9, respectively. Moreover, PD-L1 expression could be detected after intratumoural injection of IFN-γ, leading to elevated, albeit still low, PD-L1 expression levels on tumour cells, as confirmed with flow cytometry. In all imaging studies, high tumour-to-background uptake levels could be obtained as fast as one hour after injection. When translated to patients, this would allow short, same-day imaging procedures, very similar to the current daily practice with 18F-FDG (Vaneycken et al. 2011, FASEB J 25:2433-2446). The absolute tumour uptake we observed with sdAb K2 is at the same level compared to other studies using sdAbs that target tumours (Xavier et al. 2013, J Nucl Med 54:776-784; Xavier et al. 2019, Mol Imaging Biol). Although absolute tumour uptake for sdAbs is generally lower than what can be obtained with mAb, the contrast that can be obtained at early time points is much higher, due to the very fast clearance of the unbound tracer. For future clinical translation, the here proposed SPECT tracer will be further engineered into a clinical PET-tracer, similar to what was done for other sdAb translations (Keyaerts et al. 2016, J Nucl Med 57:27-33; Xavier et al. 2013, J Nucl Med 54:776-784; Xavier et al. 2019, Mol Imaging Biol). Other research groups have as well developed radiotracers for PD-L1 imaging using both mAbs (Bensch et al. 2018, Nat Med 12:1852-1858; Lesniak et al. 2016, Bioconjug Chem 27:2103-2110) or smaller proteins (Chatterjee et al. 2017, Biochem Biophys Res Commun 483:258-263; Donnelly et al. 2017, J Nucl Med 59:529-535; Niemeijer et al. 2018, Nat Commun 9:4664) of which some have entered clinical testing. Bensch et al used 89Zr-labelled atezolizumab, a clinically approved therapeutic mAb, for molecular imaging in cancer patients (Bensch et al. 2018, Nat Med 12:1852-1858). A better correlation between PET images and clinical responses compared to IHC was reported. However, optimal tumour-to-blood ratios were only obtained on day 7 after injection (Bensch et al. 2018, Nat Med 12:1852-1858). This time point could be tangibly reduced to 5 days using a 89Zr-labelled-heavy chain-only antibody KN035 (i.e. an anti-PD-L1 sdAb fused to an Fc domain), which is smaller (80 kDa) than a full antibody (150 kDa) but still is substantially larger than sdAbs such as sdAb K2 (15 kDa). However, the tumour-to-blood ratios reported were low, i.e. 1.1 (Li et al. 2018, Mol Pharm 15:1674-1681). The 18F-labelled adnectin 18F-BMS-986192 has a size of about 10 kDa, and is therefore at least in terms of size closer to sdAbs. This compound could visualize PD-L1POS tumours with a 3.5-fold higher uptake in PD-L1POS versus PD-L1NEG tumours using PET imaging in mice. However, kidney uptake of 18F-BMS-986192 was relatively high (Donnelly et al. 2017, J Nucl Med 59:529-535). This compound was as well recently evaluated in cancer patients (non-small-cell lung cancer). Tracer uptake in the tumour correlated with PD-L1 expression levels on tumour cells evaluated with IHC. However, a subset of tumours showed low PD-L1 expression by IHC but relatively high uptake with 18F-labelled adnectin, which could be explained by the heterogeneity of PD-L1 in the lesion. Furthermore, response rates correlated with tracer uptake, with responders showing higher tracer uptake compared to non-responders (Niemeijer et al. 2018, Nat Commun 9:4664). These observations make us believe that small imaging agents, such as the here presented sdAb K2, can be used as a diagnostic tool in cancer patients. Indeed, sdAb K2 is able to image PD-L1 with high contrast levels as fast as one hour after injection, which is much faster than imaging with 89Zr-labelled atezolizumab. Secondly, because of its small size sdAb K2 is able to efficiently penetrate tumours resulting in higher tumour-to-blood ratios compared to compound KN035 (8.9 and 20.2 for sdAb K2 compared to 1.1 for KN035). Finally, sdAb K2 is able to detect PD-L1 expression levels with higher contrast compared to similar-sized 395 18F-labelled adnectin (tumour-to-blood ratios of 8.9 and 20.2 for sdAb K2 versus <3 for the adnectin at the same time point) and with lower kidney retention. Besides its diagnostic value, we furthermore evaluated the therapeutic value of sdAb K2. The use of sdAbs for therapy exhibits some advantages compared to mAbs. sdAbs are 10 times smaller than mAbs and are therefore better suited for fast and homogenous tumour penetration. As the PD-(L)1 immune checkpoint is mainly relevant in the tumour microenvironment rather than in other immune organs (Zou et al. 2016, Sci Transl Med 8:328rv4), this could be a key characteristic for optimal therapeutic effect in larger, difficult-to-penetrate tumours, which was observed for the HAC-I variant (10 kDa; KD=100 pM; IC50=210 pM) for example. This smaller blocking moiety induced equal tumour reduction compared to mAbs targeting human PD-L1 when treating smaller tumours, but when larger tumours were treated it appeared that the mAb lost its therapeutic efficiency whereas the HAC-I variant did not (Maute et al. 2015, PNAS USA 112:E6506-E6514). Also the previously described sdAb-Fc compound KN035 enhanced tumour cell killing in a xenograft model (Zhang et al. 2017, Cell Discov 3:17004). However, sdAbs that target human PD-L1 have not yet been studied in their monovalent format in a therapy setting. We were able to show that sdAb K2 binds to the same epitope on PD-L1 as the FDA-approved antibody avelumab and is able to block the PD-1:PD-L1 interaction in a similar magnitude as avelumab in a human antigen-specific T cell assay, even though the IC50 value of sdAb K2 was slightly higher. This difference in IC50 can be explained by the bivalent format of avelumab, which renders two binding places for avelumab compared to one for sdAb K2. When evaluating both compounds in the 3D tumour cell killing assay, we observed that tumour cell killing started rapidly after sdAb K2 addition, whereas for avelumab the effect was only observed after 80 hours. This may be explained by differences in valency, IC50 as well as diffusion between both agents. Whereas sdAb K2 is small and should be able to rapidly bind to its target, it likely also rapidly detaches from its target. In contrast, avelumab is larger and probably reaches its target later but the higher avidity due to the bivalent format results in better off-rates and longer retention times. Hence, as a therapeutic, repeated administration of sdAb K2 could be necessary to obtain the same effect as avelumab. Alternatively, sdAb K2 could be modified to a bivalent format to optimize its effect. We could already confirm in vitro that adding sdAb K2 every 24 hours had the same effect on activated PBMC-mediated tumour cell killing compared to adding one dose of avelumab. However, it remains to be shown if this could also improve clinical outcome. Exploiting their differences in pharmacokinetics and avidity we moreover demonstrate that combinatorial treatment with sdAb K2 and avelumab results in a superior antitumour killing effect. Further research to determine the exact value of such a combination approach in an in vivo tumour setting is warranted. Taken together, these data show that sdAb K2 holds promise as a small antagonistic therapeutic compound targeting human PD-L1.

The invention claimed is:

1. A polypeptide comprising an immunoglobulin variable domain (IVD) binding to human Programmed Death Ligand-1 (PD-L1), wherein the IVD comprises a CDR1 region, a CDR2 region, and a CDR3 region, and wherein the sequence of the IVD comprises the amino acid sequence set forth in any of SEQ ID Nos:1, 5, 8 or 11.

2. The polypeptide according to claim 1, wherein the IVD comprises the amino acid sequence set forth in SEQ ID NO:5.

3. The polypeptide according to claim 1, further comprising a functional moiety.

4. The polypeptide according to claim 3, wherein the functional moiety is a His-tag or sortase recognition sequence.

5. The polypeptide according to claim 3, wherein the functional moiety is a detectable moiety.

6. The polypeptide according to claim 5, wherein the detectable moiety is linked to a His-tag or sortase recognition sequence comprised in the polypeptide.

7. An isolated nucleic acid encoding a polypeptide according to claim 1.

8. A vector comprising the nucleic acid according to claim 7.

9. A host cell comprising the vector according to claim 8.

10. A method for producing a polypeptide, the method comprising:
    culturing the host cell of claim 9 so that the encoded polypeptide is expressed; and
    purifying the expressed polypeptide.

11. The method according to claim 10, further comprising coupling a detectable moiety to the purified polypeptide.

12. A host cell comprising an isolated nucleic acid according to claim 7.

13. A pharmaceutical composition comprising a polypeptide according to claim 1 and one or more immunotherapeutic or immunogenic agents.

* * * * *